US012674731B2

(12) United States Patent
Warrick et al.

(10) Patent No.: US 12,674,731 B2
(45) Date of Patent: Jul. 7, 2026

(54) DEVICES AND METHODS FOR VERTICAL FLOW-BASED DETECTION OF ANALYTES

(71) Applicant: SALUS DISCOVERY, LLC, Madison, WI (US)

(72) Inventors: Jay Warrick, Madison, WI (US); Cody Carrell, Sun Prairie, WI (US); Brianna Mullins, DeForest, WI (US); David Beebe, Monona, WI (US); Ryan Shogren, Madison, WI (US); Patrick McMinn, Madison, WI (US); Mitch Geiger, Madison, WI (US); Madalyn Gill, Madison, WI (US); Jeffrey Robert Staszak, Deerfield, WI (US); Visnu Devi Fraenkel, Madison, WI (US); Antonio Gatta, Philadelphia, PA (US); Eric S. Mackey, Wales, WI (US); Mckayla Rae Barber, Madison, WI (US); Randi Marie Degg, Seattle, WA (US); Madeline Sides, Carmichael, CA (US); Douglas Paul Barnes, Charlotte, NC (US); Franklin Cheng Zhong, Lee's Summit, MO (US); Mindy Phung, Houston, TX (US)

(73) Assignee: SALUS DISCOVERY, LLC, Madison, WI (US)

( * ) Notice: Subject to any disclaimer, the term of this patent is extended or adjusted under 35 U.S.C. 154(b) by 310 days.

(21) Appl. No.: 18/373,110

(22) Filed: Sep. 26, 2023

(65) Prior Publication Data

US 2024/0102901 A1    Mar. 28, 2024

Related U.S. Application Data

(60) Provisional application No. 63/410,389, filed on Sep. 27, 2022.

(51) Int. Cl.
*G01N 1/40* (2006.01)
*B01L 3/00* (2006.01)
*G01N 33/493* (2006.01)

(52) U.S. Cl.
CPC .......... *G01N 1/4005* (2013.01); *B01L 3/5023* (2013.01); *G01N 33/493* (2013.01);
(Continued)

(58) Field of Classification Search
CPC ...... G01N 1/40; G01N 1/4005; G01N 33/483; G01N 33/487; G01N 33/493;
(Continued)

(56) References Cited

U.S. PATENT DOCUMENTS 6,670,115 B1    12/2003    Zhang
2002/0030009 A1    3/2002    Lin
(Continued)

FOREIGN PATENT DOCUMENTS

WO    WO 2016/025726    2/2016
WO    WO 2022/150527    7/2022

OTHER PUBLICATIONS

International Search Report and Written Opinion for PCT/US2023/033729, mailed Mar. 12, 2024, 14 pages.

*Primary Examiner* — Benjamin R Schmitt
(74) *Attorney, Agent, or Firm* — Casimir Jones, S.C.; Rikki A. Hullinger

(57) ABSTRACT

Provided herein are devices and methods for isolation and detection of an analyte from a sample. In some embodiments, provided herein are devices and methods of use thereof for flow-based isolation and detection of analytes in a liquid sample, such as a urine sample, that leverage both substantially vertical and substantially lateral flow paths within the device to enable sensitive and specific detection of analytes from large sample volumes.

23 Claims, 52 Drawing Sheets

General Flow Path

(52) U.S. Cl.
CPC . *B01L 3/502715* (2013.01); *B01L 2300/0681* (2013.01); *B01L 2300/069* (2013.01); *G01N 2001/4088* (2013.01)

(58) Field of Classification Search
CPC .......... G01N 2001/4088; B01L 3/5023; B01L 3/502715; B01L 2300/0681; B01L 2300/069
See application file for complete search history.

(56) References Cited

U.S. PATENT DOCUMENTS

| | | | |
|---|---|---|---|
| 2003/0108949 A1* | 6/2003 | Bao | B01L 9/523 |
| | | | 435/7.1 |
| 2005/0214951 A1* | 9/2005 | Nahm | G01N 33/54388 |
| | | | 436/514 |
| 2007/0031978 A1* | 2/2007 | Quinlan | G01N 33/521 |
| | | | 436/514 |
| 2022/0118448 A1* | 4/2022 | Bula | A61B 10/007 |

* cited by examiner

Test Cap

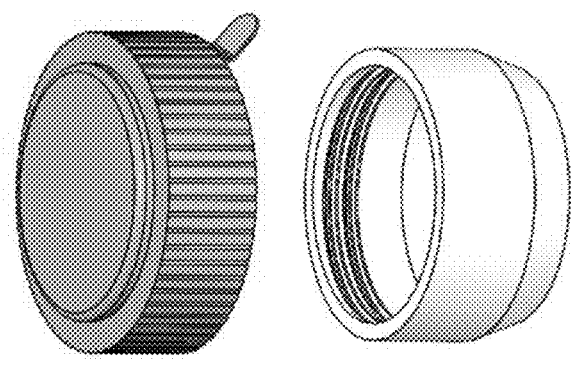
After urine flows,
device is turned over
and opened
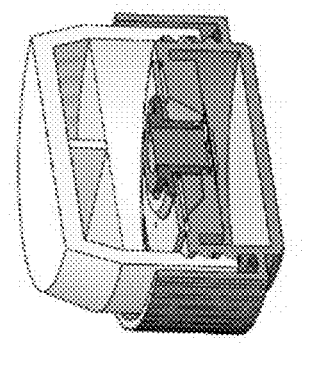
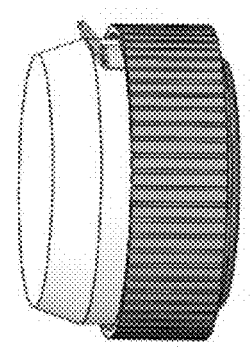
Cup closed, flipped
and urine flows
through filter inside
FIG. 15A
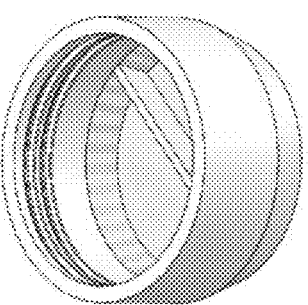
Urine poured into
cup with reagents

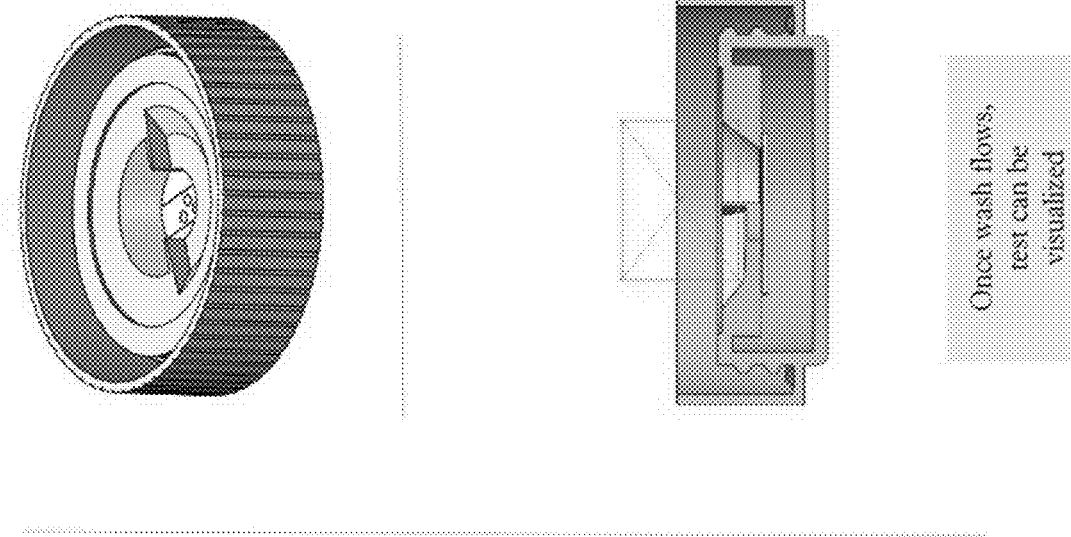
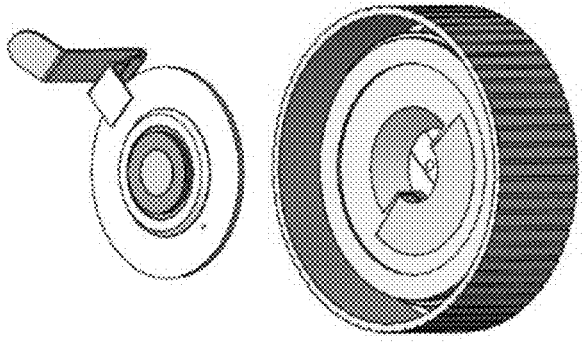
Once wash flows, test can be visualized
Filter layer is separated from test layer, releasing wash
FIG. 15B

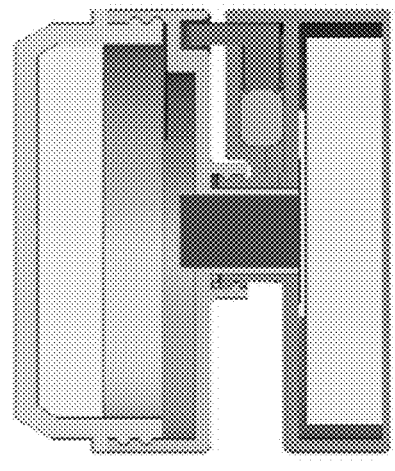
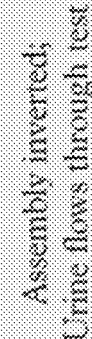
Assembly inverted; Urine flows through test
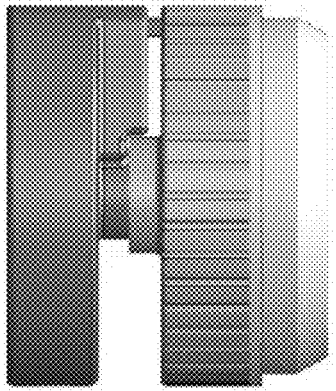
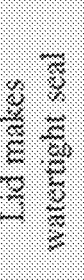
Lid makes watertight seal
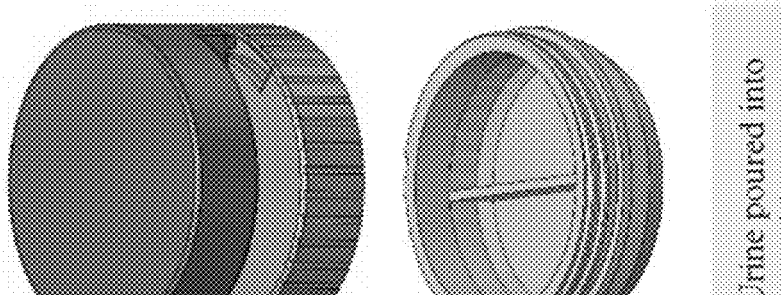
Urine poured into cup with reagents
FIG. 16A Reader placed on
male luer Plunger expels
wash capsule Cap removed from adaptor;
Filter + adaptor remain on cup

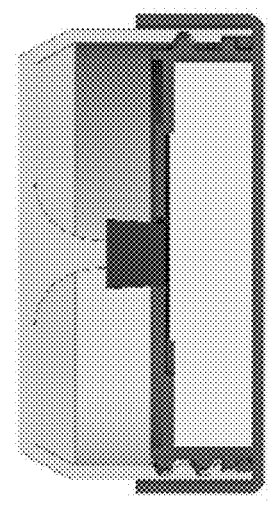
Assembly inverted; Urine flows through test
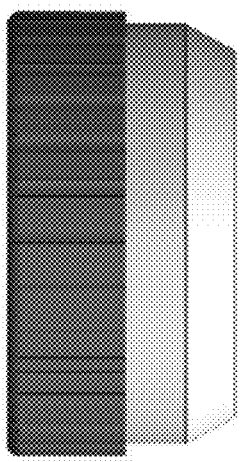
Lid makes watertight seal
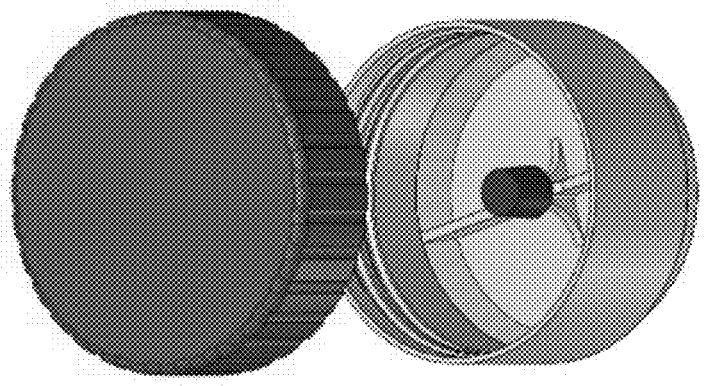
Urine poured into cup with reagents
FIG. 17A

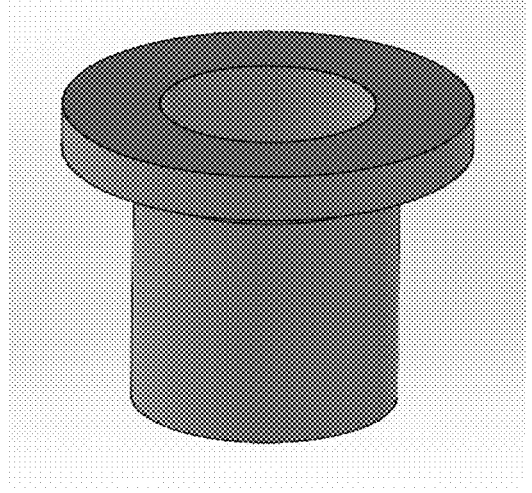
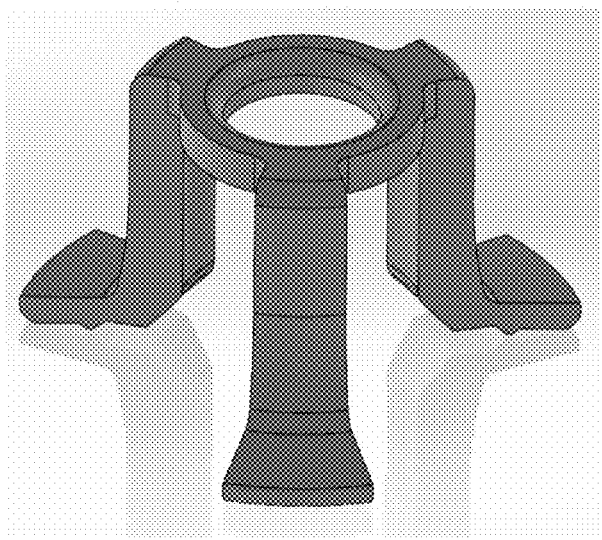
FIG. 17C

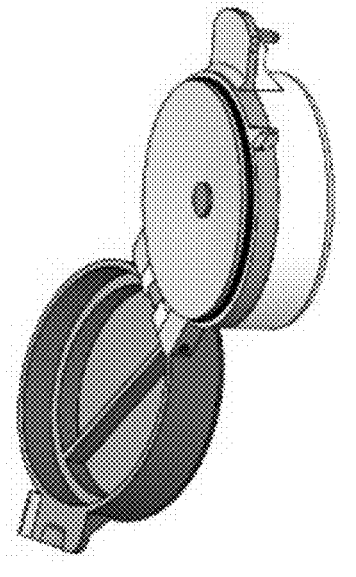
After urine flows, device is turned over and opened
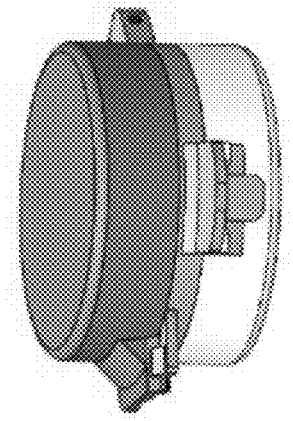
Cup closed, flipped and urine flows through filter inside
FIG. 18A
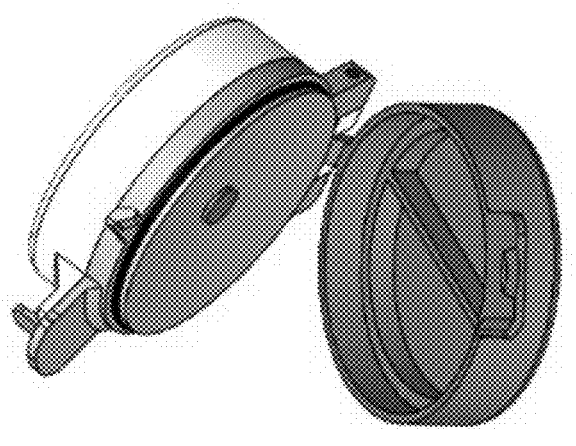
Urine poured into cup with reagents

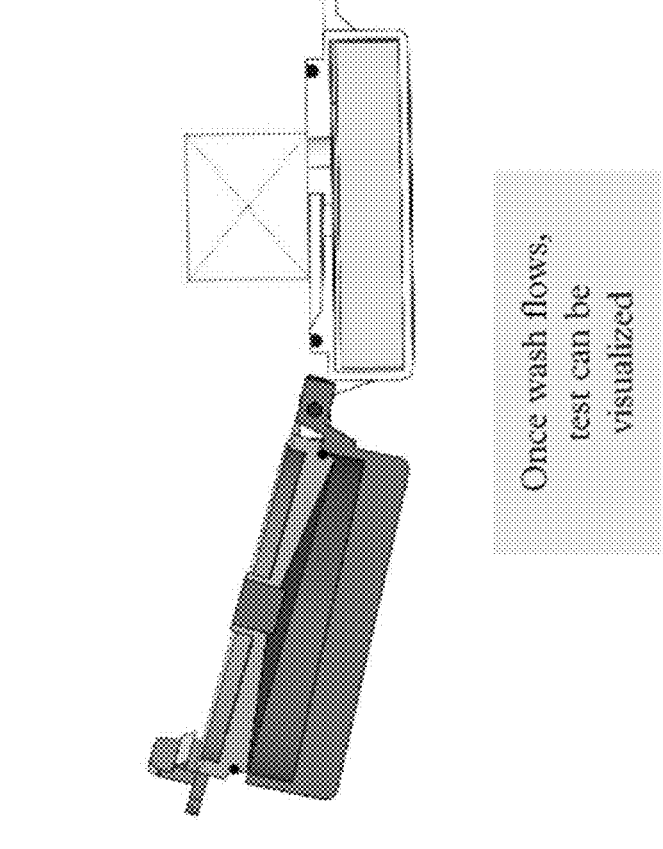
Once wash flows, test can be visualized
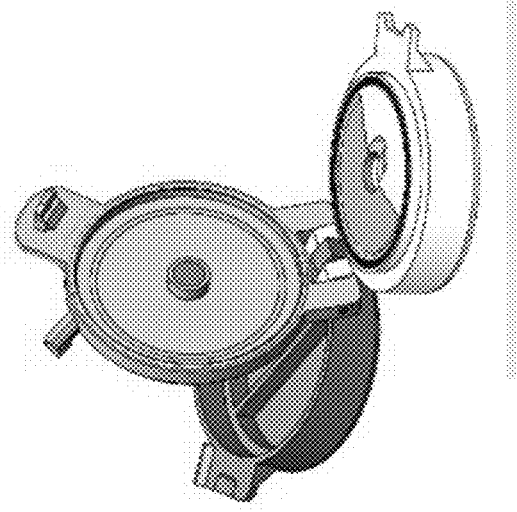
Filter layer is separated from test layer, releasing wash
FIG. 18B

D 3D Printed Prototype

C CAD Design

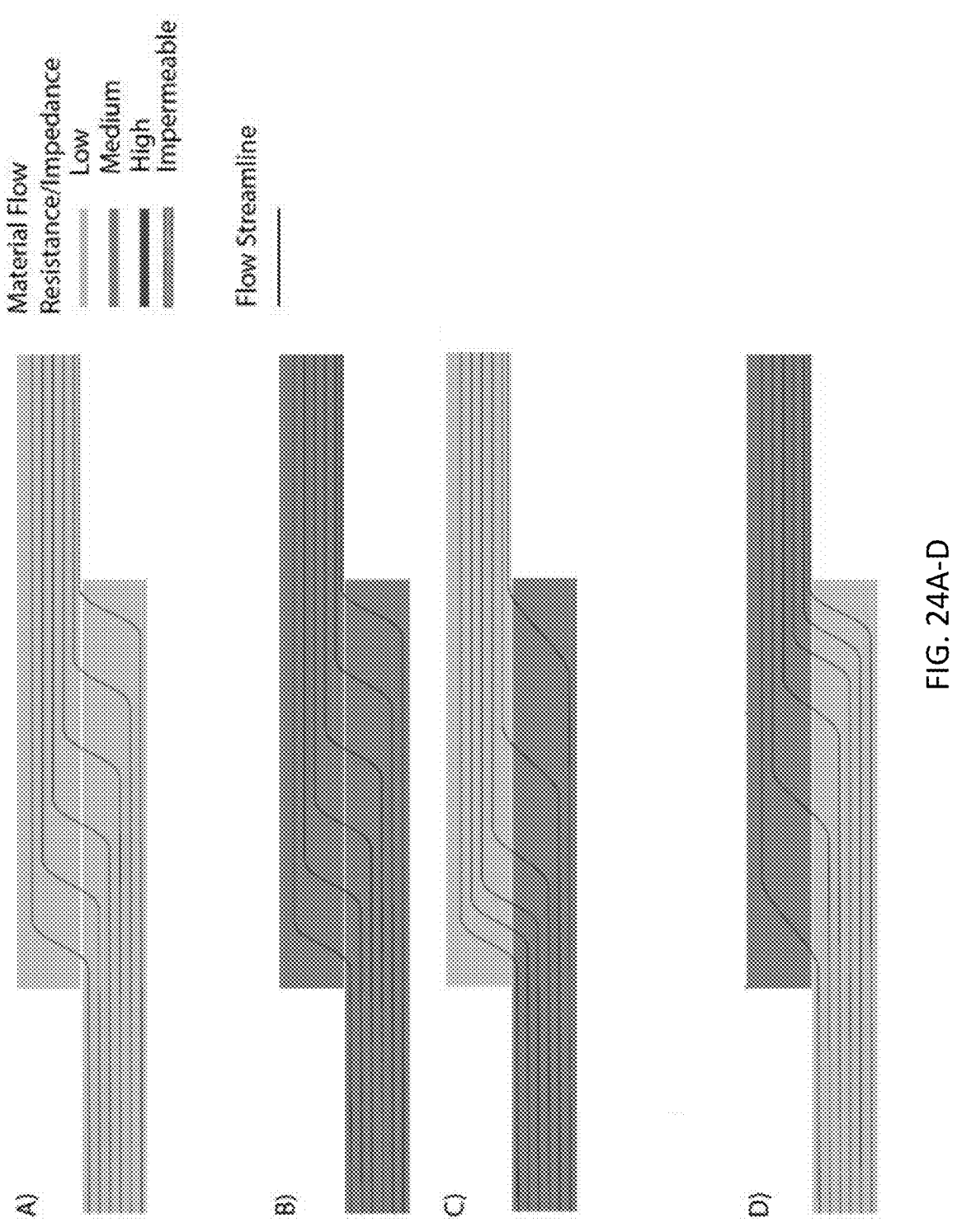
FIG. 24A-D

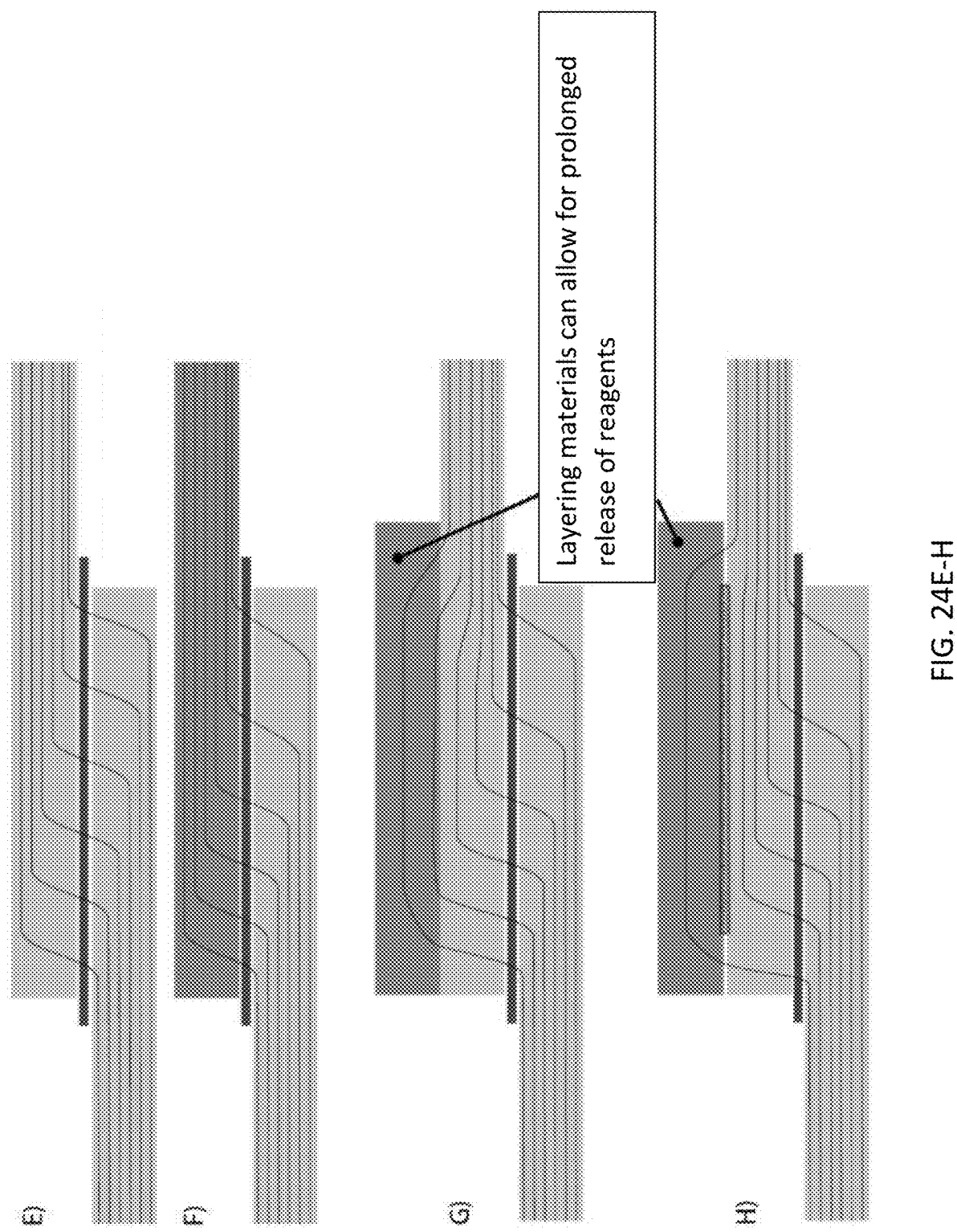
FIG. 24E-H

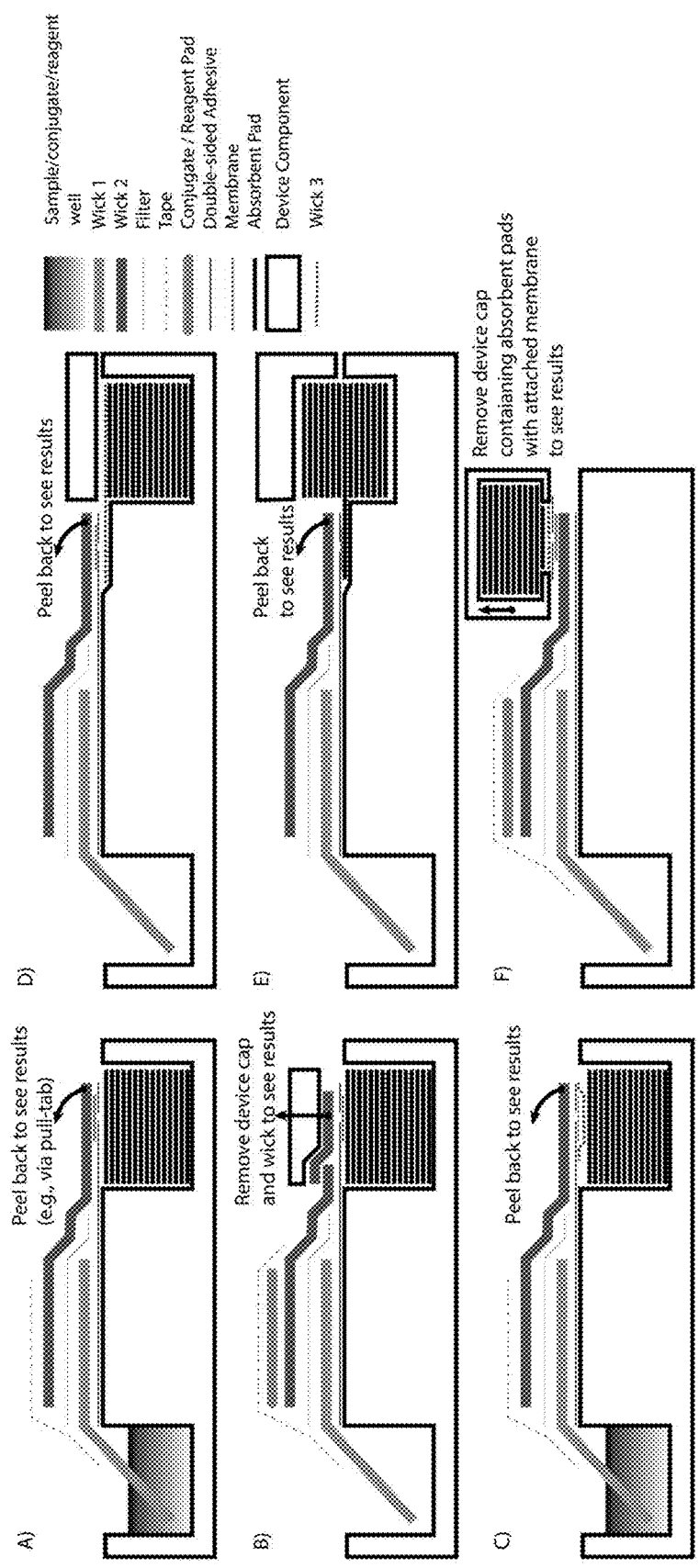
FIG. 25A-F

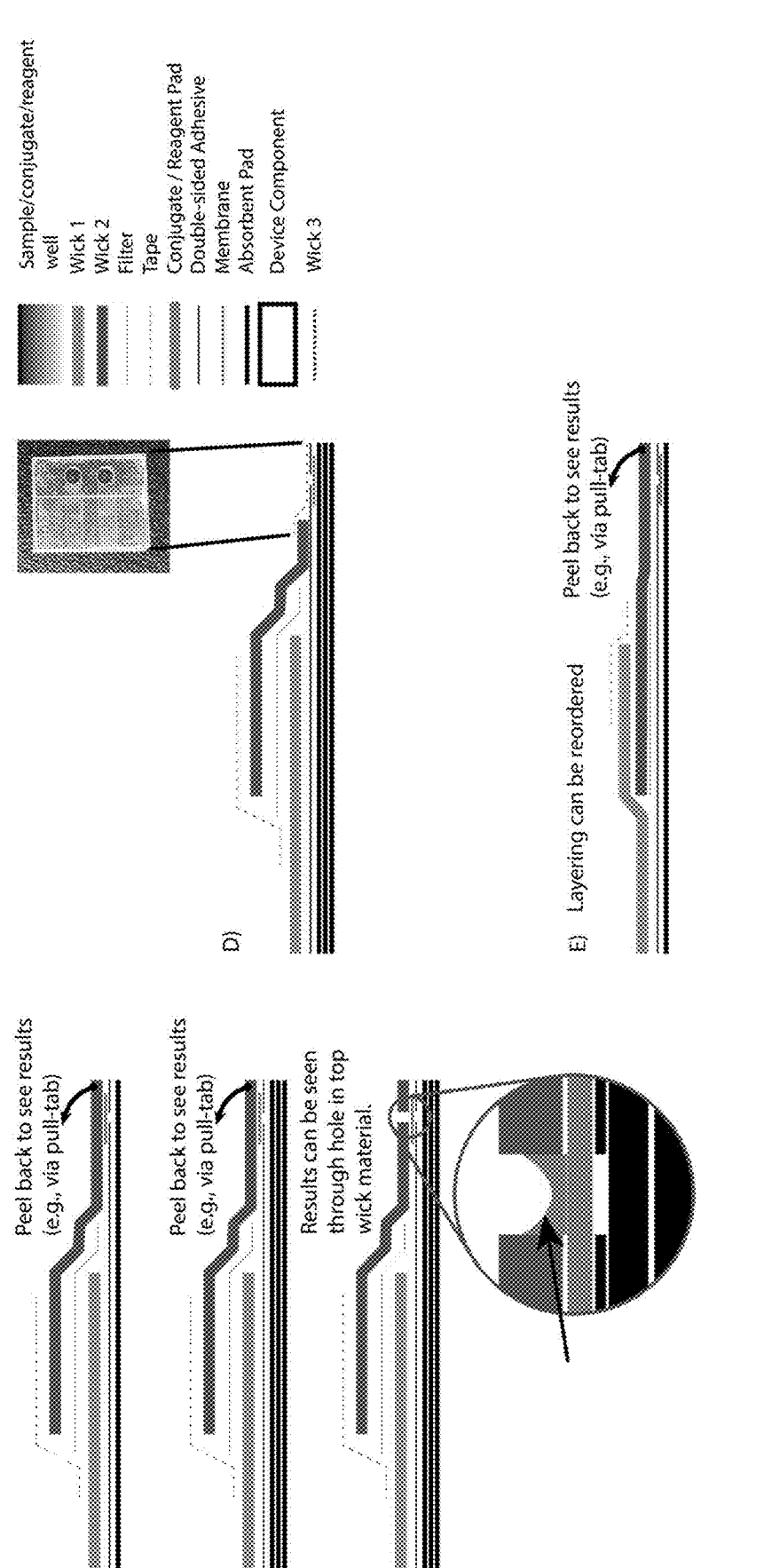
FIG. 26A-E

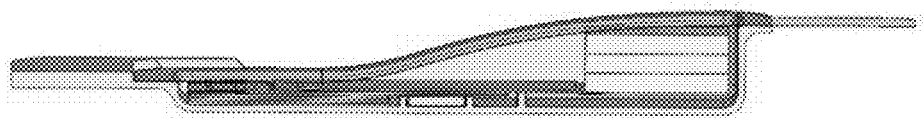
FIG. 28A
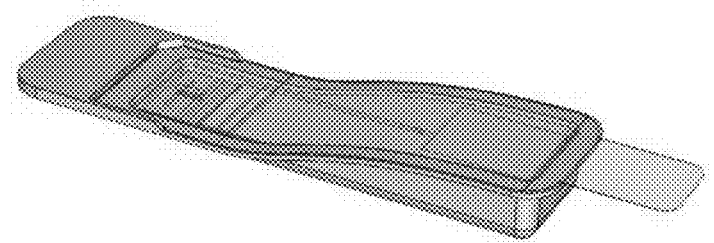
FIG. 28B
FIG. 28C                                        FIG. 28D

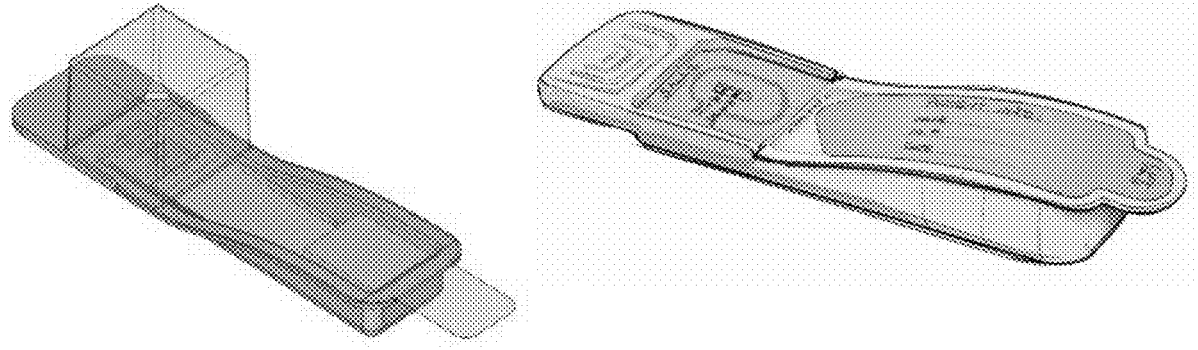
FIG. 28E                              FIG. 28F

| Sample # | Sample Location | HIV Status | Initial MSD [LAM] | |
|---|---|---|---|---|
| 21 | Peru | HIV- | 160.9 | TB + / MSD + |
| 22 | South Africa | HIV+ | 239.7 | |
| 4 | South Africa | HIV + | 20,000 | |
| 17 | Peru | HIV- | 9.6 | TB + / MSD - "Undetectable" |
| 18 | South Africa | HIV- | 5.8 | |
| 19 | South Africa | HIV+ | 1.1 | |
| 20 | Peru | HIV- | NA | |
| 9 | South Africa | HIV+ | 14.7 | TB - / MSD - True Negatives |
| 10 | Peru | HIV- | 6.8 | |
| 11 | Peru | HIV- | ND | |
| 12 | South Africa | HIV- | ND | |
| 13 | South Africa | HIV+ | ND | |
| 14 | South Africa | HIV- | ND | |

FIG. 30C

A) Protein Removal

B) Loss of LAM

DEVICES AND METHODS FOR VERTICAL FLOW-BASED DETECTION OF ANALYTES

STATEMENT REGARDING RELATED APPLICATIONS

This application claims priority to U.S. Provisional Patent Application No. 63/410,389, filed Sep. 27, 2022, the entire contents of which are incorporated herein by reference for all purposes.

STATEMENT OF GOVERNMENT SUPPORT

This invention was made with government support under grant number 4R44HD101201-02 awarded by the NIH and under OPP1152864 Awarded by the Gates Foundation. The government has certain rights in the invention.

FIELD

Provided herein are devices and methods for isolation and detection of an analyte from a sample. In some embodiments, provided herein are devices and methods of use thereof for vertical flow-based isolation and detection of analytes in a liquid sample, such as a urine sample. The devices and methods provided herein permit sensitive and specific detection of analytes from large sample volumes.

BACKGROUND

Lateral flow assays are commonly used to detect analytes in a liquid sample. However, lateral flow assays are limited by the inability to flow a large volume across the assay. Vertical flow assays have been used, however achieving a high sensitivity using a vertical flow assay is a challenge. Moreover, large sample volumes frequently lead to clogging of the vertical flow assay, thereby limiting their efficacy and sensitivity. Sample components (e.g. contaminants) can interfere with downstream detection of the desired analyte, and as such methods for removing contaminants from samples are also needed. Accordingly, what is needed are simple, low cost solutions to achieve sensitive, specific vertical flow assays that can be used with large sample volumes and that effectively remove contaminants from samples, such as urine samples.

SUMMARY

In some aspects, provided herein are devices. In some embodiments, provided herein is a device for detecting one or more analytes in a liquid sample. In some embodiments, the device comprises a plurality of porous materials. In some embodiments, the device is configured such that a liquid sample flows substantially vertically through some or all of the porous materials of the device. In some embodiments, the device is configured such that a liquid sample flows substantially vertically through some of the porous materials and substantially laterally through other porous materials of the device. In some embodiments, the device comprises a filter system comprising one or more filter components, a porous membrane containing one or more capture moieties held within a defined capture region of the porous membrane, and at least one absorbent pad. In some embodiments, the device is configured such that after flowing through various components of the device the liquid sample subsequently flows into the at least one absorbent pad. In some embodiments, the device is configured such that a liquid sample flows first through a filter system prior to contacting the porous membrane. The filter system can perform any type of filtration, including but not limited to size-based filtration, capture/affinity-based filtration, or both. In some embodiments, the device is configured such that a liquid sample flows first substantially vertically through or substantially laterally through the filter system prior to flowing through the porous membrane. In some embodiments, the device also comprises non-porous structures (e.g., microchannels, barriers, adhesives, and/or reservoirs) that may interact or interface with porous materials of the device to aid fluid transport, handling, containment, storage, pooling etc. In some embodiments, porous and/or non-porous materials may or may not contain reagents (wet, dry, semi-dry, viscous, active, inert, stable, labile, or otherwise). For example, one or more materials within the device can contain buffers, beads, powders, surfactants, vapor deposited reagents, and the like.

In some embodiments, the device is configured such that the liquid sample flows in a gravity-assisted or acceleration-assisted manner, wherein the liquid sample passes through the filter system prior to contacting the porous membrane, and subsequently flows through the porous membrane and into the at least one absorbent pad. In some embodiments, the liquid sample flows substantially vertically through device components (e.g. through the filter system and through a porous membrane). In some embodiments, the liquid sample flows substantially vertically through device components (e.g. through the filter system and through the porous membrane) in a gravity-assisted or acceleration-assisted manner. In some embodiments, the liquid sample flows substantially laterally through device components (e.g. through the filter system and through the porous membrane) in an acceleration-assisted manner (e.g., via centrifugation). In some embodiments, the device also comprises non-porous structures (e.g., microchannels and/or reservoirs) that may interact or interface with porous materials of the device to aid fluid transport, handling, containment, storage, pooling etc.

In some embodiments, the porous membrane comprises two opposite sides, wherein each of the two opposite sides comprises at least one permeable region that allows passage of the liquid sample through the permeable region. In some embodiments, the liquid sample flows through the at least one permeable region on each of the two opposite sides at least once before flowing into the absorbent pad.

In some embodiments, the porous membrane further contains one or more detection moieties. In some embodiments, the porous membrane further comprises one or more control regions. In some embodiments, the control regions comprise capture moieties.

In some embodiments, the device comprises at least one component to direct flow of liquid to and/or through the capture region(s) and the control region(s), if such regions are present in the porous membrane. In some embodiments, a component to direct flow of liquid through a region of the porous membrane is present, even in the absence of a capture or control region and can be used to influence flow rate of liquid through the device.

In some embodiments, the filter system comprises at least two filter components, wherein each component comprises pores and/or capture moieties for removal of contaminants. In some embodiments, each component comprises pores for removal of contaminants, and the size of the pores decreases incrementally from the first component to contact the liquid sample to the last component to contact the liquid sample. In some embodiments, capture moieties in the filter component may capture specifically (e.g., similar to an antibody and antigen) or non-specifically (e.g., a protein-binding membrane).

In some embodiments, the filter system comprises a nylon membrane. For example, in some embodiments the filter system comprises at least one filter component, wherein the at least one filter component is a nylon membrane. In some embodiments, the nylon membrane is a positively charged nylon membrane, a negatively charged nylon membrane, a neutral nylon membrane, or an amphoteric nylon membrane. In some embodiments, the nylon membrane is a positively charged nylon membrane.

In some embodiments, more than one filter system or filter component (e.g., 2, 3, or 4) is used. In some embodiments, the composition of each filter system or each filter component (e.g. layer) is the same. In some embodiments, the composition of each filter system or each filter component is different. In some embodiments, one or more filter systems or filter components within a filter system are the same and one or more filter systems or filter components within a filter system are different from each other. For example, in some embodiments the sample passes through two filters of the same pore size followed by a filter with smaller pore size). In some embodiments, different fluid streams are filtered by separate filter systems/filter components within the same device. For example, in some embodiments the device comprises one positively charged nylon membrane to filter sample applied to a sample port and a second neutral nylon membrane to filter running buffer added to a running buffer port for rehydrating conjugate prior to filtered sample and filtered running buffer merging into a single flow stream.

In some embodiments, the device further comprises a housing body. In some embodiments, the porous membrane and the at least one absorbent pad are contained within the housing body, and the housing body comprises an opening to permit entry of the liquid sample into the housing body. In some embodiments, the filter system is housed within the housing body, such that the filter system is directly proximal to the opening of the housing body. In some embodiments, the housing body comprises plastic. In some embodiments, the housing body comprises bio-derived material(s) such as wood pulp and/or bamboo pulp. In some embodiments, the housing body comprises thin film(s) and/or adhesive(s). In some embodiments, the housing body comprises a first component (e.g. a top component) and a second component (e.g. a bottom component) which removably connect to each other to form a splash-resistant or water-resistant or waterproof seal. In some embodiments, the first component (e.g. the top component) comprises an opening to permit entry of the liquid sample into the housing body. In some embodiments, the first component (e.g. the top component) comprises an opening or clear viewing window to view at least one test indicator and/or at least one control indicator.

In some embodiments, the device further comprises a component to direct flow of the liquid sample into an opening, such as a funnel. In some embodiments, the component (e.g. funnel) holds at least 15 mL of liquid sample. In some embodiments, the filter system is housed within the funnel.

In some embodiments, the device further comprises at least one wicking component. In some embodiments, the device further comprises at least one component to prevent the liquid sample from circumventing the filter system.

In some embodiments, provided herein is a device for detecting one or more analytes in a liquid sample comprising a filter system comprising one or more filter components, a porous membrane containing one or more capture moieties held within a defined capture region of the porous membrane, and at least one wicking component. In some embodiments, the device is configured such that a liquid sample is wicked through a portion of the device substantially against the force of gravity, and subsequently contacts the porous membrane. For example, the liquid sample can be wicked through at least a portion of the filter system substantially against the force of gravity, and subsequently contacts the porous membrane. In some embodiments, the porous membrane further contains one or more detection moieties.

In some embodiments, the device additionally comprises at least one absorbent pad. In some embodiments, the liquid sample is wicked through a portion of the device substantially against the force of gravity, and subsequently flows through the porous membrane and into the at least one absorbent pad.

In some embodiments, at least a portion of the at least one wicking component is positioned between the filter system and the porous membrane, such that the liquid sample is wicked through the filter system and onto the porous membrane. In some embodiments, at least a portion of the at least one wicking component is positioned above the porous membrane, such that the liquid sample is wicked through the filter system and the porous membrane. In some embodiments, at least a portion of the at least one wicking component is positioned between the porous membrane and the absorbent pad, such that the liquid sample is wicked through the filter system and the porous membrane and into the absorbent pad. In some embodiments, at least a portion of the at least one wicking component is positioned beneath the filter system, such that the liquid sample is wicked onto the filter system. In some embodiments, the device comprises at least two wicking components.

In some embodiments, the filter system comprises at least two filter components, wherein each component comprises pores and/or capture moieties for removal of contaminants. In some embodiments, each component comprises pores for removal of contaminants, and the size of the pores decreases incrementally from the first component to contact the liquid sample to the last component to contact the liquid sample.

In some embodiments, the filter system comprises a nylon membrane. For example, in some embodiments the filter system comprises at least one filter component, wherein the at least one filter component is a nylon membrane. In some embodiments, the nylon membrane is a positively charged nylon membrane, a negatively charged nylon membrane, a neutral nylon membrane, or an amphoteric nylon membrane. In some embodiments, the nylon membrane is a positively charged nylon membrane.

In some embodiments, the porous membrane further comprises a control region. In some embodiments, the device additionally comprises at least one component to direct flow of liquid to specific regions of the porous membrane such as any capture and/or control region(s) that may be present in the porous membrane.

In some embodiments, the device further comprises a housing body. In some embodiments, the filter system and the porous membrane are contained within the housing body, and the housing body comprises an opening to permit entry of the liquid sample into the housing body. In some embodiments, the housing body comprises a top component and a bottom component which removably connect to each other to form a water-resistant or waterproof seal. In some embodiments, the bottom component comprises a sample collection cup. In some embodiments, the top component comprises a cap. In some embodiments, the filter system and the porous membrane are housed within the cap. In some embodiments, the wicking component and the absorbent pad, if present in the device, are housed within the cap.

In some aspects, provided herein is a device for detecting one or more analytes in a liquid sample comprising a sample collection cup, a cap, and a filter system comprising one or more filter components. In some embodiments, the cap comprises a porous membrane containing one or more capture moieties held within a defined capture region of the porous membrane, and at least one absorbent pad. In some embodiments, the cap and the cup removably connect to each other to form a water-resistant or waterproof seal.

In some embodiments, the porous membrane further contains one or more detection moieties.

In some embodiments, after connecting the cap to the cup, the device is flipped such that the liquid sample flows in a gravity-assisted manner from the cup into the cap. In some embodiments, the liquid sample passes through the filter system prior to contacting the porous membrane, and subsequently flows through the porous membrane and into the at least one absorbent pad. In some embodiments, the porous membrane further comprises a control region. In some embodiments, the device further comprises at least one component to direct flow of liquid to the capture region and the control region, if present in the porous membrane. In some embodiments, the device comprises at least one component to prevent the liquid sample from circumventing the filter system, such as one or more sealing gaskets or gap geometry to avoid the possibility of capillary action along and between component walls.

In some embodiments, the filter system comprises at least two filter components, wherein each component comprises pores and/or capture moieties for removal of contaminants. In some embodiments, each component comprises pores for removal of contaminants, and the size of the pores decreases incrementally from the first component to contact the liquid sample to the last component to contact the liquid sample.

In some embodiments, the filter system comprises a nylon membrane. For example, in some embodiments the filter system comprises at least one filter component, wherein the at least one filter component is a nylon membrane. In some embodiments, the nylon membrane is a positively charged nylon membrane, a negatively charged nylon membrane, a neutral nylon membrane, or an amphoteric nylon membrane. In some embodiments, the nylon membrane is a positively charged nylon membrane.

In some embodiments, the least one absorbent pad is immediately proximal to the porous membrane.

In some embodiments, the filter system is housed within the cap. In some embodiments, the filter system is housed within the sample collection cup. In some embodiments, the filter system is an intermediate component between the sample collection cup and the cap. In some embodiments, the filter system is detachable.

In some embodiments, the cap further comprises a wash buffer retained within a reservoir. In some embodiments, the cap comprises the reservoir housing the wash buffer and a removable seal, wherein removal of the seal releases the wash buffer from the reservoir.

In some aspects, provided herein is a device wherein flow of a liquid sample through at least a portion of the device is substantially lateral (i.e., substantially in the plane of a material layer or interface), and flow of the liquid sample through at least a portion of the device is substantially vertical (i.e., substantially perpendicular to the plane of the material layer or interface). For example, in some embodiments provided herein is a device comprising a plurality of porous materials, wherein flow of a liquid sample through at least one of the plurality of porous materials is substantially vertical and flow of the liquid sample through at least one of the plurality of porous materials is substantially lateral. Such a device is also referred to herein as a "hybrid" device. Furthermore, materials and/or components layers or interfaces are not constrained to be in a horizontal or vertical orientation but can be any orientation, including multiple different orientations within the same device (e.g., a substrate supporting material layers can curve, roll, bend, fold, and twist to create multiple orientations of components and layers; or a wick material layer may extend beyond a supporting substrate and be curved, bent, rolled, folded, or twisted to provide different functionalities for different applications). In other words, flexibility (including stretching) or inflexibility of the materials and components is recognized as potentially advantageous and does not place restrictions on the interpretation of substantially lateral/vertical or planar/perpendicular flow.

In some embodiments, provided herein is a device comprising a first wicking component and a second wicking component separated by a filter system comprising one or more filter components, a porous membrane containing one or more capture moieties held within a defined capture region of the porous membrane, and at least one absorbent pad. In some embodiments, the device is configured such that a liquid sample flows from the first wicking component to the filter system, through the filter system to the second wicking component, from the second wicking component onto the porous membrane, and subsequently passes from the porous membrane into the at least one absorbent pad. In some embodiments, the flow of the liquid sample through at least a portion of the first wicking component and/or at least a portion of the second wicking component is substantially lateral, and the flow of the liquid sample through the filter system is substantially vertical. In some embodiments, the flow of the liquid sample through a portion of the first wicking component and through a portion of the second wicking component is substantially lateral. In some embodiments, the device comprises a junction wherein a portion of the first wicking component, a portion of the filter system, and a portion of the second layer are stacked vertically with respect to one another, such that the flow of liquid sample through the junction is substantially vertical or perpendicular to the local plane or interface of the materials.

In some embodiments, the porous membrane further contains one or more detection moieties. In some embodiments, the porous membrane further comprises a control region.

In some embodiments, the device comprises at least one component to direct flow of liquid to the capture region and the control region, if present in the porous membrane.

In some embodiments, the filter system comprises at least two filter components, wherein each component comprises pores and/or capture moieties for removal of contaminants. In some embodiments, each component comprises pores for removal of contaminants, and the size of the pores decreases incrementally from the first component to contact the liquid sample to the last component to contact the liquid sample.

In some embodiments, the filter system comprises a nylon membrane. For example, in some embodiments the filter system comprises at least one filter component, wherein the at least one filter component is a nylon membrane. In some embodiments, the nylon membrane is a positively charged nylon membrane, a negatively charged nylon membrane, a neutral nylon membrane, or an amphoteric nylon membrane. In some embodiments, the nylon membrane is a positively charged nylon membrane.

In some aspects, the devices described herein are used in methods of detecting one or more analytes in a sample.

In some aspects, provided herein is a method of detecting one or more analytes in a liquid sample. In some embodiments, the method comprises applying the liquid sample to the device of any one of the preceding claims, passing the liquid sample through the filter system and onto the porous membrane within the device, such that the analyte, if present in the sample, binds to the one or more capture moieties held within the porous membrane, and detecting the one or more analytes. In some embodiments, one or more detection moieties are present within the device and/or are added to the device such that the one or more detection moieties binds to the analyte, thereby producing a detectable signal within the defined capture region of the porous membrane. In some embodiments, the one or more detection moieties are contained within the porous membrane. In some embodiments, the one or more detection moieties are added to the liquid sample prior to applying the liquid sample to the device. In some embodiments, detecting the one or more analytes comprises assessing the detectable signal within the defined capture region.

In some embodiments, the device housing and/or other device components are chosen to be constructed from materials that produce fewer or less hazardous materials when incinerated (e.g., cellulose-based vs. polypropylene).

In some embodiments, the wicking component(s) of the device can be entirely enclosed within a housing that has a resealable cover that is resistant to spilling of excess fluid and/or odor while providing access for adding sample fluid and/or equalization of air pressure between the inside and outside of the device. In some embodiments, the wick component is configured with the ability to hinge (e.g., a wick layer held down at one end with tape or a fluid transport layer held down with tape at one end with the other end connected to wick material). Such a hinge can be used to allow the resealable cover to be opened, the wick to be pivoted out of the housing such that the wick can be dipped into a sample without wetting some of other components and pivoted back into the housing, and the cover to be resealed. Similarly, the hinging wick can be left in its original position upon opening the resealable cover, allowing sample to be directly poured on the wick followed by resealing of the cover. In some embodiments, the wick material has geometry (e.g., a recessed region within the wick), to facilitate more rapid absorption of fluid upon pouring of the sample.

Any of the devices described herein may comprise one or more microfluidic channels. In some embodiments, one or more microfluidic channels are used to interface with porous materials as a means to direct fluid to desired regions of the porous membrane. In some embodiments, the device comprises one or more microfluidic channels that transport the liquid sample to the capture region of the porous membrane. In some embodiments, the device comprises one or more microfluidic channels that transport the liquid sample to the capture region of the porous membrane, and one or more microfluidic channels that transport the liquid sample to the control region of the porous membrane. In some embodiments, the microchannel(s) is/are clear, providing the ability to directly view potential test and/or control results/indicators. In some embodiments, the microfluidic channel has a hole exposed to atmospheric pressure, providing a means to equalize pressure between the inside and outside of the housing of the device when sealed while minimizing the release of potential sample odors through the small nature of the channel. In some embodiments, the microfluidic channel has a hole exposed to atmospheric pressure to facilitate capillary filling of the channel with liquid sample by allowing release of potentially trapped air/gas.

BRIEF DESCRIPTION OF THE DRAWINGS

FIG. 3 shows UV absorption at 230 and 290 nm. FIG. 4 shows fluorescence measurements with blue and UV excitation LEDs normalized to unfiltered urine (UrineC). Different fluorescence and absorbance signatures indicate how different filters can have different impacts on the filtered composition of the urine that could then impact the ability of large sample volumes to be processed through the membrane of the device.

FIG. 7A shows this embodiment, where the device is unsealed. The red arrow in the figure shows points to the empty receiving hook. FIG. 7B shows this embodiment, where the device is sealed by sliding the latch into the receiving hook. A red arrow in the figure points to the latched receiving hook. In these images, the top component (e.g. the lid) further comprises additional grips that allow the user to apply adequate torque to slide the latch into the receiving hooks.

FIG. 14A shows a device wherein a peel off filter system (e.g. filter cartridge) is used to allow the user to remove the urine filter after use. FIG. 14B shows a device wherein an intermediate component is used between the cup and cap to house the filter system. The intermediate component initially starts with the cap, the cap is attached to the cup (e.g., via screw or snap on mechanism), and when the user applies force to remove the cap, the intermediate filter component remains with the cup while the cap comes off without any urine filters that would impede washing or imaging/reading of the membrane. FIG. 14C shows a "Mushroom design", which is a variation of FIG. 14B, where the filter component is fixed to the cup. Application of the cap seals the filter cartridge against the cap. Upon inverting the cup, fluid is then forced to travel through the filter to pass through the membrane. Being fixed to the cup initially, the filter remains with the cup after cap removal to avoid interfering with application of wash fluid or imaging/reading of the membrane. The filter cartridge/post could be a separate piece that fastens into the cup to facilitate manufacturing. Likewise, the post/filter cartridge could be made as two components as well to facilitate manufacturing. FIG. 14D shows a variation of FIG. 14B where hinges are used between the cup, intermediate filter component, and cap to help aid manipulation and separation of filter components from the cap.

FIG. 15A and FIG. 15B show additional drawings and steps that may be performed using a "peel-off" filter system as also shown in FIG. 14A. The system comprises a cap and a sample collection cup. The cap comprises the filter system. As shown in FIG. 15A, urine is poured into the cup, the cup is "closed" by attaching the cap to the cup, and the device is flipped over. The sample (in this instance, urine) flows through the filter inside the cap and into contact with the porous membrane containing the capture and detection moieties. FIG. 15B shows in this embodiment, the filter system may be removed from the cap following use. In this embodiment, removal of the filter system releases a wash buffer, which is employed to decrease background signal on the porous membrane containing the capture moieties. The wash buffer is held within the cap and kept within a reservoir when the filter system is present. Removal of the filter system releases the wash buffer. Once the wash buffer flows across the porous membrane, the membrane can be visualized to detect the presence or absence of the analyte(s) of interest.

FIG. 16A and FIG. 16B show additional drawings and steps that may be performed using a device wherein the filter system is housed in an intermediate component between the cup and the cap, such as a device described in FIG. 14B. As shown in FIG. 16A, the sample (e.g. urine sample) is poured into the sample collection cup. The cap, which initially comprises the intermediate component housing the filter system, is attached to the cup to form a watertight seal. The device is inverted such that the urine flows through the filter system and into contact with the porous membrane containing the capture and detection moieties. The porous membrane is housed within the cap. As shown in FIG. 16B, the cap is then removed from the intermediate component, which remains attached to the sample collection cup. The cap is now separated from the used filters. The porous membrane (held within the cap) may be washed, and results may be visualized. In this embodiment, the cap contains a reservoir containing wash buffer. The wash buffer may be deployed from the reservoir, such as by use of a plunger. Following wash, results may be visualized (e.g. the detection moieties may be assessed) and features of the device may facilitate registration of the reader on the device.

FIG. 17A and FIG. 17B shows additional drawings and steps that may be performed using a device wherein the filter system is a "mushroom design" fixed to the sample collection cup, as described in FIG. 14C. As shown in FIG. 17A, the sample (in this embodiment, urine) is poured into the sample collection cup. The cap comprises a membrane containing an opening that aligns with a corresponding opening in the filter. The membrane is impermeable except for at the opening. The cap is connected to the urine cup, thereby forming a seal. Application of the cap seals the filter system against the cap. The device is inverted. Upon inverting the cup, the urine sample is then forced to travel through the filter to pass through the membrane. As shown in FIG. 17B, the cap is then removed, and the filter system remains attached to the cup. A wash buffer may be added to the cap if desired to reduce background signal. The detection moieties may be visualized to detect the analyte of interest. FIG. 17C shows exemplary components that may be used to facilitate attachment of the filter to the sample collection cup. The top component can house wick and filter materials and rests within the central hole of the bottom component. FIG. 17C is designed to snap into the bottom of a traditional thermoformed condiment cup. The items of FIG. 17C could be manufactured as a single piece. The cups used here have a slight constriction in the diameter just above the bottom to allow the legs of the base to snap into place, using the restriction to hold the base in place, as shown in FIG. 17D, FIG. 17E, FIG. 17F, and FIG. 17G. The legs ensure that the filter remains centered relative to the NC membrane.

FIG. 17J shows the cross-sectional view and flow path of this embodiment.

FIG. 18A and FIG. 18B show additional drawings and steps that may be performed using a device wherein the filter system is an intermediate component between the sample collection cup and the cap. The cap, intermediate component, and the cup may be attached via a hinge mechanism. As shown in FIG. 18A, the sample (in this instance, urine) is poured into the sample collection cup. The cup is closed, such that the intermediate component is secured between the cup and the cap. The device is flipped over such that urine flows through the filter system within the intermediate component and into the cap, which contains the porous membrane housing the capture and detection moieties. After flow of urine, the device may be opened. For example, the sample collection cup and the intermediate component may be pulled away from the cap. As shown in FIG. 18B, in this embodiment, the device further comprises a wash buffer held within a reservoir. Removal of the intermediate component from the cap disrupts the seal of this reservoir, thereby releasing wash buffer onto the porous membrane within the cap. Detection of the analyte of interest can then be assessed, such as by visualizing the detection moieties.

FIG. 20A shows a cross sectional view of a filter cartridge showing the location of the nitrocellulose membrane, wick material, and large-diameter filter membrane. Other filtration materials can be used instead of, or alongside, the wick in the lower portion of the cartridge. FIG. 20B shows a cross sectional view of the filter cartridge showing the intended flow path through the spacers and filter membrane. Highlighted in red are gaps in the walls of the filter cartridge that prevent wetting and the potential for fluid to bypass the filter membrane by traveling along the walls of the cartridge. FIG. 20C shows the fully assembled filter cartridge as a CAD design and FIG. 20D shows a 3D-printed prototype, each are shown without any membranes or wicks. FIG. 20E shows a slightly different filter cartridge embodiment that utilizes a wetting barrier (e.g., double-sided adhesive tape as shown, or a hydrophobic barrier such as wax or hydrophobic membrane) to restrict/encourage flow through the filter instead of around the filter while also enabling a single-piece filter cartridge body. In the figure the wetting barrier is referred to as an "adhesive seal".

FIG. 21A shows results from three different membrane filters used with 20 total mL of urine. FIG. 21B shows results from an MCE membrane filter used with many different types of spacers and wicks with 15 mL of total urine.

FIG. 22A shows use of a wick instead of a funnel to provide fluid to the membrane while utilizing an absorbent pad to help drive flow through the system. FIG. 22B shows redistribution of wick and absorbent material relative to (FIG. 22A) to reduce pressure heads that would impede flow, creating a fountain-like flow path coming up through the middle and radiating outward and down. FIG. 22C shows a variant of FIG. 22B, where flow is wicked up to the membrane and transferred across to a region with absorbent material, effectively transporting away the fluid horizontally and again reducing pressure head that would impede flow. FIG. 22D shows use of a flow barrier on the membrane to direct flow to pass through specific regions of the NC membrane. This helps to concentrate localization/concentration of analyte on the membrane and would typically be co-registered with the locations of antibodies on the membrane intended for capture of analyte or conjugate material. Upon entering the membrane, the flow paths then disperse again as they wick into the adjacent absorbent material. FIG. 22E shows additional flow barriers that can be introduced to cause local transverse flows that can be used to reduce flow resistance compared to a traditional lateral flow assay by limiting transverse flow to just a short distance or to increase flow resistance relative to purely vertical flow. Fluid enters through the opening in the flow barrier, passes through the membrane material on its way to the exit hole in the lower flow barrier that is adjacent to absorbent material. Many alternating layers of permeable and impermeable layers can be utilized to create complex paths for tuning flow path and resistance to suit various needs. FIG. 22F shows a similar mechanism to FIG. 22E, wherein fluid can be directed through the membrane in a constrained transverse pattern but can enter and exit from the same side of the membrane. The relative position and orientation of all the discussed components can be reconfigured to operate in reverse directions (e.g., components of FIG. 22B) can be inverted to create an inverted fountain-like flow path). Likewise, such approaches can be leveraged with other mechanisms to drive flow such as with a gravity-assisted funnel design. Flow could also occur radially outward through the LFA membrane, entering at one point and exiting circumferentially upward, out the edge of the material or down through the material.

FIG. 23A is a schematic of the flow path through the nitrocellulose with a spotted test and control line. Here a tape barrier directs flow through the nitrocellulose test and control zones. As the gap between the top and bottom tape becomes larger, flow rate increases, residence time decreases, and signal decreases. FIG. 23B shows results of an assay where 1 ng/mL LAM was run through the VFA using the gravity fed funnel system and the wick format. FIG. 23C shows images of the nitrocellulose after running the VFA.

FIG. 24A, FIG. 24B, FIG. 24C, FIG. 24D, FIG. 24E, FIG. 24F, and FIG. 24G show illustrations of different methods for structuring or designing flow paths to alter the timing of reagent release of reagents within components of the device. Fluid flow as materials become wet (e.g. during wetting) can be different from flow that occurs after they are wet (e.g. after wetting). This figure largely describes flow after wetting that is typically dictated by fluid viscosity and resistance of the material to fluid flow (e.g., typically materials with smaller pore sizes or less porosity have increased resistance to fluid flow). Depending upon the resistance to fluid flow, one can achieve different levels of perfusion in adjacent materials. If flow is sufficiently slow through one of the layers, transport of some reagents from one pad to the other may primarily be through diffusion instead of bulk fluid flow. Thus, engineering the resistance to fluid flow of the adjacent materials, and any potential associated flow barriers, can be used to tune the rate and profile of reagent delivery or mixing between layers. In some cases, longer term delivery of reagents is necessary when using a reagent pad that has a relatively small volume compared to the overall sample volume that must be treated or is flowing through an adjacent pad. In this figure, flow streamlines that are more spaced apart indicate slower flow whereas streamlines spaced more closely together indicate faster flow. Sequencing and mixing different configurations is also possible. As shown in FIG. 24A and FIG. 24B, at connections between pads with similar resistance, flow through the interface is substantially vertical and uniformly distributed across the junction/interface. As shown in FIG. 24C and FIG. 24D, slower displacement of fluid allows for prolonged introduction of reagents initially dried within the slower flow regions of the higher resistance pad into downstream components. Flow is biased towards the paths of least resistance through the system. As shown in FIG. 24E, flow proceeds substantially vertically through the high resistance filter membrane inserted between the top and bottom components. As shown in FIG. 24F, the high resistance membrane reduces the flow bias across the junction/interface due to uniformly increased overall resistance. As shown in FIG. 24G and FIG. 24H, layering materials can also allow for prolonged release of reagents within materials as illustrated, with the median resistance material on top. Further, high-resistance or impermeable barriers can be added to make release of the reagents more consistent over time by creating a substantially "first-in-first out" flow path through the top pad. As shown in FIG. 24H, the high resistance membrane reduces the flow bias across the junction/interface due to uniformly increased overall resistance.

FIG. 25A-F show a roll-based approach to manufacturing an exemplary device described herein. (FIG. 25A) A wick communicates with a sample reservoir, drawing fluid into the device. Capillary action draws fluid up through a filter into a second wick. The second wick brings filtered sample into communication with the membrane. In this example, the membrane can be labeled for detection of analyte in the filtered sample. Absorbent pads draw fluid through the membrane (i.e., out of the sample reservoir). In some embodiments, the membrane is on a double-sided adhesive or a backing card or supporting layer. This supporting layer can have a hole for limiting flow through the membrane to a specific region of the membrane. A layer of tape can be used to keep layers in communication with each other. In this example, the secondary wick would need to be pulled back to reveal a visual test result. (FIG. 25B) Additional pressure can be added to the configuration with external structures (e.g., a snap on lid) to improve capillary action and flow into the absorbent pad(s). Likewise, the secondary wick could be made in two pieces, to allow the test rest to be revealed by removing a portion of the secondary wick instead of pulling and edge back to reveal the result. The second piece of the secondary wick could be attached to the structure providing pressure for capillary action (e.g., attached to the lid). Likewise, the membrane can be located above or below the double-sided adhesive or supporting layer for the device. (FIG. 25C) A third wick can also be used to provide better capillary action between components. In this example, the tertiary wick is added between the absorbent pad(s) and the membrane but could be added between any suitable components to improve wicking between layers. (FIG. 25D) In addition to using such a wick material to facilitate capillary action and conformance between layers, such material(s) can be used to transfer fluid horizontally as well to other regions of the device. In this example, the tertiary wick accepts fluid from the membrane and guides fluid horizontally where it can communicate vertically with absorbent pads to facilitate alternate absorbent pad configurations. (FIG. 25E) In this example configuration, use of a tertiary wick allows absorbent pads to be used both above and below a wick material without covering the membrane, increasing the rate of sample flow by allowing fluid to soak into absorbent pads both above and below the plane of the wick material (i.e., a ~2× increase in fluid flow). (FIG. 25F) In some configurations, some components are attached to a lid or structure that can provide force to improve contact between the absorbent pad(s) (and potential tertiary wick material(s)) and the membrane. Such a configuration would allow components to be removed with the lid/structure to view results when done. In the illustrated example, a generic conjugate or reagent pad can be added over the top of the secondary wick to "infuse" reagent into the flow stream. The resistance can be chosen according to FIG. 24 to achieve the desired "infusion" characteristics over time. Such a reagent reservoir could be incorporated onto any of the porous materials of the device (e.g., on the first wick to help condition sample prior to filtration). Likewise, any of the porous materials can be treated before, during, or after the assay for desired effect (e.g., drying of neutralization buffer into the first wick ensures that upon wetting with sample, the sample is brought to appropriate pH for binding with conjugate being infused by the generic conjugate/reagent pad, or the filter membrane could be pre-blocked and dried with protein such as BSA to avoid unwanted adsorption of analyte during filtration).

FIG. 26A-E demonstrate a roll-based approach to manufacturing the entirety of an exemplary device as described herein. (FIG. 26A) Use of a supporting layer for device construction with adhesive on both sides (e.g., a double-sided adhesive) allows components to be adhered to either the top side or bottom side of the supporting layer. Furthermore, "backing" layers or localized removal of a "backing layer" over either side of adhesive allows for selective adhesion of materials to different locations of the supporting layer. In this illustrated example, a double-sided adhesive is used as the supporting layer to enable roll-based construction of all the key components of the device. Depending on the wick layer dimensions a wick layer can accept a large range of input sample volumes. In some embodiments a wick layer of 70 mm length and 25 mm width can accept a sample of 7.5 mL, but can be scaled much larger or much smaller as needed. In this example, the wick layer brings sample into communication with a filter membrane. A secondary wick draws fluid through capillary action from the filter and into communication with a membrane for detection. An absorbent pad that is allowed to communicate with the membrane through a hole in the supporting layer (or extended beyond the supporting layer), draws fluid from the membrane and therefore the input sample wick. The supporting layer provides a fluid barrier to prevent fluid in the input wick from communicating directly with the absorbent pad underneath the supporting layer. Depending upon where the adhesive of the supporting layer is exposed, some of the layers may be able to separate from the supporting layer in some locations. For example, the absorbent layer can be fixed to the supporting layer near the membrane but allowed to separate from the supporting layer elsewhere. Likewise, the input wick can be allowed to separate from the supporting layer by simply fixing to the supporting layer near its downstream end, allowing the region of the wick where sample is added to separate from the supporting layer. Such mobility can provide advantages for user interaction. (FIG. 26B) In this example, multiple layers of absorbent pad are adhered to one another to triple the absorbent capacity of the device relative to using a single layer of adhesive. This can be done in a localized fashion with double-sided adhesive or with an external cassette for housing the device. (FIG. 26C) In this example, a hole is cut in the secondary wick that is generally aligned with the hole through the supporting layer. Such a hole allows visualization of the test result without needing to remove the secondary wick. Wetting of the secondary wick brings fluid into communication with the membrane test region. Wetting of the secondary wick also allows formation of a meniscus of fluid within the hole that can act to cover the test region of the membrane with fluid. Thus, while the secondary wick itself may not directly touch the test region of the membrane, such a hole can still bring fluid into direct communication with the test region without having to pass through the membrane in a lateral fashion first, before passing vertically through the membrane and into the absorbent pads. The size of this hole can depend upon the surface of the fluids. Further, different hole shapes can be used (square, tear dropped shape to encourage wetting, or some symbol to indicate the type of test region [e.g., test region or control region or multiplexed region 1, 2, and 3]). Similarly, the vertical cross section of the hole might be altered. For example the hole could be wider at the top and narrower at the bottom to provide better viewing. As shown in the zoomed in portion of FIG. 26C, the fluid can wet the area inside the hole to provide fluid directly over the test region (as indicated by the arrow). Further, this secondary wick layer could be constructed of multiple sublayers and provide a stepped diameter moving from top to bottom. (FIG. 26D) In this illustrated example, a microfluidic channel (also referred to herein as a "microchannel" or a "channel") is integrated over the top of the test region of the membrane. The microchannel can be constructed or treated to encourage capillary filling (e.g., made from glass or polystyrene or oxygen plasma treated to be superhydrophilic). The channel can be constructed from tape and or polymer films as well. For example, as illustrated, double sided adhesive cut away to create channels and overlaid with a clear polymer film can be laid on top of a device to integrate a microchannel into the device. Likewise, a supporting layer made of double sided adhesive can itself be cut and overlaid with polymer film to integrate a microchannel into the device. Integration of the microchannel allows sample to flow through the device without obstructing view of the test region, allowing the device to be monitored or read without any further manipulation of the device components. For example, in some embodiments a capillary microchannel (e.g. a tape-based capillary microchannel) wicks sample over the test region, facilitating both the flow of sample through the device and viewing of the result. The microchannel can also be made with materials other than tape (e.g. other films/adhesives). (FIG. 26E) This example illustrates that ordering of layers in this device is flexible. In other words, whether substantially vertical flow is occurring in a generally "upward" direction or "downward" direction is largely equivalent. Thus, filtering can be performed up (as in FIG. 26A)) or down as in this example (FIG. 26E) without impacting upstream or downstream components significantly. However, for example, if the input wick is extremely thick for holding a large amount of fluid, it may prove beneficial to have the input wick below the filter to avoid excess fluid on the wick from inadvertently dripping downward over the edges of the material if configured above the filter and secondary wick. Likewise, there may be an advantage from a manufacturing point of view to construct them in one order over another. For example, if the wick material is very thick and compressible, fragile thin materials (e.g., a filter membrane) may inadvertently tear during cutting. Therefore, configuration of the layers can be leveraged to improve manufacturing. Likewise, thick materials can introduce significant step changes in thickness that can encourage overlapping layers to delaminate or cause extra compression or gaps. In some cases, edge compression can be advantageous (e.g., compression can reduce pore size and locally improve capillary action or locally increase fluidic resistance). In some cases gaps can be disadvantageous (e.g., potentially reducing the cross-sectional area for vertical flow in a vertical flow section of the device). Thus, layer configuration may be chosen to improve performance at material overlaps (e.g. junctions).

FIG. 27A-E show examples of methods for introducing fluid to a device design that can be constructed largely via roll-based manufacturing. (FIG. 27A) Fluid can be pipetted directly onto a uniform layer of wick material. However, sometimes, if fluid introduction is too sudden, the material cannot accept the fluid as rapidly as it is being delivered. In such cases, cutting a hole in the wick material can provide a "reservoir" bounded by wick material that can accept more rapid fluid additions while containing fluid motion from the addition of fluid (e.g., "jets" of fluid) that might otherwise flow over the edge of a uniform wick material. In this example, a hole is added to the input wick material to accept rapid addition of sample via pipette. The example also illustrates that layers of the device do not need to be of the same width but may require modifications to traditional roll-based manufacturing (e.g., removal of excess material that was initially perforated after roll-based assembly or simple pick and place assembly over the top of a roll-based assembly process). (FIG. 27B-27C) These two illustrated examples demonstrate how introduction of fluid sample might be performed more easily when using a roll-manufactured device. FIG. 27B shows another illustrated example demonstrating that the device can also straddle the edge of a standard urine cup, wetting the input wick while keeping the absorbent pads dry. In this case, the cup is inserted between the absorbent pad and the supporting layer; however, it may be more beneficial to have the cup wall insert between the wick and the supporting layer. This keeps the supporting layer dry, allowing the device to be placed on a tabletop without fluid from the supporting layer to then wet the absorbent pad. Straddling the cup wall potentially eliminates the need for separate ladle structure while still allowing collection of a specific volume of input sample which is largely dictated by the amount of fluid initially absorbed by the input wick (e.g., the wick material will generally wet quickly compared to subsequent flow associated with filtration and detection allowing dipping of the wick to dictate the amount of volume sampled). In FIG. 27C, a ladle structure is shown with two cavities where the roll-manufactured device straddles the barrier between the two cavities. The absorbent pad of the device can be inserted into one cavity (i.e., right-hand portion of ladle as illustrated) while the rest of the device is inserted into the other (i.e., left-hand portion of ladle as illustrated). The ladle can then be dipped or scooped into the fluid sample to acquire a measured amount of fluid. After absorption of the sample into the wick material (and potentially other materials of the device), the ladle can be left in essentially any orientation as capillary forces hold the fluid within the materials of the device.

FIG. 28A-F show an exemplary device described herein. The device is created using roll-based manufacturing of many components. The device additionally comprises a hinged wick. (FIG. 28A) Cross section view of the device. (FIG. 28B) Isometric view of the device. The device comprises a bottom housing; absorbent pads; desiccant disc; roll-manufactured device with hinged wick, stack of wick materials for additional fluid capacity, large-area vertical flow filter membrane, clear microchannel for fluid direction and results viewing, and vertical flow porous membrane for analyte capture and detection in contact with a wick layer that conveys fluid to absorbent pads under the device backing card; and a resealable cover film. (FIG. 28C) 3D printed housing with a device that has a hinged wick for inserting into a sample reservoir such as a cup or bed pan. (FIG. 28D) Resealing of the cover film on the device after dipping where the cover film has locations to write test information (also shown in FIG. 28F) and indicators for where to place a digital reader over the read location, mocked here as a hand-written small rectangle. The bottom housing also has registration features to interface with and help position a digital reader as well as a contoured and textured tab (FIG. 28F) to facilitate handling and manipulation. FIG. 28E shows the same view as FIG. 28B, with a housing cover protecting the viewing window of the porous membrane containing the one or more capture moieties.

FIG. 30C is a table of initial LAM levels as measured by ECL and disease status of samples used in FIG. 30A and FIG. 30B. Results show the drastic impact of matrix removal on LAM detection in individual patient samples, corroborate across many different Ab pairs.

FIG. 31A shows results of standard ELISA detection of LAM before and after filtration TB− urine spiked with LAM at 5 ng/mL (5× assay LOD). In a sample with known high levels of matrix inhibition (left), head-to-head comparison of TCA-MW filtration and nylon protein binding membrane filtration (0.45 μm) demonstrates both methods were able to rescue ~1 ng/mL of LAM signal compared to the unfiltered control. At the same time, a sample with unknown levels of inhibitor was also tested (right). No matrix inhibition of the immunoassay was observed in the unfiltered sample. Importantly, these results also demonstrate that LAM is not removed by the membrane filter in the same way that the inhibitory protein is, as shown in FIG. 31B. FIG. 31B shows results of LFA dipstick LAM detection before and after membrane filtration of urine for a TB− sample spiked with 100 pg/mL of LAM (left) and remainder of a TB+ECL− sample from screening. Results demonstrate <5% reduction in LAM concentration when filtering samples with the same nylon high-protein binding membrane. Overall, results demonstrate that filtration with a protein-binding membrane provides a cost-effective and efficient method for filtering interferent from urine prior to LAM detection using a filter membrane that can be integrated into the Flow device for use at the point-of-care.

FIG. 33A shows an exemplary device comprising two sample pads stacked serially atop one another. The upstream sample pad comprises a reservoir to which the sample is added. In the figure, the reservoir is indicated by dotted lines. Dried detection reagents are housed within the upstream sample pad at a location downstream of the reservoir. The device comprises a filter system (referred to as a filter membrane in the figure) housed beneath the sample pads. The liquid flows from the sample reservoir through the sample pads, where it comes into contact with the dried detection reagents, and then passes substantially laterally through the filter membrane and onto the porous membrane containing one or more capture moieties. The device comprises a wicking component that wicks the sample from the filter system onto the porous membrane. In FIG. 33A, the flow of liquid through the wicking component is substantially lateral. As described herein, the device may comprise one or more microchannels that direct the flow of liquid onto the capture regions of the porous membrane. FIG. 33B shows an exemplary device containing an area separate from the sample pads wherein dried detection reagents are housed. In the device shown in FIG. 33B, a section of the wicking component comprises dried detection reagents. The wicking component is placed such that at least a portion of the wicking component is housed between the filter system and the porous membrane comprising one or more capture moieties. The device comprises two sample pads stacked serially atop one another, and the upstream sample pad comprises a reservoir to which the sample is added. The device comprises a filter system (referred to as a filter membrane in the figure) housed beneath the sample pads. The sample passes through the sample pads and travels substantially laterally through the filter system prior to reaching the wicking component, where it is wicked through the wicking component coming into contact with the dried detection reagents and subsequently travels to the porous membrane containing one or more capture moieties. As described herein, the device may comprise one or more microchannels that direct the flow of liquid onto the capture regions of the porous membrane. FIG. 33C shows an exemplary device described herein comprising separate sample pads and reagent pads. The device comprises two sample pads stacked serially atop one another, and the upstream sample pad comprises a reservoir to which the sample is added. The device comprises two separate reagent pads stacked serially atop one another. In some embodiments, the upstream reagent pad comprises a reservoir to which liquid detection reagents are added. In such embodiments, a liquid sample and a liquid buffer are added to their respective pads and the separate streams travel through their respective pads prior to coming into contact with the filter system. The sample then travels substantially laterally through the filter system and is wicked by the wicking component (at least a portion of which is housed between the filter system and the porous membrane) onto the porous membrane containing one or more capture moieties. In some embodiments, one or more dried detection reagents are present in one or both of the reagent pads. In such embodiments, a liquid sample is added to the sample pads and a buffer is added to the reagent pad, which travels through the reagent pad and reconstitutes the dried detection reagents. FIG. 33D shows an exemplary device described herein containing separate sample pads and a reagent pad. The reagent pad comprises dried detection reagents. The sample is added to the upstream sample pad, travels through the sample pads and comes into contact with a filter system housed beneath the sample pads. The sample then travels substantially laterally through the filter system prior to coming into contact with the reagent pad. The sample reconstitutes the dried detection reagents housed within the reagent pad, and then the sample is wicked through the wicking component onto the porous membrane containing one or more capture moieties. In the device shown in FIG. 33D, at least a portion of the wicking component is housed beneath the reagent pad, and at least a portion of the wicking component is housed between the filter system and the porous membrane containing one or more detection moieties.

FIG. 37A and FIG. 37B illustrate membrane filter protein removal and LAM loss due to membrane filtration. FIG. 37A shows two urines were syringe filtered with three different filter membranes, two high protein-binding filters (HPBF-1 and HPBF-2) and one low protein-binding filter (LPBF). Protein is quantified in both samples and calibration standards by precipitating with TCA and quantifying absorbance at 420 nm. The high-binding filters removed more protein than the low-binding filter when compared to the unfiltered control. FIG. 37B shows the high protein-binding filters were also tested for binding of LAM, with samples quantified and compared to the signal obtained from the same concentration of LAM that was not passed through a filter (i.e., the no-filter control). Results show <5% LAM loss for both, illustrating that these membranes can remove urine matrix but avoid excessive loss of LAM from the sample.

DEFINITIONS

Figure 1:
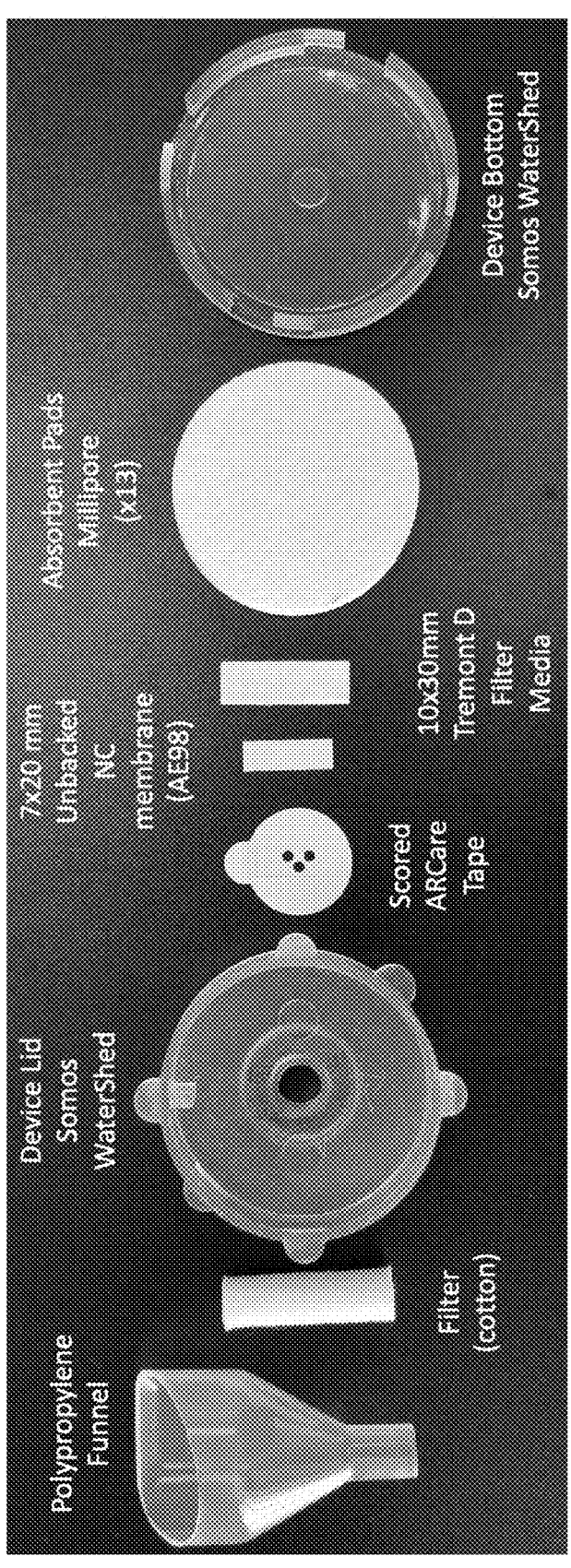
FIG. 1 shows components of an exemplary device described herein. The device comprises a lid (e.g. a top component) and a bottom (e.g. a bottom component). The device further comprises a porous membrane (e.g. nitrocellulose membrane) and absorbent pads (in this instance, 13 pads are used). The device further comprises a funnel and a filter. The filter is placed within the funnel such that the liquid sample flowing through the funnel passes through the filter prior to contacting the remaining components of the device. In this embodiment, the device is designed such that liquid flows in a gravity-assisted manner through the device. Accordingly, in this embodiment, the nitrocellulose membrane is housed above the absorbent pads. An additional filter or absorbent layer or wicking component may be placed between the nitrocellulose membrane and the absorbent pads. The liquid sample will thereby pass through the nitrocellulose membrane and is absorbed by the absorbent pads. The analyte, if present in the sample, will bind to the capture moieties held within the capture region of the nitrocellulose membrane. A patterned mask of an adhesive material (e.g. ARCare tape), or other material or treatment process (e.g., wax printing) that can limit flow through different regions of the membrane, may be used to control, direct, or limit application of antibodies (e.g. capture antibodies) to the desired locations within the nitrocellulose membrane prior to applying the sample to the device. Likewise, such tape, material, or process can be used to provide nuanced control of the flow path(s) through the membrane.

To facilitate an understanding of the present disclosure, a number of terms and phrases are defined below:

As used herein, the terms "detect", "detecting", or "detection" may describe either the general act of discovering or discerning or the specific observation of a detectably labeled composition. The term "detecting" when used in reference to an analyte refers to detecting either the presence or the absence of the analyte in the sample. In some embodiments, "detecting" an analyte in a sample refers to determining that the analyte is present in the sample. In some embodiments, "detecting" an analyte in a sample refers to determining that the analyte is not present in the sample or is not present in sufficient quantities to be detected in the sample.

As used herein, the term "liquid sample" is used in the broadest sense and includes any liquid sample type that may be obtained from a subject or from the environment. In some embodiments, the liquid sample is a "biological sample". The term "biological sample" is used in the broadest sense and is inclusive of many sample types that may be obtained from a subject. Biological samples may be obtained from animals (including humans). The biological sample may be any liquid sample, including bodily fluids such as urine, blood, blood products, sputum, saliva, etc. In some embodiments, the biological sample is a urine sample. In some embodiments, the "liquid sample" refers to a sample from a subject or from the environment that has been pre-treated (e.g., diluted, buffered, filtered, fractionated, or mixed with additives or chemical treatments) prior to use with the device.

The terms "microfluidic channel", "channel", and "microchannel" are used interchangeably herein to refer to a channel within the device through which at least a portion of the liquid sample travels. The terms are not meant to indicate that such a channel is limited to be of a certain size. The channel may be any suitable size useful within a device described herein, with the goal of transporting an appropriate amount of liquid sample to the capture region(s) and/or control region(s), if present within the porous membrane.

The term "prevent" as used herein refers to reducing the likelihood or possibility of an event occurring. For example, "preventing" a liquid sample from circumventing a filter system refers to reducing the likelihood or possibility of the liquid sample from circumventing the filter system. As another example, "preventing" passage of an undesirable moiety from a sample onto a porous membrane reduces the likelihood or possibility of the undesirable moiety to pass from the sample onto the porous membrane. "Preventing" does not necessarily indicate a complete elimination of an event. For example, "preventing" does not necessarily indicate a complete and total blockage of all undesirable moieties from passing to the sample onto the porous membrane.

The term "subject" as used herein refers to an entity from which a sample is obtained. The subject may be a mammal. In some embodiments, the subject is a human.

The terms "analyte", "target", and "target analyte" are used interchangeably herein in the broadest sense and refers to any analyte that may be detected in a sample, such as a urine sample. In some embodiments, the target is a protein (e.g. antibody), whole cell, or a nucleic acid (e.g. DNA, RNA). In some embodiments, the target is a metabolite, a carbohydrate, a glycopeptide, or a lipid.

The terms "vertical", "lateral", and variations thereof (e.g. "vertically", "laterally") when used herein in reference to a flow of liquid are provided relative to the specific component of the device that the liquid is flowing through or relative to a specific interface of two components that the liquid is flowing through. In other words, the terms "vertical" and "lateral" are given relative to a local frame of reference within the device (e.g., relative to the local tangent of the surface defined by a component surface, interface between components, or layer etc.), rather than to the entire device itself or to a more global frame of reference (e.g., relative to Earth's surface). Moreover, the terms are meant to be indicative of net movement of the liquid through the given component or interface of the device. For example, in some embodiments local flow patterns within a given component of the device may differ, in which case the net flow of the liquid through the component determines whether the flow is considered "lateral" or "vertical." For instance, various flow patterns of liquid through the porous membrane may be useful. Whether flow is "lateral" or "vertical" relative to the porous membrane is determined based upon the net movement of the liquid through the membrane.

In some embodiments, the term "lateral" and variations thereof (e.g. "laterally", "lateral flow", "substantially lateral flow" etc.) are given relative to a specific component of the device (e.g. a material) and indicate that the net flow of liquid through the material is substantially in the plane of the material. The plane of the material does not necessarily need to be flat. For example, for a curved material, the curved surface can be considered an approximation to a plane and traveling substantially in the approximation of the plane is still considered "lateral" flow. In some embodiments, the term "lateral" is given relative to an interface of two different components of the device and indicates that the net flow of liquid through the interface is generally in the plane of two components making up the interface. In contrast, in some embodiments the term "vertical" and variations thereof (e.g. "substantially vertically", "vertical flow", or "substantially vertical flow") is used relative to a specific component of the device (e.g. material) and indicates that the net flow of the liquid through the material is substantially perpendicular to the plane of the material. As described above, the plane of the material may not necessarily be flat. For example, a surface, layer, or interface may be curved and the plane that is locally tangent to the curved surface, layer, or interface can be used to determine if net flow is substantially vertical. Flow of the liquid generally perpendicular to the locally tangent plane is still considered to be "vertical" or "substantially vertical" flow. In some embodiments, the term "vertical" is given relative to an interface of two different components of the device and indicates that the net flow of liquid through the interface is generally approximately perpendicular to the surface defined by that interface.

Typically, the term "vertical" means that the flow of liquid is in an up/down direction assuming the component(s) or interface(s) are laying flat on a horizontal surface). However, the term is not meant to exclude the possibility of lateral (e.g. side to side) flow from occurring in some areas of the device. For instance, various flow patterns of liquid through the porous membrane may be useful; so long as the liquid has a net transverse movement through the porous membrane (i.e., <90° from the normal to the plane of the membrane), the flow may be referred to as "vertical" whether or not the membrane is oriented horizontally or not.

It is expressly contemplated herein that the devices described herein provide for substantially vertical flow through one component or interface of the device and substantially lateral flow through another component or interface of the device. The terms "hybrid", "hybrid flow", "hybrid device", "hybrid methodology" and the like are used to refer to the use of substantially vertical flow through some components and substantially lateral flow through other components of the device, providing novel functionalities. For instance, vertical flow through a filter membrane enables integration of large area filter membranes that cannot be achieved with lateral flow without clogging in the same device footprint, thereby enabling processing of larger volumes while enabling use of lateral flow to transport fluid, introduce reagents, and direct fluid to small detection regions within a compact device architecture that can be manufactured using extremely cost-efficient roll-based manufacturing.

DETAILED DESCRIPTION

In some aspects, provided herein are devices and methods of use thereof for detecting one or more analytes in a sample. In some embodiments, the sample is a liquid sample. In some embodiments, the sample is a biological sample. In some embodiments, the sample is a urine sample.

In a general sense, provided herein are various types of devices. In some embodiments, provided herein are devices that rely on the flow of liquid through one or more components of the device in a substantially vertical fashion, potentially assisted or impeded by the force of gravity. Devices in which the liquid flows in the same direction as the gravitational force through one or more components of the device are referred to herein as "gravity-assisted" devices. The term "gravity-assisted" is not intended to indicate that gravity is the only or substantially the only force pulling the liquid through the device. For example, gravity-assisted devices may additionally comprise wicking materials and/or absorbent layers that pull the liquid through one or more components of the device. For example, the gravity-assisted device may additionally comprise wicking material that assists in transferring liquid through one or more components of the device via capillary action. In some embodiments, the liquid may be pulled through the one or more components of the device in an acceleration-assisted manner, such as using a centrifuge. Accordingly, a gravity-assisted device may be used in conjunction with acceleration to facilitate movement of the liquid through the device. Such movement may be referred to herein as "acceleration-assisted." In other embodiments, provided herein are devices that rely on the flow of liquid through one or more components of the device in a substantially vertical fashion, against the force of gravity. Such devices are referred to herein as "wicking devices". For example, wicking devices may comprise a wicking component that pulls liquid up into one or more components of the device via forces such as capillary action. Whether a liquid is described as flowing substantially in the same direction as the gravitational force (e.g. in a gravity-assisted manner) or substantially against the force of gravity can be dependent on the orientation of the device relative to the gravitational force, or the orientation of a specific component containing liquid at a given time relative to the gravitational force. The devices described herein can be manipulated (e.g. turned, flipped, etc.) during use, and as such the description of a liquid flowing with or against gravity is meant to be understood relative to the given orientation of the device or a component therein at a given time.

In some aspects, provided herein is a device wherein flow of a liquid sample through at least one component of the device is substantially lateral, and flow of the liquid sample through at one other component of the device is substantially vertical. For example, in some embodiments provided herein is a device comprising a plurality of porous materials, wherein the device is configured such that a liquid sample flows substantially vertically through at least one of the plurality of porous materials and substantially laterally through at least one of the plurality of porous materials. Such a device is also referred to herein as a "hybrid" device. The flow of the liquid sample in a hybrid device may be acceleration-assisted, gravity-assisted, and/or driven at least in part by wicking. The term "device" is inclusive of all types of devices described herein, including gravity-assisted devices, acceleration-assisted devices, hybrid devices, and wicking devices or devices representing combinations of those methodologies (e.g., acceleration-assisted and wicking methodologies). The term "device" does not necessarily indicate that all of the components are contained together within a discrete unit. Rather, a "device" may comprise multiple, discrete units. For example, in some embodiments a "device" comprises a filter system and a housing body containing a porous membrane. The filter system may exist separately from the porous membrane (e.g. may not be contained within the housing body of the device), but the filter system is still considered part of the "device" as described herein.

In some embodiments, provided herein is a device for detecting one or more analytes in a liquid sample. In some embodiments, the device comprises a housing body. In some embodiments, the housing body comprises an opening to permit entry of the liquid sample into the housing body. In some embodiments, the housing body comprises a first component and a second component that removably connect to each other to form a watertight seal. In some embodiments, these components are referred to herein as a "top component" and a "bottom component". The terms "top" and "bottom" are used to indicate the position of the first component and the second component relative to each other at a given point in time. In some embodiments, the terms "top" and "bottom" are used to indicate the position of first component and the second component relative to each other at the point in time in which the liquid sample is added to the device. For example, in some embodiments the "top component" is oriented above the "bottom component" at the time the liquid sample is added to the device. It is understood, however, that in some embodiments the methods described herein involve flipping the device to permit passage of the liquid sample in the desired fashion through one or more components of the device. In such embodiments, the "top component" when the liquid sample was added to the device may be inverted, such that the top component is actually oriented below the component that was previously considered to be the "bottom component" at the time the liquid sample was added to the device.

In some embodiments, the first component is referred to herein as a "lid" or a "cap". In some embodiments, the second component is referred to herein as a "cup" or a "sample collection cup". In a general sense, the housing body serves to hold all the components in place, apply sufficient pressure to the components housed within, receive fluid, hold fluid, store dry or wet reagents, align reader instrumentation, and/or potentially seal away possibly biohazardous material (e.g. urine). In some embodiments, the device body is composed of a material that does not bind the target analyte, but is rigid enough to provide structural support and apply pressure to the components within. For example, the device body may comprise a plastic material or biodegradable material.

In some embodiments, such as shown in FIG. 28, the first component is a resealable film. The resealable film can be peeled back to expose the contents of the device contained within the second component (e.g. the bottom component of the housing body). In some embodiments, the bottom component is a tray, which keeps the working surface clean and provides a surface to connect to the resealable film. In some embodiments, the resealable film can be peeled back to expose the wicking component. In some embodiments, the resealable film is attached to the bottom component of the housing body such that after peeling back a sufficient amount, the force required to continue pulling the film away increases dramatically, thereby preventing a user from accidentally removing the entire film from the bottom component of the housing body. In some embodiments, the resealable film can be peeled back to expose a wicking component that is flexible in orientation, thereby allowing the flexible wicking component to be brought into contact with a liquid sample. For example, as shown in FIG. 28C, the resealable film can be pulled back to expose the flexible wicking component, and the flexible wicking component can be dipped into a liquid sample. Following wicking of a sufficient amount of sample onto the wicking component, the device can be laid flat and the film is resealed. The liquid sample can then flow through the various components of the device (e.g. flow through the wicking component, flow through the filter system, enter a microchannel if present in the device) and come into contact with the porous membrane containing the one or more capture moieties. In some embodiments, resealing the film after addition of sample prevents leaking of sample during handling. Moreover, the resealable film (or other exemplary components of the housing body) provide an area for patient information, written instructions, or other desirable information to be written. The resealable film (or other exemplary components of the housing body) can also provide guide marks for placing a reader, if necessary for interpretation of assay results. In some embodiments, the resealable film and/or tray comprise biodegradable materials. In some embodiments, the tray comprises features that facilitate location/registration of a reader device for assessing results.

In the accompanying figures, the housing body is shown as cylindrical in shape. However, it is understood that other suitable shapes may be employed, including squares, rectangles, etc. The shape of the housing body is dependent on the shape of the first component and the second component, and how they attach together. Accordingly, a sample collection cup that is cylindrical in shape and a lid that is cylindrical in shape will attach together to form a housing body that is also cylindrical in shape. In such embodiments, the shapes of some components may be designed to fit snugly within the housing body. In some embodiments, the filter system may comprise multiple filter components. In some embodiments, the filter system comprises multiple filter layers, each of which is circular, such that each filter layer stacks on top of one another and fits snugly within the housing body. However, not all components of the device need to be the same shape. For example, even in a cylindrical device, the porous membrane may be square or rectangular in shape. This is shown, for example, in FIG. 1. Overall, the size, shape, and thickness of materials should be selected to achieve adequate pressure within the system to facilitate transfer of fluid between the layers, without building up too much pressure to cause structural failure or impede flow.

The housing body may comprise one or more features to help apply pressure to the components within (e.g. the wicking component, absorbent pad(s), porous material, etc.). For example, a series of latches, locks, or size constraints can be applied to the device body in order to help apply pressure to the components within to facilitate flow through the multiple layers. In some embodiments, the first component and/or the second component may comprise one or more indented areas (e.g. bumps) that apply pressure to the materials immediately proximal to the bumps. In some embodiments, the housing body is slightly flexible in order to accommodate the expansion that the absorbent material undergoes while the vertical flow assay is taking place. However, expansion should be balanced with the need to maintain sufficient pressure to allow the fluid to continue to be absorbed. In some embodiments, the housing body can be sealed (e.g. a lid, bag, or some other method) prior to disposal to ensure any residual sample liquid is contained.

In some embodiments, the housing body comprises one or more features to facilitate imaging of the membrane following the assay. For example, the device may comprise locating features to assist in identification of the capture and control regions on the porous membrane held within the housing body. In addition, features that make it easier for the user to manipulate the components are also advantageous (e.g., features to facilitate gripping, turning, sliding, flipping, latching/unlatching, proper/consistent orientation, etc.).

Figure 32:
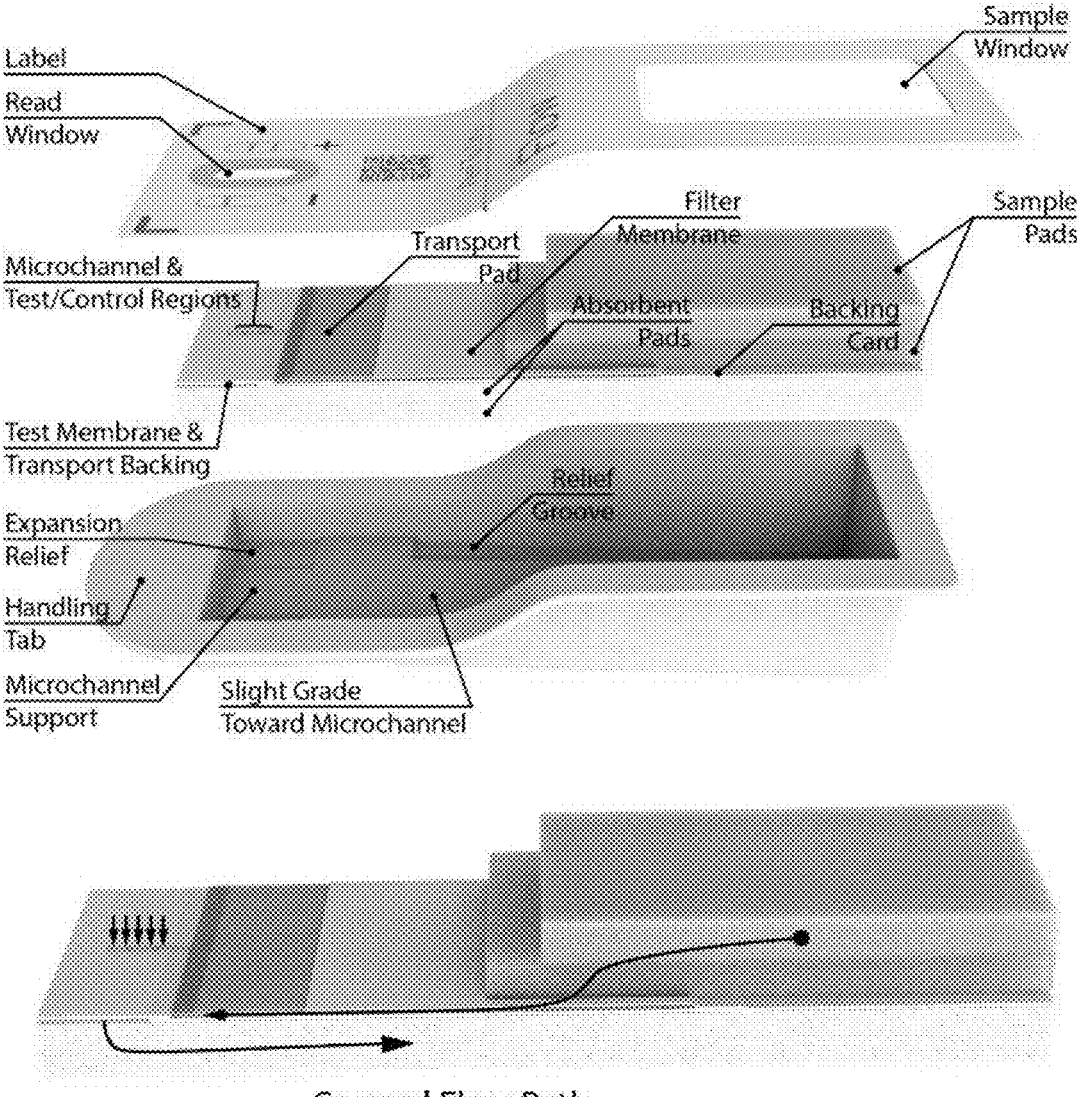
FIG. 32 is a schematic showing an exemplary device provided herein. The device is manufactured at least in part by roll manufacturing. The roll-manufactured portion of the device comprises the backing card, wicking layer (referred to in the figure as the transport membrane), wicking layer (referred to in the figure as the transport pad), microchannel (comprising adhesive tape layer and transparent film adhered on top of the porous test membrane), porous membrane containing capture moieties (referred to as the test membrane) and transport backing (to facilitate contact between the test membrane and absorbent pads). The device comprises a housing body that holds the internal components within the device. The housing body can additionally provide information to the user (e.g., how to interpret results, identification codes such as 2D barcodes, user steps, etc.), which can be printed on the housing body. To assemble the device, the absorbent pads are placed in the device body, the roll-manufactured components are placed on top of absorbent pads, the sample pads are placed on top of the roll-manufactured component, and finally the label. Not shown is a sticker (e.g., a biohazard sticker) that could be placed over the sample window to contain fluids within the device and mark for safe handling/disposal. Additional features include: a window in the label for reading the test/control regions of the test membrane, a handling tab on the device body to make it easier for the user to manipulate the device without touching the microchannel, support within the device body to maintain a slight grade of the roll-manufactured component toward the microchannel to gently encourage fluid from the sample pad toward the microchannel, support underneath the microchannel bordered by expansion reliefs on either side to prevent delamination of the label due to expansion of the absorbent pads as they wet while maintaining pressure under the microchannel, and relief grooves under the absorbent pads to avoid internal radii needed for device manufacturing from binding/lifting the pads unnecessarily. An additional feature of the device not shown/labeled are dried spots of dye in the absorbent pads that spread when wet to indicate flow in the device and estimate the volume of fluid that has been absorbed. The flow path indicates the general path of fluid from the sample pad, through the filter membrane, into the transport pad, into the microchannel, down through test membrane, into the transport backing, and into the absorbent pads.

In some embodiments, the housing body comprises one or more features to facilitate the desired flow of fluid sample through/within various components of the device. For example, in some embodiments the bottom component of the housing body is slightly graded towards the microchannel of the device to facilitate flow of liquid sample towards the microchannel (which directs flow of liquid to the capture and/or control regions of the porous membrane). In some embodiments, the bottom component of the housing body comprises one or more relief grooves/areas to accommodate expansion of the interior components of the device (e.g. absorbent pads, sample pads, etc.) upon addition of liquid sample to the device. An exemplary bottom component of a housing body is shown in FIG. 32.

In some embodiments, provided herein is a device for detecting one or more analytes in a liquid sample. In some embodiments, the device comprises a plurality of porous materials, wherein the device is configured such that a liquid sample flows substantially vertically through at least one of the plurality of porous materials and substantially laterally through at least one of the plurality of porous materials. Accordingly, the device is considered a "hybrid device". In some embodiments, one of the plurality of porous materials comprises a porous membrane containing one or more capture moieties held within a defined capture region of the porous membrane. In some embodiments, the porous membrane further contains one or more detection moieties. In some embodiments, the plurality of porous materials comprise the porous membrane containing one or more capture moieties held within a defined capture region of the porous membrane; and at least one wicking component. In some embodiments, the plurality of porous materials comprise the porous membrane containing one or more capture moieties held within a defined capture region of the porous membrane, at least one wicking component, and at least one absorbent pad. In some embodiments, the device is configured such that the liquid sample is wicked through the wicking component substantially vertically or substantially laterally prior to contacting the porous membrane containing one or more capture moieties. In some embodiments, the liquid sample subsequently flows through the porous membrane containing one or more capture moieties and into the at least one absorbent pad. In some embodiments, the hybrid device does not comprise a filter system. For example, for processing of certain liquid sample types a filter system may not be necessary. For example, for detection of pathogens in a water sample, a filter system may not be necessary. In some embodiments, the device further comprises a filter system. In some embodiments, the plurality of porous materials comprises the porous membrane containing one or more capture moieties held within a defined capture region of the porous membrane, at least one wicking component, at least one absorbent pad, and a filter system comprising one or more filter components. In some embodiments, the device is configured such that the liquid sample flows through the filter system prior to contacting the porous membrane containing one or more capture moieties, and subsequently flows through the porous membrane containing one or more capture moieties and into the at least one absorbent pad.

In some embodiments, provided herein is a device for detecting one or more analytes in a liquid sample. The device comprises a filter system comprising one or more filter components (e.g. filter layers), a porous membrane, and at least one absorbent pad. In some embodiments, the porous membrane contains one or more capture moieties held within a defined capture region of the porous membrane. In some embodiments, the porous membrane further contains one or more detection moieties. In some embodiments, the device is configured such that a liquid sample flows through the filter system prior to contacting the porous membrane, and subsequently flows through the porous membrane and into the at least one absorbent pad. In some embodiments, the device is configured such that the liquid sample flows substantially vertically through the filter system prior to contacting the porous membrane, and subsequently flows through the porous membrane and into the at least one absorbent pad. In some embodiments, the porous membrane and the at least one absorbent pad are contained within the housing body. In some embodiments, at least a portion of the filter system is also contained within the housing body. In some embodiments, the housing body comprises an opening to permit entry of the liquid sample into the housing body.

In some embodiments, provided herein is a gravity-assisted device for detecting one or more analytes in a liquid sample. In some embodiments, the device comprises a housing body. The housing body comprises an opening to permit entry of the liquid sample into the housing body. In some embodiments, the housing body comprises a first component and a second component. In some embodiments, the first component comprises an opening to permit entry of the liquid sample into the housing body. For example, the first component may comprise an opening that may be aligned with a suitable component (e.g. a funnel) to direct flow of the liquid sample into the opening.

In some embodiments, the device (e.g. a gravity-assisted device) further comprises a component to direct flow of the liquid sample into the opening. In some embodiments, the component to direct flow of the liquid sample into the opening is a funnel. For example, the first component may comprise an opening that may be aligned with a funnel. The liquid sample (e.g. urine) may be applied to the funnel, and pass through the funnel into the opening, thereby entering the housing body of the device. The funnel is designed to hold a set volume of liquid and supply a consistent supply source liquid to flow through. For example, the funnel may be capable of holding at least 5 mL of liquid. For example, the funnel may hold at least 5 mL, at least 10 mL, at least 15 mL, at least 20 mL, at least 30 mL, at least 40 mL, at least 50 mL, at least 60 mL, at least 70 mL, at least 80 mL, at least 90 mL, or at least 100 mL of liquid. The funnel may comprise any suitable material. The funnel should comprise a material that does not significantly bind to the analyte of interest. In some embodiments, the funnel may comprise plastic, such as a polypropylene plastic.

In some embodiments, the funnel comprises one or more additional components to prevent spillage of the liquid sample (e.g. urine) from the funnel before, during, and/or after use. For example, the funnel may comprise an excess reservoir to notify the user of overfill and prevent excess urine from running through the assay or subsequently being spilled during handling. As another example, the funnel may comprise a check valve mechanism to prevent spillage of excess urine from the funnel during removal from the device. The funnel may also comprise a cap, which may be placed upon the funnel after removal from the device to prevent loss of leftover urine. A funnel cap may also have absorbent material that absorbs fluid remaining within the funnel when applied to the funnel.

In some embodiments provided herein is a wicking device for detecting one or more analytes in a liquid sample. In some embodiments, the device comprises a housing body comprising an opening to permit entry of the liquid sample into the housing body. In some embodiments, the housing body comprises a first component and a second component. Various additional components may be housed in the first component (e.g. the cap), the second component, and/or within the housing body). In some embodiments, the wicking device is designed such that the device is brought into contact with the liquid sample, and the liquid sample is pulled through at least one component of the device substantially against the force of gravity. In some embodiments, the liquid sample is pulled through at least one component of the device substantially vertically, against the force of gravity. In some embodiments, the wicking device comprises a wicking component to pull the liquid sample through at least one component of the device substantially against the force of gravity. In some embodiments, the wicking component is the filter system. For example, the filter components (e.g. filter layers) may also have wicking abilities, such that the filter itself serves to pull the liquid into the device. In other embodiments, the wicking component and the filter system are separate entities.

In some embodiments, provided herein is a device wherein flow of a liquid sample through at least a portion of the device is substantially lateral, and flow of the liquid sample through at least a portion of the device is substantially vertical. Such a device is also referred to herein as a "hybrid" device. The flow of the liquid sample in a hybrid device may be acceleration-assisted, gravity-assisted, and/or driven at least in part by wicking.

Figures 33A, 33B, 33C, 33D:
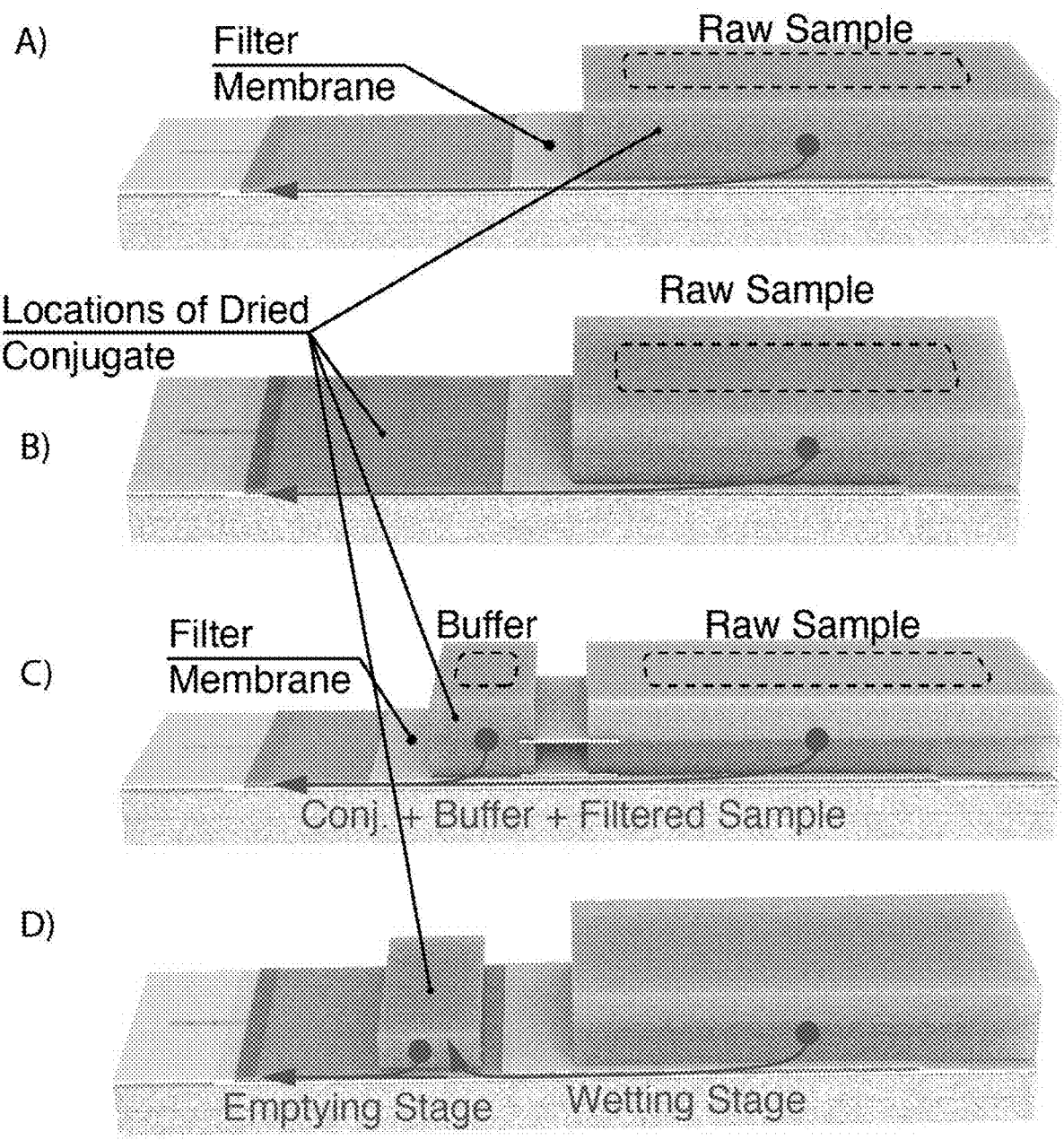
FIGS. 33A-33D show exemplary embodiments of a device provided herein.
Figures 34A, 34B:
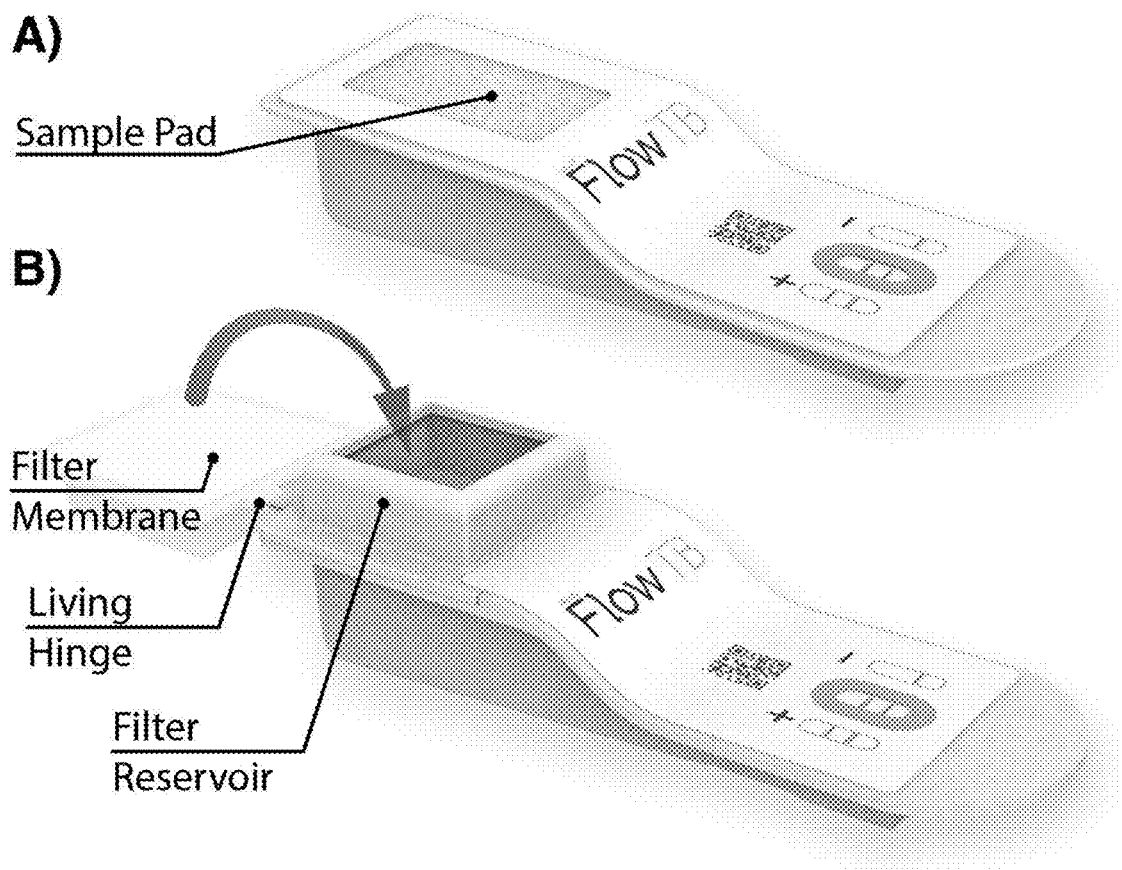
FIG. 34A shows an assembled device with internal design similar to that described and shown in FIG. 33A. In this design, conjugate(s) (i.e., detection reagents) that are dried into the sample pad are allowed to mix with unfiltered urine, thereby allowing potential inhibition of analyte detection by components in the urine.
FIG. 34B shows a device design that pre-filters the sample on-device prior to mixing with conjugate(s) (i.e., detection reagents) to avoid inhibition. The device shown in FIG. 34B comprises a living hinge (e.g. a thinned section of material that joins two portions of the body and can flex without breaking, creating a hinge without any additional pieces or assembly). The living hinge attaches a portion of the device comprising a filter system (e.g. a filter membrane) to the remaining components of the device, which may include components similar to those shown in FIG. 32 or FIG. 33. The portion of the device comprising the filter system can be considered a "lid". In some embodiments, the lid comprises a sample pad and the filter system. In some embodiments, the lid comprises a reservoir (e.g. an opening to which sample is added) and a filter system, and does not contain a sample pad. In some embodiments, the remaining components of the device comprise one or more sample pads, one or more reagent pads, one or more wicking components, the porous membrane containing one or more capture moieties, and/or one or more microchannels. The device is manufactured in the "open" position, where the lid is open and the filter membrane is exposed, as shown in FIG. 34B. The "open" position exposes a reservoir (referred to in the figure as a "filter reservoir"). During assembly and/or use of the device, the lid is closed (as shown by the gray arrow) to place the filter system over the reservoir. In some embodiments, the reservoir houses one or more sample pads. The device may be held in the "closed" position by the device label, maintaining contact between the filter system and the soft, compressible sample pads underneath. The sample is added to the opening of the lid, soaking the sample pad of the lid if present, and passes through the sample pad and onto the filter system of the lid. The sample then passes through the filter system and into the sample reservoir, where capillary action draws fluid from the reservoir substantially wetting the sample pads (e.g. the sample pads in the main body of the device, not the sample pad on the lid to which the sample was added) and starting flow through the components of the device to the microchannel and test-regions in 1-2 mins. Upon wetting of the sample pad, the assay proceeds the same way as the design shown in FIG. 34A except that the urine has been filtered before reconstituting the dried Ab conjugate.

For any of the embodiments described herein, the device may comprise one or more sample pads. A "sample pad" refers to a component of the device which absorbs the sample and directs flow of the sample to the desired components within the device. In some embodiments, the sample pad is the component of the device which first comes into contact with the sample. For example, in some embodiments the sample pad is an exposed area of the device, or an area of the device that can be exposed (e.g. by removal of a cover, removal of a lid, closure of a lid, removal of an adhesive strip, removal of a seal, etc.), to which the sample is added. An exemplary embodiment is shown in FIG. 32, wherein the sample pad is placed upstream of other porous materials such that the sample is added to the sample pad (e.g. through a sample window) and travels through the sample pad to other components of the device. In some embodiments, the device comprises more than one sample pad. For example, in some embodiments the device comprises two sample pads. In some embodiments, the device comprises three sample pads. In some embodiments, the device comprises at least two sample pads stacked such that at least a portion of a first sample pad overlaps with at least a portion of a second sample pad. In some embodiments, the sample pads are stacked in a stepwise manner, as shown in FIG. 32. In some embodiments, the sample pads are stacked serially, as shown in FIG. 33A-33D. In some embodiments, the device comprises one or more sample pads upstream of the filter system. In some embodiments, as shown in FIG. 34B, the device comprises a lid containing a filter system. The lid can contain a sample pad on top of the filter system such that, when the lid is closed, the sample pad is upstream of the filter system, and the filter system rests atop or fits within a corresponding reservoir on the body of the device. The sample is added to the lid, and passes through a sample pad (if present), then passes through the filter system of the lid prior to coming into contact with the other components of the device. The reservoir temporarily holds a volume of sample that has been added to the lid (e.g. in some embodiments added to the sample pad or simply on top of the filter system, and then passed through the filter system), as the sample wets and is absorbed into the sample pad(s) present within the body of the device. The sample pad(s) may be any suitable size, shape, or dimensions to facilitate proper fit within a housing body. Generally, the thickness of the sample pad facilitates absorption of the sample to prevent the sample from overflowing from the device, while enabling flow of the sample to other components of the device such as for downstream filtration and/or detection of the target analyte.

In some embodiments, the device comprises a reservoir which temporarily holds a volume of fluid (e.g. sample, buffer) prior to the fluid traveling through the reservoir to the other components of the device. In some embodiments, the device comprises a sample reservoir which temporarily holds a volume of the liquid sample as the sample travels to the other components of the device. In some embodiments, the device comprises a reservoir which temporarily holds a volume of sample while the sample is absorbed into and passes through one or more sample pads. For example, in some embodiments the sample pads within the device body act as a temporary reservoir which holds a volume of sample while the sample passes through the sample pads into the other components of the device. In some embodiments, the device comprises a buffer reservoir which temporarily holds a volume of buffer as the buffer passes to the other components of the device. In some embodiments, the liquid is directly added to the reservoir. For example, as shown in FIG. 33A, FIG. 33B, and FIG. 33C, the sample may be added directly to the sample reservoir on the upstream surface of the sample pad. As another example, as shown in FIG. 33C, in some embodiments, the device comprises a reservoir which temporarily holds a volume of buffer added to the device (e.g. to reconstitute dried reagents) while the buffer is absorbed into and passes through one or more reagent pads. In some embodiments the buffer is added directly to the buffer reservoir. In other embodiments, the fluid (e.g. the sample, the buffer) is added to a component of the device other than the reservoir. For example, as shown in FIG. 34B, in some embodiments the sample is added to the lid of the device and passes through the filter system of the lid prior to entering the reservoir. The sample is then held within the reservoir as the sample wets and is absorbed into/passes through the sample pads within the main body of the device (e.g. not within the lid).

In some embodiments, a sample pad comprises a reservoir positioned on its top surface (i.e., upstream). For example, in some embodiments a portion of the sample pad acts as a reservoir which temporarily holds a volume of fluid while the fluid absorbs into and passes through the sample pad and into the other components of the device. In some embodiments, the reservoir comprises a sufficiently low fluid resistance to deliver fluid appropriately to other components of the device while preventing overflow/flooding of the device. In some embodiments, the bottom of the reservoir comprises a filter membrane. Accordingly, when fluid is added to the reservoir, it passes through the filter membrane and contaminants are removed prior to the sample flowing through other components of the device. In some embodiments, the device performs primary and secondary filtration. In some embodiments, primary filtration is performed by the filter membrane beneath the reservoir, and secondary filtration is performed by the filter system positioned underneath the sample pad. In this configuration, the filter system beneath (e.g. downstream of) the sample pad can be left in place or removed depending on whether the secondary filtering is necessary. The reservoir may be an origami reservoir constructed of foldable material and in some embodiments the origami reservoir is adhered to or integrated with the device label. In some embodiments, as shown in FIG. 34B, the reservoir is designed In some embodiments, the device is configured such that a sample is added to a sample pad, and the sample flows through the sample pad into the filter system. In some embodiments, the flow of the sample through the sample pad is substantially vertical. In some embodiments, the flow of the sample through the sample pad is substantially lateral. In some embodiments, the sample flows through the sample pad in both vertical and lateral flow paths.

In some embodiments, the device is configured such that a sample is added to a first sample pad, and the sample flows from the first sample pad into a second sample pad. In some embodiments, the flow of the sample through the first sample pad is substantially vertical, and the flow of the sample through the second sample pad is substantially lateral. In some embodiments, the sample flows from the second sample pad onto the filter system. In some embodiments, the device is configured such that a wicking layer (also referred to as a "transport pad") contacts the filter system. In some embodiments, the device is configured such that a wicking layer contacts the filter system and the porous membrane containing one or more capture moieties. In some embodiments, at least a portion of the wicking layer is positioned between the filter system. In some embodiments, the wicking layer is positioned such that the wicking layer wicks the sample from the filter system to the porous membrane containing moieties for capture of a target analyte in the sample (e.g. within a capture region of the porous membrane). In some embodiments, the sample flows through the filter system and through the wicking layer in a substantially lateral flow path. In some embodiments, the device comprises a microchannel that directs flow of the liquid from the wicking layer to the capture region and/or control region of the porous membrane. In some embodiments, the device comprises a viewing window that permits viewing of signals from the capture and/or control region of the porous membrane.

Figures 35A, 35B, 35C, 35D, 35E:
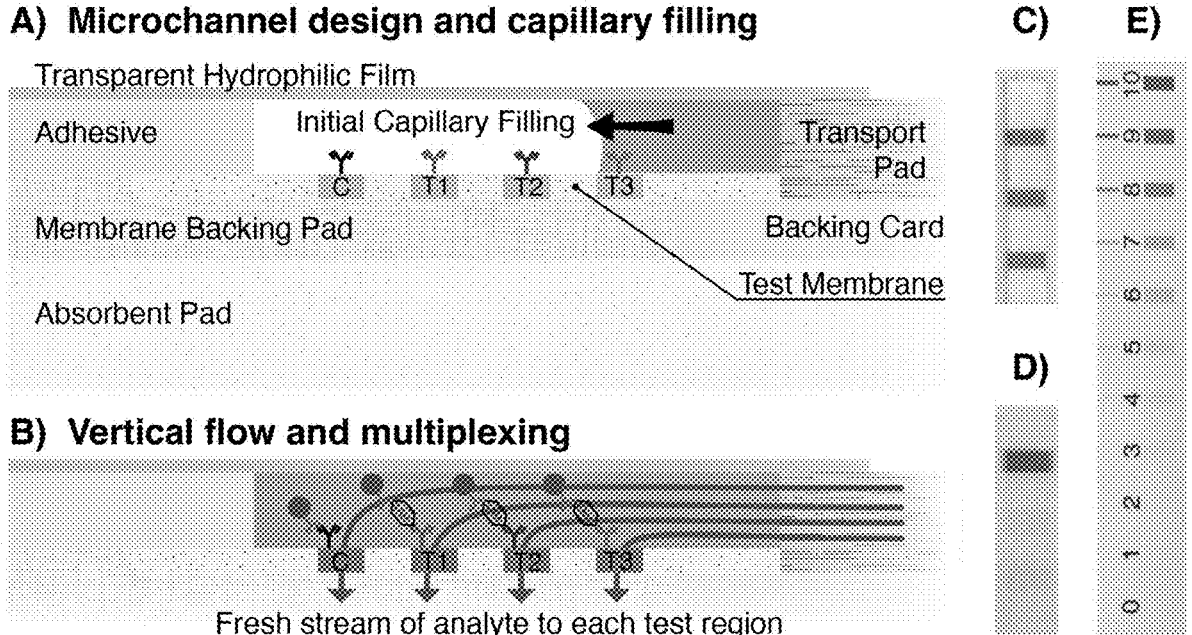
FIG. 35A shows a cross-section schematic drawing of the microchannel and test region shows how the microchannel is constructed and how initial wetting of the transport layer causes capillary filling of the microchannel. The microchannel "ceiling" is made of hydrophilic transparent polyester to ensure proper filling of the channel and enable real-time visualization of results.
FIG. 35B illustrates how, after initial capillary filling, absorbent pads below "pull" fluid through the microchannel and test regions. Laminar flow in the microchannel brings fresh streamlines of sample, with LAM and Ab-labeled gold conjugate, to each Ab-labeled test region. Thus, test-line position does not influence results (contrasting with standard lateral flow). Furthermore, when a single Ab conjugate is used, there is no opportunity for Ab cross-reactivity and test-lines can be added or removed from the device without any impact on the results of other test lines. In some embodiments, the microchannel enables striping of up to 3 test-lines (T1-T3) and a control line (C).
FIG. 35C shows an example image of three control line antibodies striped on the test membrane and run with a single antibody-labeled conjugate to quantify the unbiased distribution of sample across the test membrane. Results across replicates had <5% variation between lines.
FIG. 35D shows an example image of multiplexed LAM detection (2 test-lines+control) with typical test-line intensities near LOD (~3-4 on visual grading scale.
FIG. 35E shows an image of a reference card for visual grading results without a reader.
Figure 36:
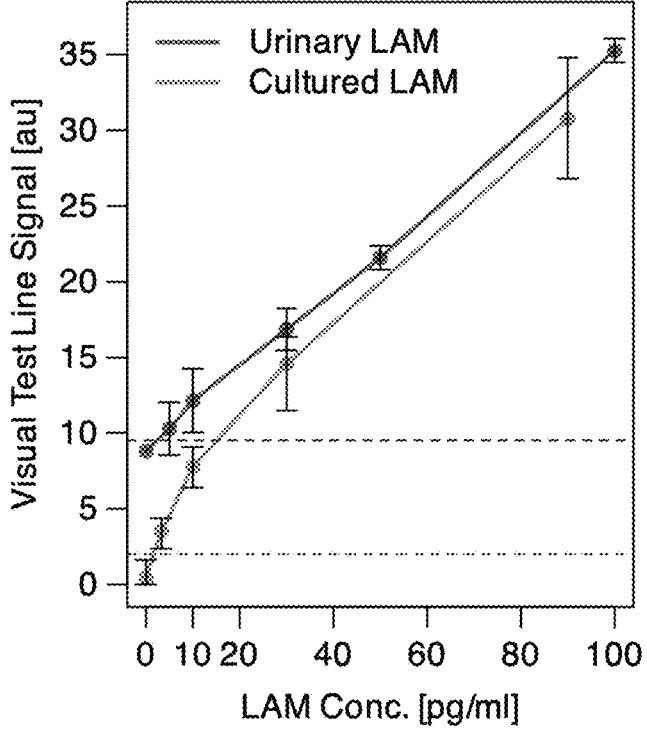
FIG. 36 shows the results of limit of detection experiments performed using an exemplary device provided herein manufactured by roll-based assembly with two different Ab-pairs. One Ab pair was tested on cultured LAM and one tested on LAM isolated from a patient. Results demonstrate a limit of detection of <10 pg/mL for both pairs compared to the only approved traditional LAM urine lateral flow assay (Determine TB LAM) that has a limit of detection of the 500 pg/mL LAM.

In some embodiments, the device comprises a backing card. In some embodiments, the backing card is positioned to prevent flow of the sample directly through the sample pads and into the absorbent pad. In other words, the backing card prevents/impedes the sample from bypassing the filter system and porous membrane containing the one or more capture moieties. In some embodiments, the backing cad is positioned beneath the sample pads, filter system, and wicking layer, but above the absorbent pads. The backing card should not prevent flow of liquid from the porous membrane containing the one or more capture moieties into the absorbent pad. For example, as shown in FIG. 32 and FIG. 35A-35B, an exemplary flow path of a liquid sample added to such a device is to travel through the sample pads, through the filter system, through the wicking layer, onto the porous membrane containing one or more capture moieties, and subsequently flow through to the absorbent pads and away from the porous membrane containing one or more capture moieties.

In some embodiments, the device comprises a transport backing. In some embodiments, the transport backing (referred to in FIG. 35 as a membrane backing pad) facilitates contact between the porous membrane comprising one or more capture moieties and the absorbent pads, and thus facilitates flow of liquid from the porous membrane into the absorbent pads. In some embodiments, the transport backing comprises cellulose, cotton or other natural fiber, glass, polyester, polypropylene, nylon, or a similar material.

Figure 2:
FIG. 2 shows an image of an exemplary funnel containing a filter system as described herein.

For any of the embodiments described herein, the device may comprise a filter system. In some embodiments, the filter system is housed within the funnel. Such embodiments may be particularly useful for a gravity-assisted device wherein a funnel is used as the component to direct the flow of liquid into the device. For example, the filter system may be housed within the "bottleneck" of the funnel, as shown in FIG. 2. In some embodiments, at least a portion of the filter system is external to the house body comprising the porous membrane. In some embodiments, the filter system is proximal to the top component (e.g., the lid) of the housing body, such that the sample passes through the filter system, into the housing body, optionally into further layers of the filter system present within the housing body, and into contact with the porous membrane. In some embodiments, the filter system is housed within the housing body of the device. For example, in some embodiments the filter system is housed within the housing body of the device, such that the filter system is directly proximal to the top component (e.g. the lid) of the housing body. In some embodiments, the topmost filter component may be in contact with the top component of the housing body. In some embodiments, the topmost filter component is in contact with the inner surface of the top component of the housing body.

The filter system may also be referred to herein as a "filter" or a "filter cartridge". The filter system comprises one or more filter components. In some embodiments, the filter system comprises one or more filter layers. The components may be stacked together in a serial fashion. In some embodiments, the filter system comprises at least two filter components. The filter system can perform any type of filtration, including but not limited to size-based filtration, capture/affinity-based filtration, or both. In some embodiments, the filter system performs size-based filtration. In some embodiments, each filter component comprises pores for removal of potential contaminants (e.g. matrix) from the sample. For example, each component may comprise pores of a suitable size to remove potential contaminants that are typically found in urine. However, the filter system should not significantly deplete the analyte of interest. Moreover, the filter system should not bind to or substantially inhibit a detection moiety from reaching the porous membrane such that functionality of the device is lost. For example, the filter system should not bind to or inhibit a substantial fraction of the detection antibody or labeled particle from reaching the capture region of the porous membrane, such as a capture antibody or labeled conjugate particle that is added to the sample prior to passing the sample through the device.

In some embodiments, the filter system comprises at least one filter component comprising pores. In some embodiments a detection particle is added directly to the sample, requiring the filter to have pore sizes larger than the detection particle (e.g., a diameter of 0.2 μm-0.5 mm to permit common particles used in traditional lateral flow assays). In some embodiments, the filter system comprises multiple filter components, wherein each component comprises pores of about 0.2 μm-0.5 mm in diameter. In some embodiments, the filter system comprises multiple filter layers comprising pores of about 0.2 μm-0.5 mm in diameter. In some embodiments, the filter components (e.g. filter layers) are arranged such that the first component to contact the sample has the largest diameter pores. The components may be arranged such that the size of the pores decreases sequentially from the first component (e.g. the first layer) to contact the sample to the last. In doing so, the filter system will filter out a gradient of particle sizes to prevent blocking of flow through the system. For example, the first filter component will filter out the largest particles, the second filter component will filter our medium-sized particles, the third filter component will filter our smaller particles, etc. In other embodiments, the pore size may not diminish in a sequential fashion from one component to the next. For example, some materials are more structurally rigid or resilient than others; therefore, it may be advantageous to situate a less resilient layer between more resilient layers even if the monotonicity of the pore size gradient is interrupted (e.g. pore size may go from large, to med-large, to med, to small, to med-small instead of large, to med-large, to med, to med-small, to small). Likewise, one or more wicking components with relatively large pore size could be situated between the porous detection membrane and the small pore size filter elements to help mediate even transfer of fluid.

In some embodiments, a small pore size filter is situated between two larger pore-size filters or wicking components. Such a configuration creates a more uniform flow rate across the surface of the small pore-size material. This is because the large pore-size material provides little resistance to flow compared to the small pore-size material. Thus, flow streamlines with longer or shorter path lengths through the filter have less relative difference in total fluidic resistance. Such a configuration helps to maximize use of the filter material, maximize total volumetric flow rate, while minimizing the potential for clogging.

In some embodiments, the filter system performs affinity-based filtration. For example, in some embodiments the filter system comprises a component that prevents or discourages passage of an undesirable moiety (e.g. a contaminant) from the sample onto the porous membrane. For example, in some embodiments one or more components of the filter system (e.g. a filter layer) comprise a moiety that binds to a contaminant in the sample, thereby preventing the contaminant from passing through the filter system and onto the porous membrane. For example, biotin is a naturally occurring molecule in some biological samples which may be an undesirable contaminant in various analyte detection assays. Accordingly, in some embodiments at least one component of the filter system comprises a biotin-binding agent (e.g. avidin, streptavidin), which binds to biotin in the biological sample, thereby capturing the biotin within the filter system.

In some embodiments, the filter system performs both size-based and affinity-based filtration. For example, in some embodiments the filter system comprises pores (e.g. for size-based filtration) and moieties that bind to contaminants in the sample (e.g. for affinity-based filtration).

Figure 3:
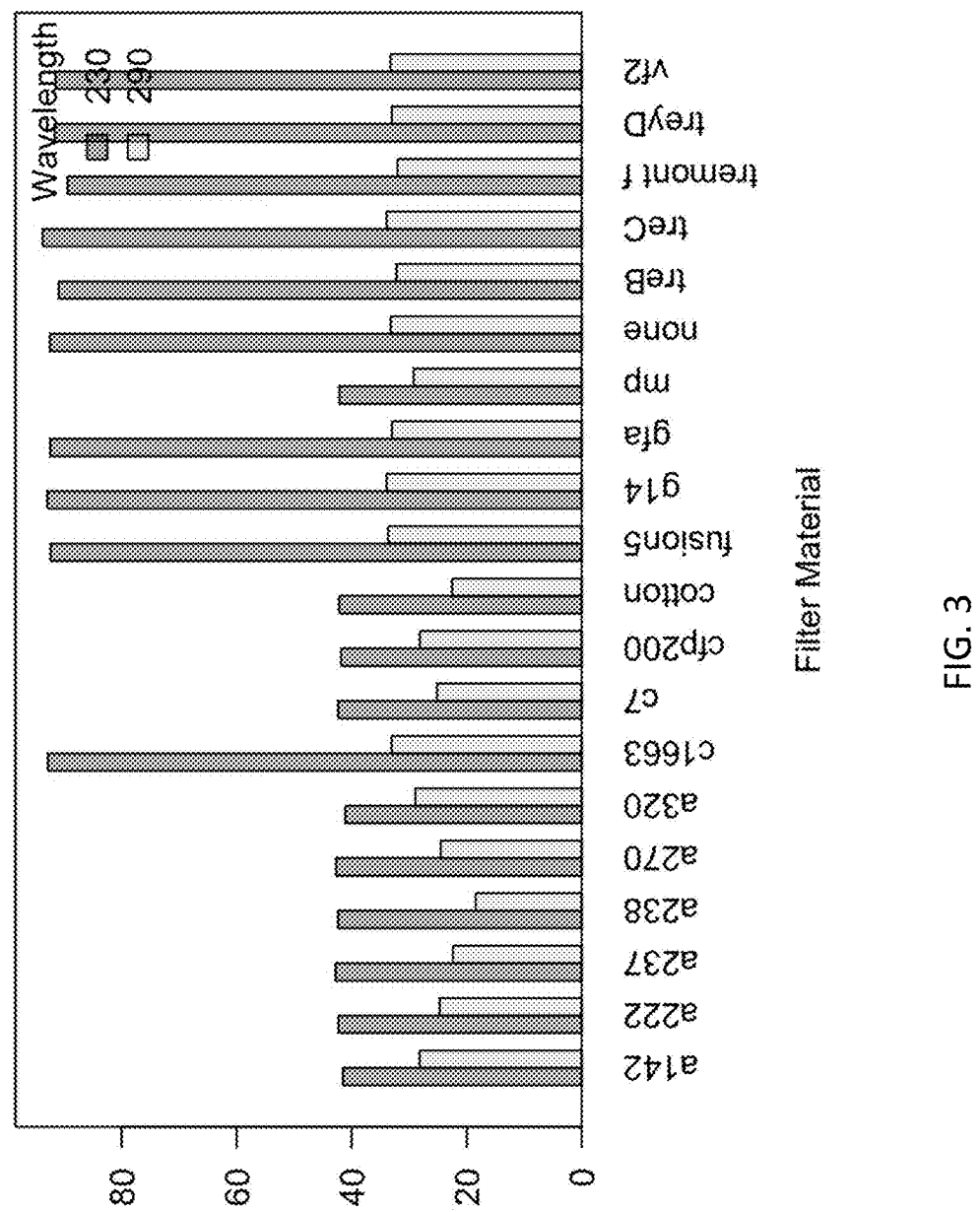
FIG. 3 and FIG. 4 show a comparison of filtering abilities of various filter materials and pore sizes.
Figure 4:
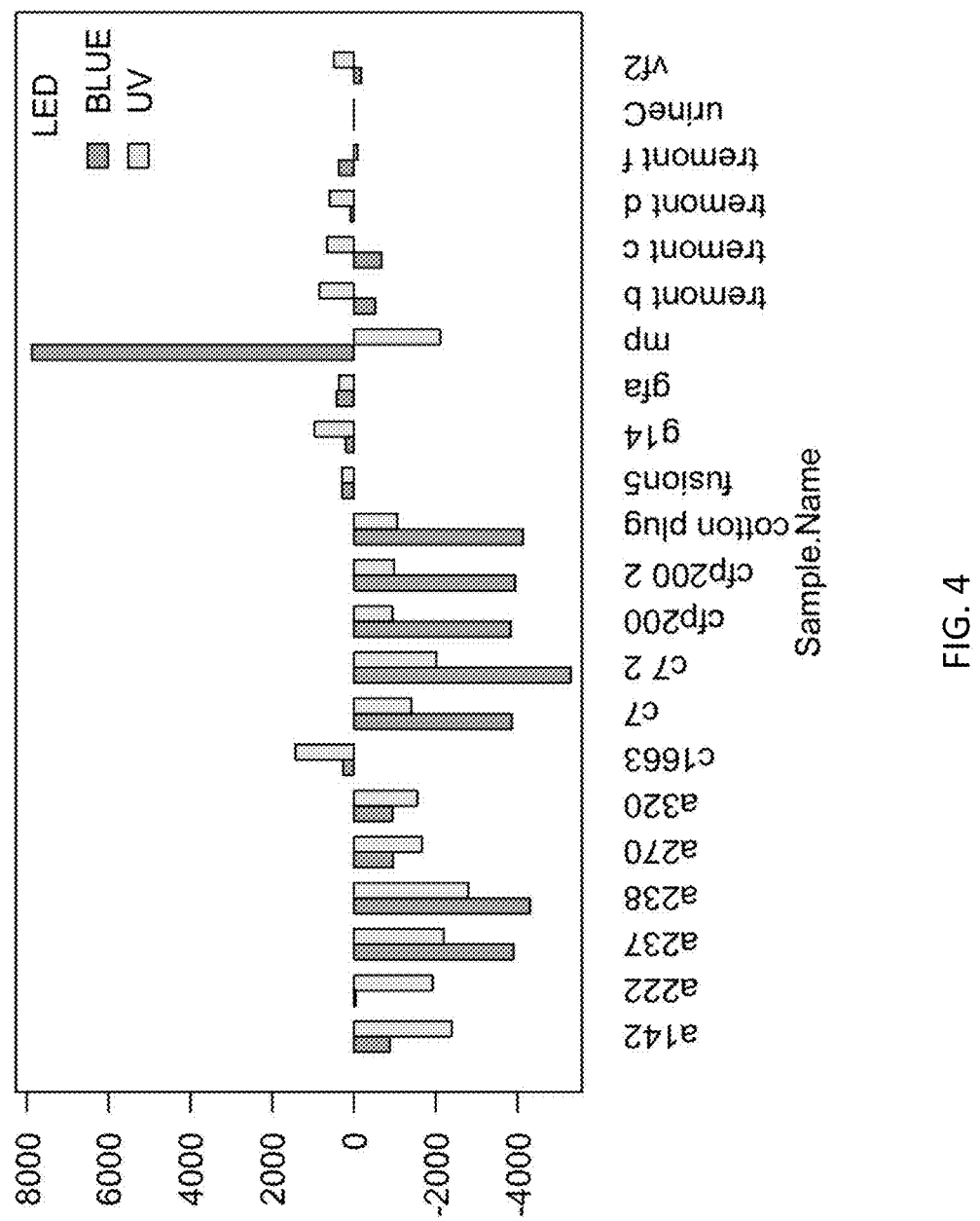
Figure 5:
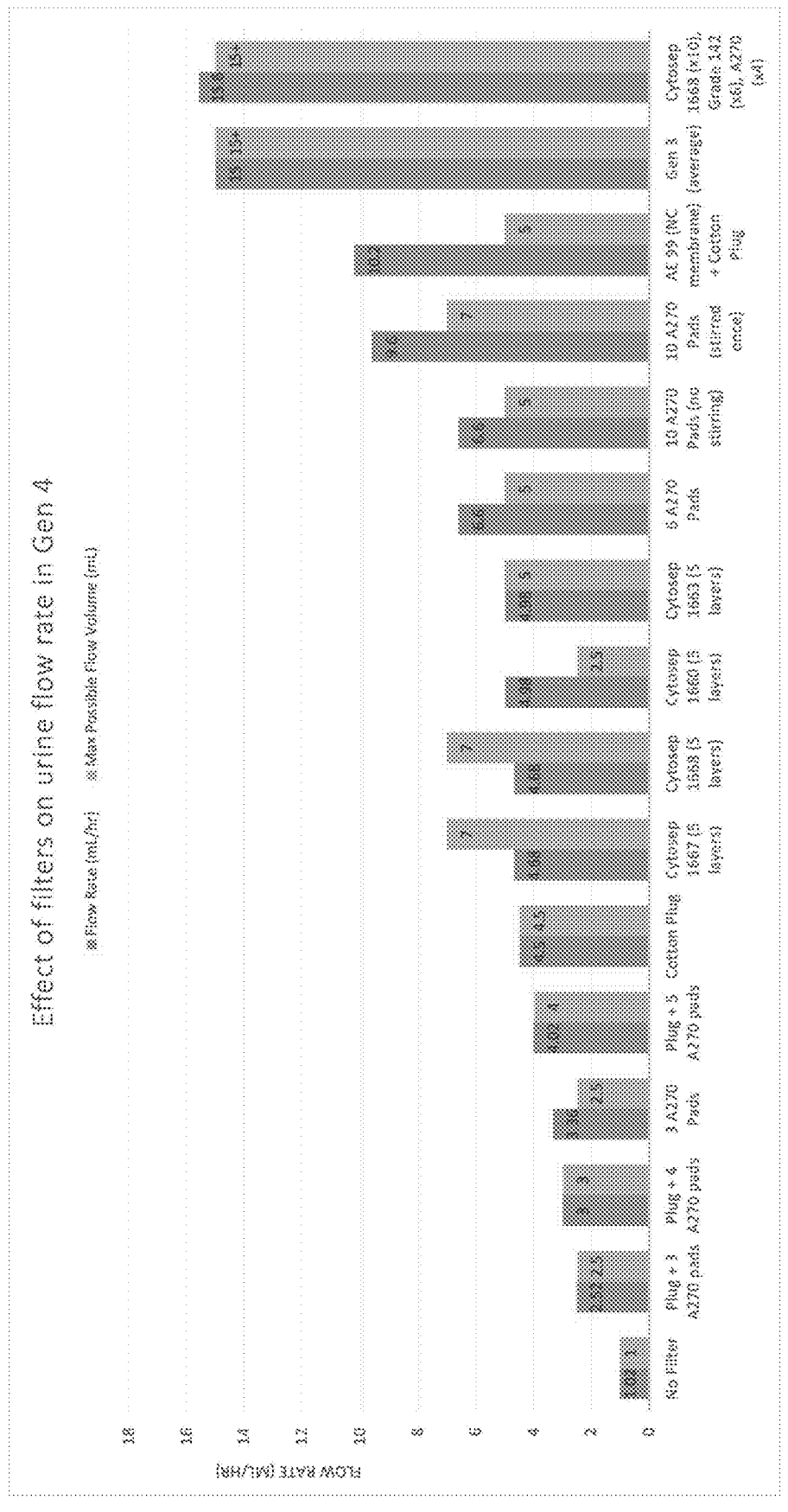
FIG. 5 shows a comparison of flow rates for different types of filters. Faster flow rates indicate the ability of a filter(s) to remove particles that would otherwise clog the nitrocellulose.
Figure 6:
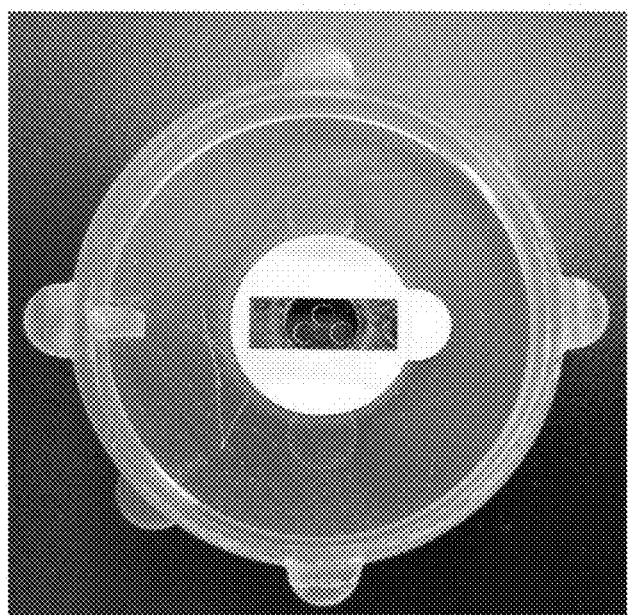
FIG. 6 shows an image of a component that may be present in the device described herein. The component is a multi-purpose adhesive layer. This layer is shown in this embodiment as a piece of scored, double-sided tape. The tape may be present between the porous membrane and the inner surface of the top component of the housing body, thereby serving to adhere the vertical flow assay components (e.g. the nitrocellulose membrane) to the device housing. Moreover, the tape is scored, thereby helping to direct the flow of liquid to the areas of the porous membrane containing the capture moieties. Thirdly, the tape is substantially impermeable to liquid (or highly resistant to flow or temporarily resistant to flow if the barrier dissolves), and thereby acts as a barrier and further assists in directing the flow of liquid to the desired regions within the porous membrane.

Each filter component (e.g. filter layer) may comprise any suitable material. In some embodiments, the filter material comprises a cotton material. In some embodiments, each filter component (e.g. filter layer) comprises the same material. In other embodiments, at least one filter component comprises a different material than at least one other filter component. For example, a first filter layer may comprise a different material than a second filter layer. Suitable filter materials include, for example, cotton materials, glass and/ or plastic fibers, sintered plastics, and synthetic meshes. Additional examples of suitable filter materials (e.g. filter system layer materials) include, but are not limited to, polytetrafluoroethylene (PTFE), mixed cellulose ester (MCE), and polyethersulfone (PES). For example, the porous material may comprise a polypropylene mesh, a polyester mesh, a nylon mesh, a nitrocellulose membrane, a mixed cellulose ester membrane, or a polyetheretherketone (PEEK) mesh. Furthermore, individual layers can be made of composites of individual materials (e.g., a combination of cotton and polyester fibers). Suitable filter materials include, for example, commercially available materials (e.g. from Ahlstrom) such as those tested in FIG. 3 and FIG. 4.

Each layer in the filter system may be of any suitable thickness to achieve the desired flow rate and filtration of particulates from the sample. In some embodiments, each layer is 0.1 mm-10 mm thick. For example, each layer may be 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, or 10 mm thick. In some embodiments, each material forms a 5 mm thick filtration layer.

The number of filter layers, the thickness of each filter layer, along with the optimal pore size, may be modified based upon the intended analyte to be detected in the sample and/or the volume of sample intended to pass through the filter system. For example, for larger analytes (e.g. proteins, viruses, or cells) it may be desirable to have larger pores to avoid unwanted separation of the analyte from the sample prior to detection. For other, smaller analytes, smaller pore sizes may be desirable. Generally speaking, cotton-based materials may be beneficial due to the ability to filter particulates from urine, affordability, biodegradability, and ease of manufacturing to the desired porosity and thickness.

Figures 20A, 20B:
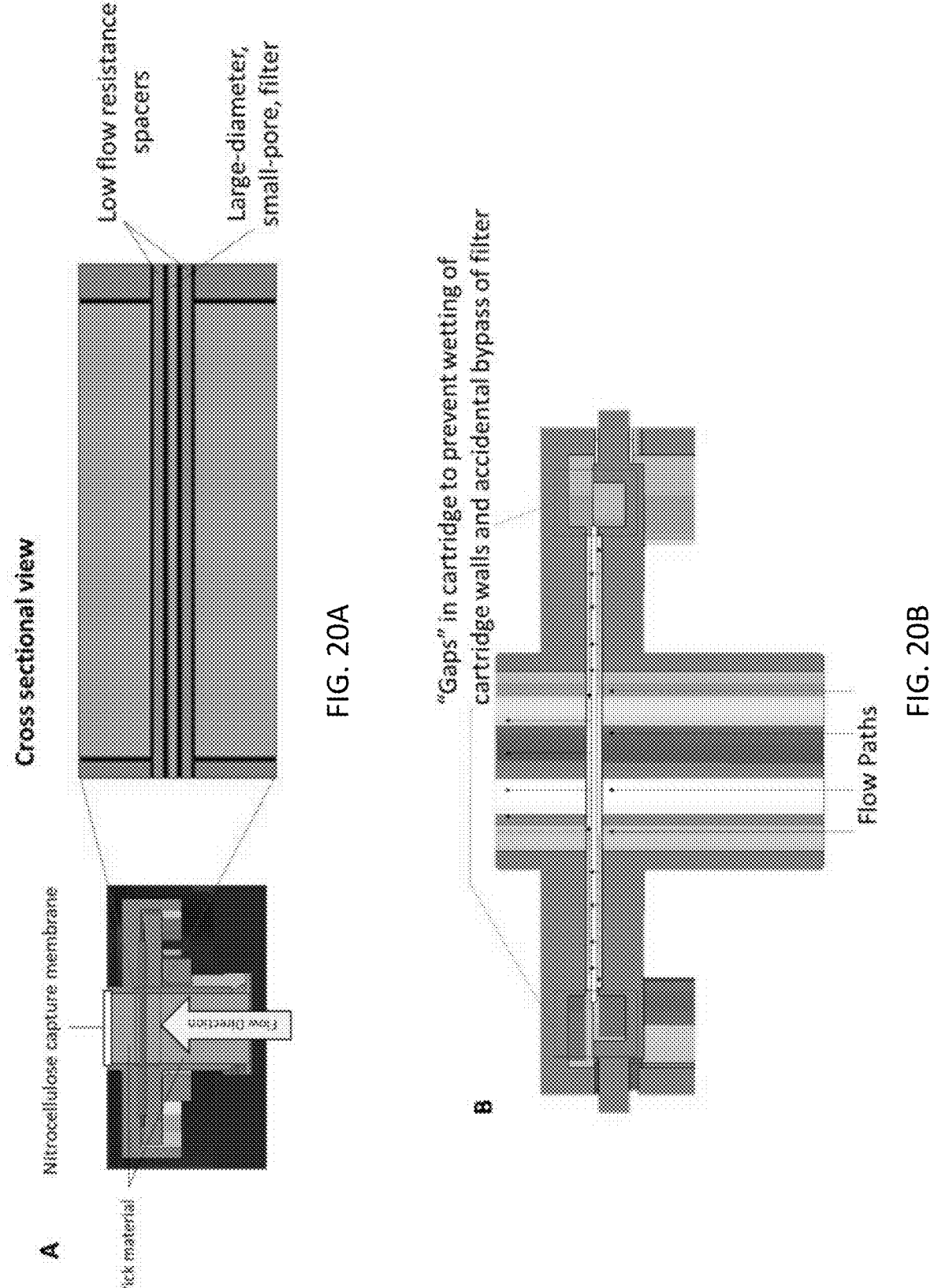
FIGS. 20A-20E show exemplary filter systems (e.g. filter cartridges) that may be used in the devices and methods described herein.
Figure 20D:
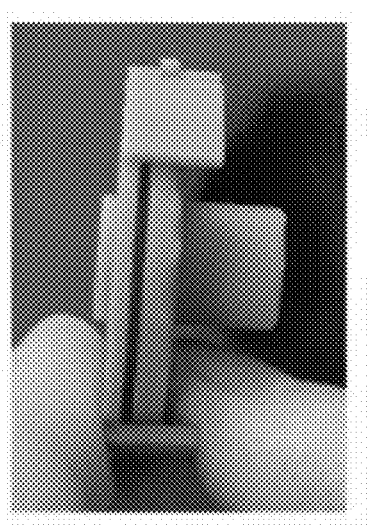
Figure 20C:
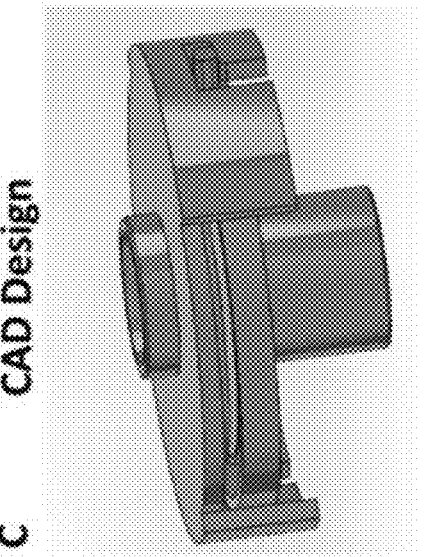
Figure 20E:
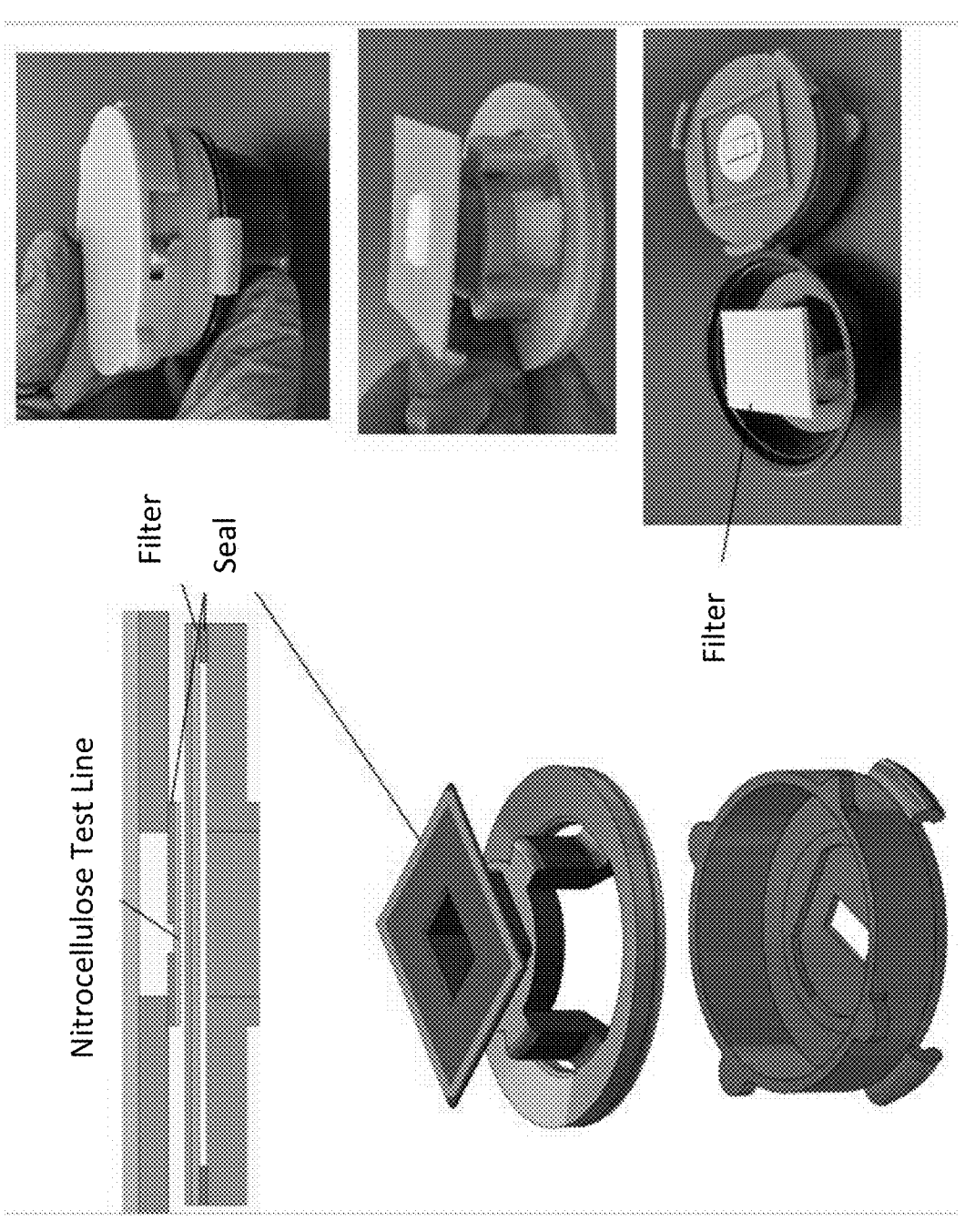
Figure 21A:
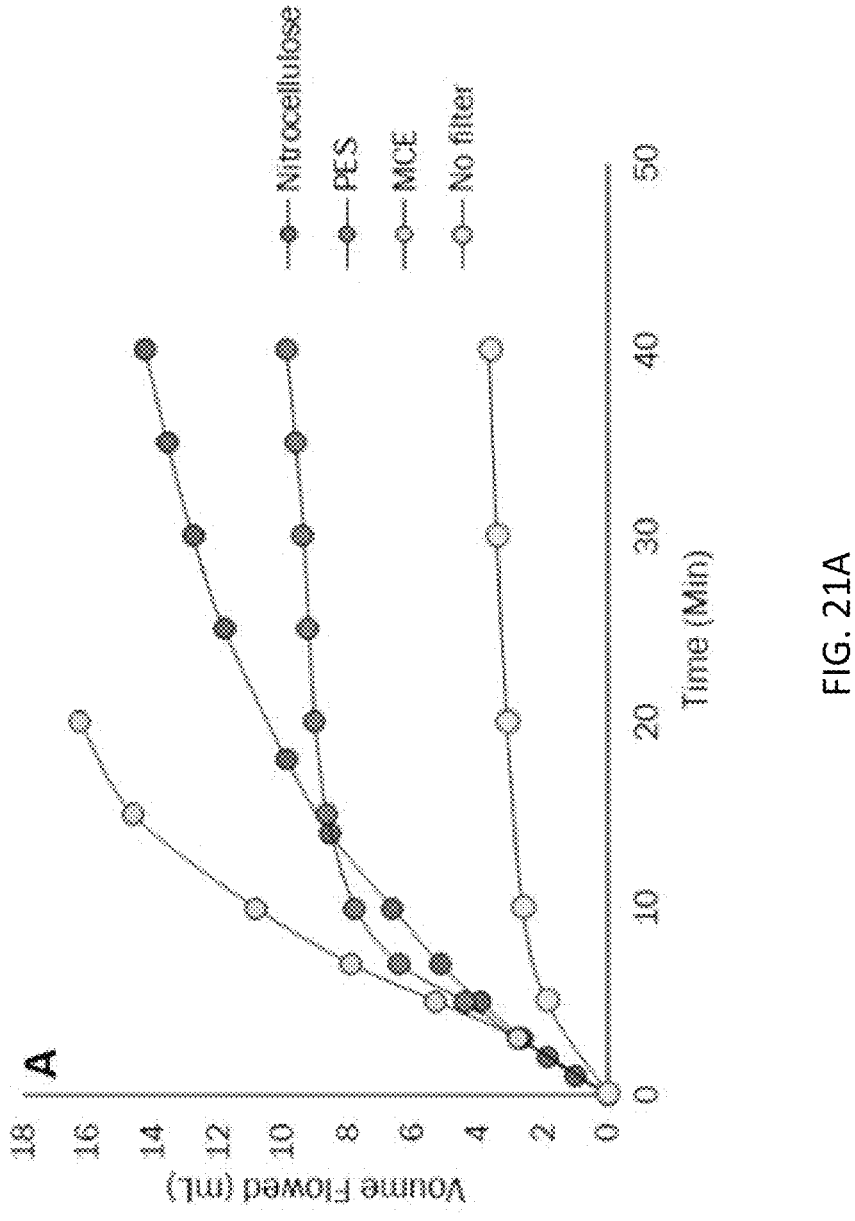
FIG. 21A-21B shows urine flow rates over time using the filter cartridge of FIG. 20 with different membrane filter materials, wicks, and spacers or wicking components.
Figure 21B:
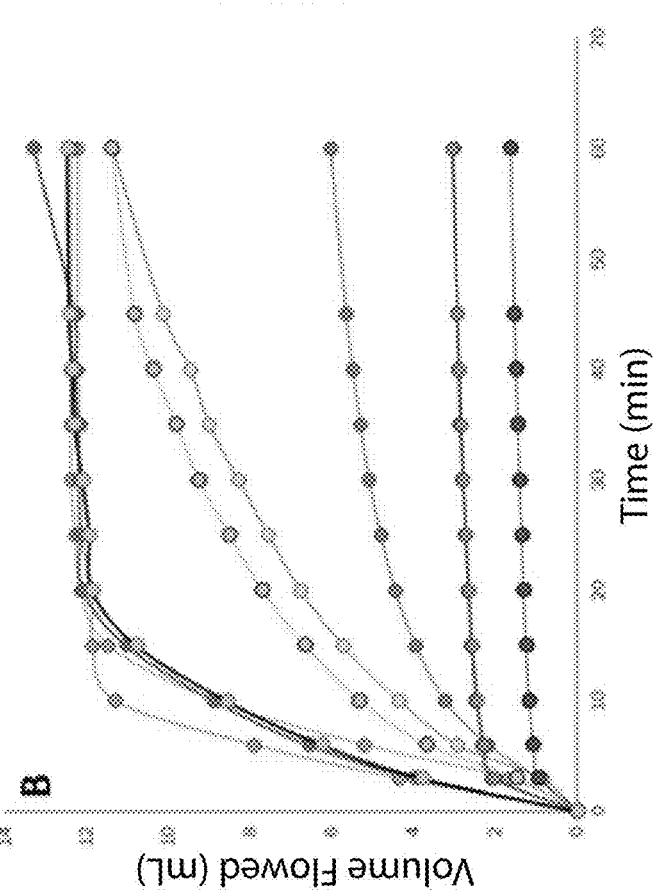

In some embodiments, the filter system fits tightly into its housing, so that it eliminates any leaking paths through or around the filter system. As a result, liquid that enters the system will be forced to pass through the filter system before entering the vertical flow assay. In some embodiments, the filter layers offer a level of resistance to flow, which can be modulated (e.g. by applying additional layers and/or removing filter layers) to set the flow rate of the liquid through the device at a desired rate. In some embodiments (e.g., a wicking device), portions of the filter system should not fit tightly into a housing, so that potential leak paths initiated by capillary action are avoided. In such cases, gaps or space between the housing and the filter or wicking materials are engineered to prevent unwanted capillary wetting that can circumvent flow through the filters. In some embodiments, the device comprises at least one component that prevents the liquid sample from circumventing the filter. In some embodiments, the at least one component that prevents the liquid sample from circumventing the filter is a barrier. In some embodiments, barriers (e.g., wax hydrophobic barriers, or adhesive tape) are used to prevent unwanted regions from wetness or capillary wetting that could circumvent filtration. For example, as shown in FIG. 20E, in some embodiments, one or more barriers (e.g. "adhesive seals", as shown in the figure), may be employed to prevent leaking around the edges of the device and facilitate flow through the filter.

In some embodiments, the filter system removes matrix components (e.g. contaminants) from a sample, such as a urine sample, thus eliminating interference from non-target substances in downstream detection. As used herein, the term "matrix" refers to non-target components within a sample, and is used interchangeably with the terms "contaminants" and "interferents". The term "matrix effect" refers to the effect of matrix (e.g. contaminants) within the sample on an assay, such as a detection assay for the target. Matrix can interfere with any step, component, or interaction within an assay. For example, matrix can bind to or interact with or cause aggregation of or otherwise hinder functionality of detection reagents (e.g., antibodies, enzymes, nanoparticles, porous materials, dissolved ions, etc.) or analytes (e.g., transient analyte-matrix complexes), thereby interfering with detection reagent binding to the target or enhancing non-specific binding of reagent to the target and reducing assay sensitivity or specificity. In some embodiments, the devices provided herein comprising a filter system reduce matrix effect and therefore improve sensitivity and accuracy of target detection assays performed using the devices described herein.

In some embodiments, the filter system comprises a porous material. In some embodiments, the filter system comprises a high protein-binding material (e.g. a material that binds a relatively high amount or percentage of proteins in a sample). Exemplary materials suitable for use in the filter system include, but are not limited to, mixed cellulose esters, polyethersulfone (PES), nylon, nitrocellulose, cellulose acetate, polyester track-etched membrane, polycarbonate track-etched membrane, cellulose, glass fiber, cotton, aluminum oxide, PTFE, PVDF, sintered plastics and mixtures or layerings thereof. In some embodiments, the filter system comprises a nylon membrane. A nylon membrane may be particularly suited for removing matrix from a urine sample. The nylon membrane may be positively charged, neutral, amphoteric, or negatively charged. In some embodiments, the filter system comprises a positively charged nylon membrane. In some embodiments, the filter system comprises a neutral nylon membrane. In some embodiments, the filter system comprises an amphoteric nylon membrane. In some embodiments, the filter system comprises a nylon membrane and the sample, when added to the device, flows substantially vertically through the nylon membrane.

In some embodiments, the filter system (e.g. nylon membrane) is positioned upstream of detection reagents. The terms "upstream" and "downstream" are used relative to the direction in which the sample will flow through the device when the device is in use, with "upstream" indicating that the sample would first contact the upstream component, and "downstream" indicating that the sample would contact the downstream component after first contacting/traveling through "upstream" component(s). The term "detection reagents" or "reagents for detection" is inclusive of any and all reagents that aid in capture and/or detection of an analyte. In some embodiments, the terms "detection reagents" refers reagents directly related to the capture and/or detection of a target in a sample (e.g. capture antibodies, detection antibodies, visually detectable conjugate particles, fluorescently labeled conjugate particles, amplification enzymes, enzyme substrates, primers, etc.). The term "detection reagents" is also inclusive of reagents that are not directly related to capture or detection, but are otherwise relevant to the conditions/environment needed or recommended for binding and/or detection of the target, such as buffering reagents to maintain proper pH, neutralizing reagents to condition the sample, surfactant/blocking agents to reduce non-specific binding, diluents, additives to prevent precipitation or normalize sample characteristics, stabilizing agents, crowding agents, etc.

In some embodiments, the filter system is positioned upstream of detection reagents within the device, and the detection reagents are dried onto one or more layers downstream of the filter system such that the sample flows through the filter system, which removes at least a portion of matrix from the sample, and subsequently contacts the downstream layer(s) and rehydrates the detection reagents. Exemplary locations of the device that may contain dried detection reagents downstream of the filter system are shown in FIG. 33B, FIG. 33C, and FIG. 33D. In some embodiments, one or more detection reagents are dried onto a porous material of the device downstream of the filter system. For example, in some embodiments one or more detection reagents are dried onto a wicking component of the device, downstream of the filter system (e.g. nylon membrane). For example, as shown in FIG. 33B the one or more detection reagents are dried into a portion of the wicking component, and at least a portion of the wicking component is housed between the filter system and the porous membrane containing one or more capture moieties. In such embodiments, the sample passes through the sample pads and onto the filter system prior to coming into contact with and reconstituting the dried detection reagents housed on the wicking component. Accordingly, the sample that comes into contact with the detection reagents is a filtered sample. The sample (e.g. the filtered sample+detection reagents) then passes through the remainder of the wicking layer and onto the porous membrane for subsequent detection of the target analyte. In some embodiments, one or more detection reagents are dried onto a porous membrane downstream of the filter system (e.g. nylon membrane). In some embodiments, one or more detection reagents are dried onto a wicking component of the device, and one or more detection moieties are dried onto a component downstream of the wicking component (e.g. a porous membrane), such that the sample passes through the filter system, contacts the wicking component and interacts with a first detection reagent, and subsequently travels through the wicking component and contacts the porous membrane and interacts with a second detection reagent. The position of the dried detection reagents relative to the filter system (e.g. nylon membrane) can vary to provide for rapid reconstitution, uniform distribution of rehydrated reagents, non-uniform distribution of rehydrated reagents, or slow release (e.g. slow rehydration) of the dried reagents, as desired for a given sample or assay type.

In some embodiments, one or more detection reagents are added onto/into the device in a region separate from the region used to add the sample. In some embodiments, one or more detection reagents are added onto/into the device in a region downstream of the region to which the sample is added, such that susceptible detection reagents mix with the sample only after the sample has been added to the device and at least partially filtered. For example, in some embodiments the device comprises one or more sample pads, and one or more reagent pads. The term "reagent pad" refers to a pad to which one or more detection reagents are added. The "reagent pad" is also referred to as a "conjugate pad" or a "buffer pad" herein. In some embodiments, detection reagents are added in liquid form to the reagent pad(s) and the sample is added to the sample pad(s). The reagent pad is distinct from the sample pad. Such an embodiment is shown, for example, in FIG. 33C. In the figure, the device comprises two sample pads and two reagent pads, identified by "buffer". This arrangement allows both the sample fluid and fluid with susceptible detection reagent to be delivered over the same timescale (i.e., metered in appropriately over time via control of flow pressures and resistance) into the downstream components of the assay. In some embodiments, the sample passes through the sample pad(s) onto the filter system, and travels substantially laterally through the filter system towards the location of the filter system downstream of the reagent pad(s). Accordingly, the sample passes through the sample pads without coming into contact with detection reagents which are added to the reagent pads, and the sample subsequently comes into contact with those detection reagents only after passing through at least a portion of the filter system. The sample and the detection reagents then come into contact and pass through the remaining portion of the filter system prior to contacting the porous membrane containing one or more capture moieties. In some embodiments, the arrangement of the sample pads and the reagent pads shown in FIG. 33C is reversed, such that the reagent pads are to the right and the sample pads are to the left. In such an embodiment, the sample and the detection reagents would travel separately through their respective pads, the detection reagents would travel through a portion of the filter system and subsequently come into contact with the sample in the area of the filter system underneath the sample pads. Sample and detection reagents would then pass through the remaining portion of the filter system onto the porous membrane containing one or more capture moieties. In some embodiments, as shown in FIG. 33D, the device comprises one or more sample pads and a reagent pad. In some embodiments, the sample is added to the upstream sample pad, and passes through the sample pad(s) and onto the filter system. The sample travels through the filter system prior to coming into contact with the reagent pad. The reagent pad may comprise dried detection reagents, which are reconstituted by coming into contact with the sample (which has already been at least partially filtered by the filter membrane). The sample (e.g. the filtered sample+detection reagents) then pass through the wicking component and onto the porous membrane containing one or more detection moieties.

The characteristics of the sample pad(s) and the reagent pad(s), if present in the device, can be modified to control the flow rate of fluid through the respective pads. In some embodiments, the volume and height of the sample pad(s) and the reagent pad(s) are similar such that liquid empties from the pads at a similar amount of time. In some embodiments, it may be desirable to have the detection reagents come into contact with the filter system earlier than the sample. In other embodiments, it may be desirable to have the sample come into contact with the filter system earlier than the detection reagents. The relative number, size, volume, material, porosity, etc. of the reagent pad(s) and/or sample pad(s) can be modified to achieve the desired flow properties through the device.

Generally, the materials downstream of the wicking layer are more hydrophilic and/or of smaller pore size than the sample pads and reagent pads, if present in the device. This composition promotes emptying of the sample pad due to higher capillary forces. In some embodiments, the sample pad(s) and reagent pad(s) comprise a relatively large pore size (e.g. roughly near the range of 10-1000 μm) and a relatively weakly hydrophilic material, such as polypropylene felt or treated polypropylene felt. Such material wets and fills weakly by capillary action but does not strongly retain fluid, allowing sample and liquid detection reagents to empty from the pads. Nylon and cotton are also considered examples of materials that can be manufactured with appropriate pore sizes for their hydrophilicity to be used as sample pads and detection pads. Likewise, surface chemistries and material pore-size of nearly any natural or synthetic fiber could be engineered to suit this purpose and are contemplated as feasible options for sample and detection pads. Generally, biodegradable materials are preferable to avoid release of chemicals during incineration or degradation in landfills.

In some embodiments, the filter system can be split such that the sample pad(s) and the reagent pad(s) have different filters underneath them (e.g. downstream of them). For example, filters having different flow resistances can be balanced with sample pad(s) and reagent pad(s) sizes to tune relative rates of emptying of each set of pads. For example a smaller pore size filter membrane could be used to slow emptying of a relatively small reagent pad such that the reagent pad and sample pad empty at similar times. In some embodiments, the filter components residing under the sample pad(s) and the reagent pad(s) may have different compositions. For example, a filter component under (e.g. downstream of) the susceptible detection reagents may not need to be able to remove interfering matrix and can thus be chosen for other characteristics (e.g., level of binding or passage of reagent components, flow resistance, durability for manufacturing, etc.).

In some embodiments, the filter system removes matrix (e.g. contaminants) from a sample, and also functions as a flow resistor. The filter system functioning as a flow resistor controls the total flow rate for a sample, thus improving/increasing interaction time between a target in the sample and detection reagents (e.g. antibodies). The filter system also improves the uniformity of flow vertically through the filter membrane. Specifically, given that fluid prefers to flow along the path of least resistance, a filter membrane with a relatively high flow resistance makes the resistance of all paths vertically through the membrane more similar to ensure more uniform flow which then improves sample interaction with detection components and visualization of results downstream. In some embodiments, without this added resistance of the filter membrane, fluid may pass out through the downstream edge and into the wicking layer without sufficiently traveling through the filter system.

In some embodiments, additional processes occur on device (e.g. within the device) to remove contaminants (e.g. matrix) from a sample. For example, in some embodiments precipitation, dissociation, liquid-liquid fractionation, or adsorption occur on-device to remove contaminants from a sample. These additional processes can be performed on a device comprising a filter system as an additional mechanism for removal of contaminants. For example, in some embodiments precipitation is used to remove interfering matrix from the sample on the device. There are many methods to precipitate substances (e.g., interfering substances) out of solution. In general, precipitation involves disrupting interaction of the substance with the bulk solvent (e.g., water). For example, disrupting interaction of the contaminant with the bulk solvent (e.g. water) can be performed by addition of salt, altering of pH, use of miscible solvents (e.g., ethanol and methanol for water), non-ionic hydrophilic polymers (e.g., dextran and polyethylene glycols for water), polyvalent metallic ions, flocculating polyelectrolytes (e.g., alginate and polyacrylic acid), denaturing conditions (e.g., change in temperature or pressure), or combinations thereof. However, use of precipitants can also adversely impact detection reagent and as such, in some embodiments precipitants are neutralized or removed prior to subsequent detection steps of an assay. In some embodiments, trichloroacetic acid (TCA) is used for precipitation and/or dissociation of sample components (e.g., matrix and target analyte(s)). TCA has a low pH, which should be neutralized with base before the sample is allowed to interact with sensitive detection reagents. In some embodiments, dried forms of chemical precipitants (e.g., TCA, polyvalent metallic ions) and neutralizing substances (e.g., neutralizing base, buffers, substrates with affinity for the precipitant for sequestration or chelating agents like EDTA for divalent cations) are incorporated into one or more layers of the device upstream of sensitive detection reagents to allow precipitation of interfering substances and neutralization/remediation of the precipitants before interaction of the sample with sensitive detection reagents. For example, in some embodiments dried forms of precipitants and neutralizing substances are incorporated into one or more wicking layers or other porous materials upstream of the layer containing sensitive detection reagents.

In some embodiments, liquid-liquid fractionation is used to remove/filter interfering matrix from the sample on device. For example, an aqueous two-phase system (ATPS) can be used with a sample to sequester contaminants into one phase of the aqueous ATPS. In some embodiments, an ATPS comprising PEG and a salt solution is used with a sample to sequester interfering proteins into the PEG fraction. In some embodiments, an ATPS is added to an upstream layer, and the denser salt solution flows vertically, downward, via capillary action into the downstream assay (e.g. the downstream porous layer containing capture and/or detection moieties for a target analyte). By limiting the amount of fluid that can be taken up via capillary action (e.g., via the size of the absorbent pad used to drive flow in the device), one can flow the salt fraction without flowing the PEG fraction. Similarly, a reservoir or vessel used to mix sample into the ATPS could be interfaced (e.g., via Luer-Loc, etc.) onto a device to supply fluid to the device components.

In some embodiments, adsorption to a substrate is used to remove interfering matrix from the sample on device or to induce denaturation and dissociation of components (e.g., matrix and target analyte(s)) upon adsorption. Use of a nylon filter membrane, as described above, or a depth-based filter column as a high capacity substrate on which to adsorb interfering substances as sample passes through are both effective methods of adsorption of interfering matrix to a substrate. Other geometries or methods to achieve such adsorption within the device can be used as an alternative or addition to the filter system. For example, in some embodiments highly adsorptive beads (e.g., polystyrene beads) are integrated into any layer (or more than one layer) of the device. For example, highly adsorptive beads can be integrated into one or more wicking layers or one or more other porous materials of the device to facilitate adsorption of matrix onto the beads prior to the sample coming into contact with one or more detection reagents. Any of the porous materials which often have significant surface area could be made with materials (e.g., nylon or even polypropylene for hydrophobic interferents) to promote adsorption/sequestration of particular substances or classes of substances. The diameter of an adsorptive bead and pore size of a substrate can be chosen to enable drying of the beads into the device for effective sequestration of interferents.

In some embodiments, filtration of at least one interfering substance is performed off device. There are myriad ways to implement various matrix filtration/remediation methods (e.g., adsorption, size-based filtration, precipitation, fractionation, denaturation, digestion, chelation, conversion, etc.). Some specific examples include use of syringe with an area-based nylon filter to adsorb matrix components while transferring sample onto/into the device. Similarly a gravity driven depth-based filter column could be used to pre-filter sample directly onto/into the device. Another example is polystyrene beads in a sample transfer vial optionally fitted with a filter to allow addition of sample into the vial, interaction of the polystyrene beads with the sample, and pouring of sample onto/into the device with the option of filtering beads during pouring. Another example is a rolled up nylon filter membrane (e.g. a filter membrane loosely rolled into a cylindrical shape) that is placed coaxially into a cylindrical sample transfer vial to allow sample to be poured into the vial, interact with the nylon membrane, and poured out onto/into the device. In another example, simple pouring between vials is performed to treat sample with TCA to precipitate interferents, followed by addition of neutralization buffer, followed by pouring of the neutralized mixture onto/into the device where precipitate is unable to flow through the device (e.g., via sedimentation or size filtration). Another example is an ATPS in a syringe where the syringe contains PEG and salt solution, the sample is aspirated, time is provided for separation of the PEG and salts, and the salt fraction is dispensed onto/into the device. Or, as a slight modification, the salt solution is diluted either within the syringe or in a separate vial prior to transfer onto/into the device. In some embodiments, filtration of contaminants can occur on device and off device.

In the aforementioned embodiments, discussion is largely centered around broad removal of classes of substances (e.g., proteins, lipids, cells, particles, nucleic acids, etc.). However, in some embodiments, mechanisms that are more specific to the particular interferent are used for filtration. For example, antibodies can be used to provide highly specific recognition of known interferents but also can be used for removing sub-classes of interferents such as sub-classes of antibodies (e.g., IgG, IgM, or IgA). Thus, substrates functionalized with binding partners of interferents can be integrated onto (e.g., via adsorption, charge, covalent chemistry, indirect linkers and spacer, etc.) reagents (e.g., beads or nanoparticle conjugates) or device materials (e.g., nitrocellulose or nylon membranes) to achieve specific (e.g. targeted) filtration of interferents. For example, ATPS polymers can be functionalized to perform specific sequestration to the polymer fraction. Such capabilities are valuable when the analyte of interest and interferent are a similar type of substance (e.g., protein target and protein interferent as opposed to a carbohydrate or nucleic acid target and protein interferent). Thus, in some embodiments, multiple different filtration mechanisms and/or generic and more specific binding mechanisms are used in concert to provide a range of filtration capabilities within an application or in different applications.

Figures 22A, 22B, 22C, 22D, 22E, 22F:
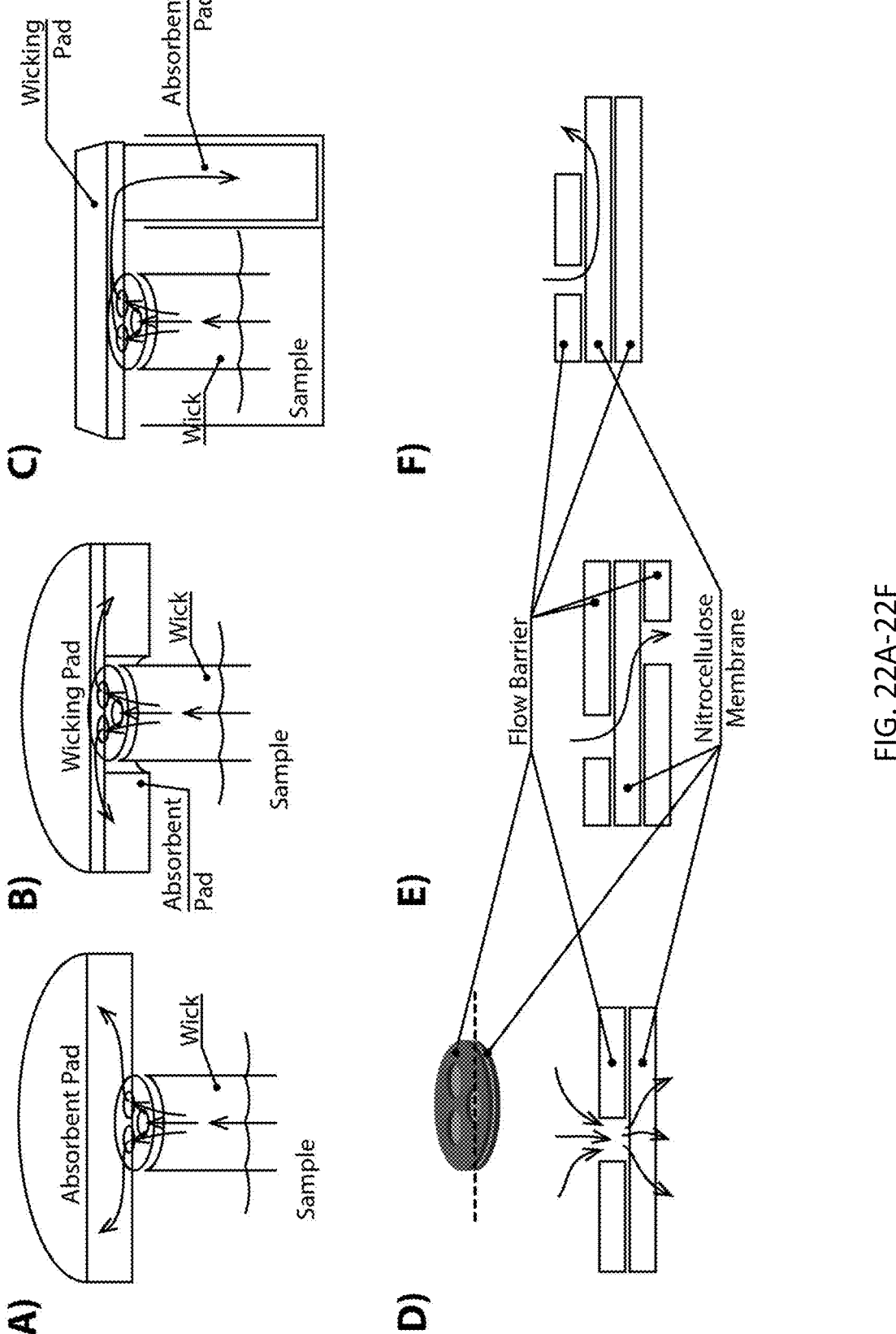
FIG. 22A-22F show exemplary flow paths that may be used in a device described herein.
Figures 23A, 23B, 23C:
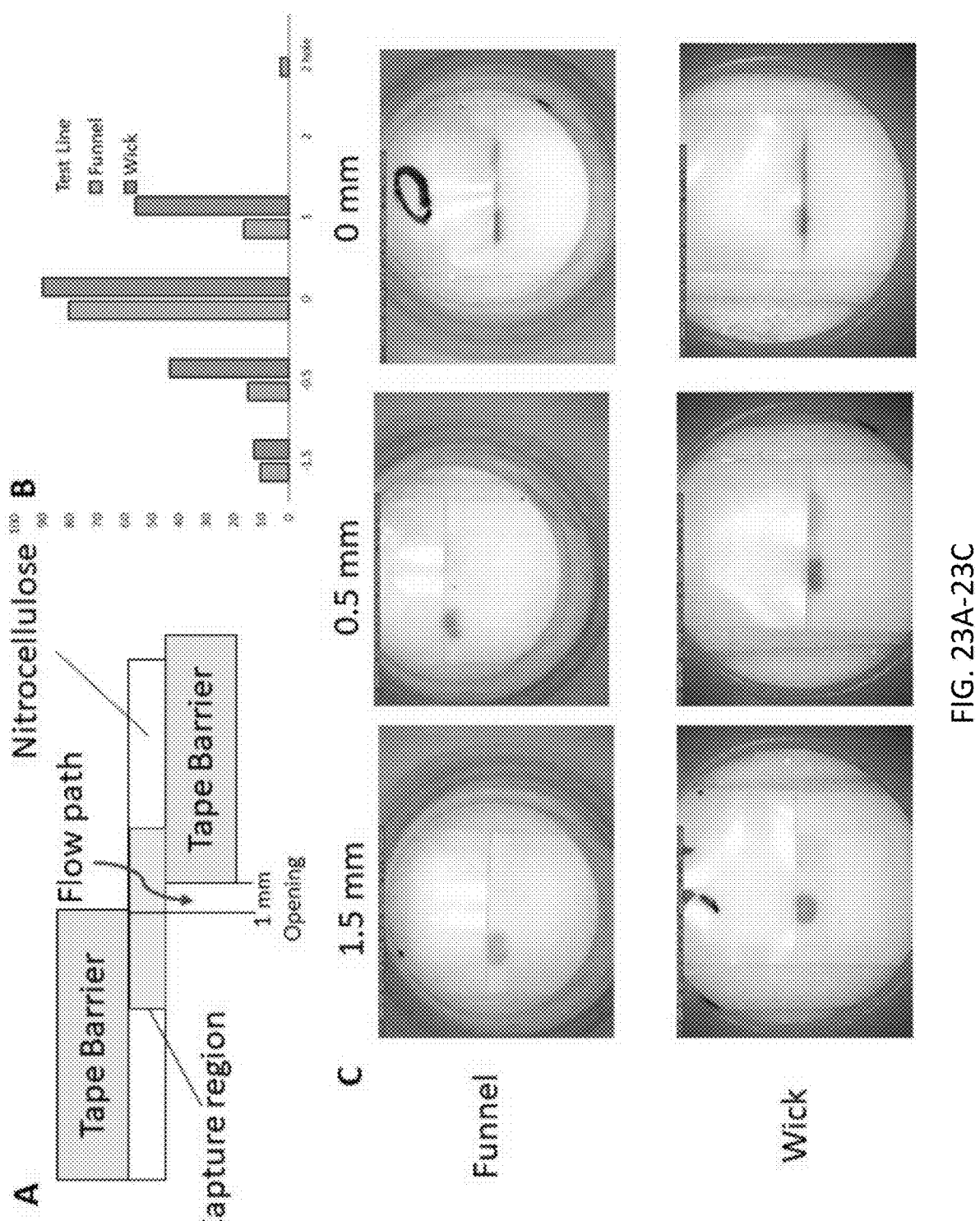
FIG. 23A-23C demonstrate that constricting flow through a more confined region increases residence time and overall signal is increased by roughly 10×.

For any of the embodiments described herein, the device further comprises a porous membrane containing one or more capture moieties held within a defined capture region of the membrane. In some embodiments, the porous membrane comprises two opposite sides. In some embodiments, each of the two opposite sides comprises at least one permeable region that allows passage of the liquid sample through the permeable region. In some embodiments, the liquid sample flows through the at least one permeable region on each of the two opposite sides at least once before flowing into the absorbent pad. In some embodiments, only one side of the porous membrane is permeable, requiring flow to enter and exit the same side as illustrated in FIG. 22F. Similarly to FIG. 22F, a wick pad and absorbent pad could be brought close to one another without a barrier in between to create a suitably short flow path (e.g., <5 mm) that enters and exits the same side of the porous membrane.

In some embodiments, the total length of the flow path through the porous detection membrane (e.g. the total length that the sample travels through the porous membrane prior to contacting the absorbent pad) is less than 5 mm. For example, in some embodiments the total length of the flow path through the porous detection membrane is less than 5 mm, less than 4.5 mm, less than 4 mm, less than 3.5 mm, less than 3 mm, less than 2.9 mm, less than 2.8 mm, less than 2.7 mm, less than 2.6 mm, less than 2.5 mm, less than 2.4 mm, less than 2.3 mm, less than 2.2 mm, less than 2.1 mm, less than 2 mm, less than 1.9 mm, less than 1.8 mm, less than 1.7 mm, less than 1.6 mm, less than 1.5 mm, less than 1.4 mm, less than 1.3 mm, less than 1.2 mm, less than 1.1 mm, or less than 1 mm.

The porous membrane may comprise any suitable material that allows for labeling of the membrane with antibodies (e.g. covalent labeling and/or non-covalent labeling either directly or indirectly such as via biotin-poly-streptavidin chemistry) and flow of liquid through the membrane. In some embodiments, the porous membrane is a nitrocellulose membrane. However, other suitable materials besides nitrocellulose may be used, including mixed cellulose ester, glass fiber, cellulose, nylon, and polyvinylidene difluoride (PVDF). For example, nitrocellulose may not be ideal for use with a flow through assay where >10 mLs of sample is processed in remote settings where nitrocellulose may clog. Additionally, nitrocellulose may lack stability in uncontrolled humidity environments, and at undesirable temperatures. Glass fiber, cellulose, nylon, and PVDF may be more stable than nitrocellulose in such conditions.

The capture region (e.g. the defined region containing the one or more capture moieties) may be in any suitable place on or within the porous membrane. Typically, the capture region is placed such that easy visualization of results can be achieved following completion of the assay. In some embodiments, the porous membrane further comprises one or more capture moieties. The capture region facilitates concentration of the analytes at a set point within the device. Accordingly, the process of capturing the analytes at the capture region is also referred to herein as "preconcentration". Preconcentrating the target analyte (e.g., from a relatively large volume of sample) within the same device used for detecting the analyte presents an innovative approach for rapid, straightforward testing of biological samples. In addition, preconcentrating the sample within the same device used for detecting the analyte represents a mechanism to detect an analyte with high sensitivity and specificity in large volumes of fluid.

Preconcentration can be achieved in multiple ways. In some embodiments, target analyte can be captured into the capture region prior to introduction of detection moieties (e.g., molecules or particles). Target analyte that was previously dispersed throughout the sample is now concentrated in the roughly sub-microliter volume of the capture region. For example, target analyte that was previously dispersed throughout the liquid sample having a volume of around 10 mL can be concentrated in the roughly sub-microliter volume of the capture region, increasing concentration of the target analyte multiple orders of magnitude. The increased concentration of target analyte within the capture region can then facilitate rapid and efficient binding of detection molecules or particles for diagnostic testing.

In some methods of preconcentration, a detection moiety can be mixed with the sample for a more complex and dynamic preconcentration approach. In some embodiments where the detection moiety is a bead (e.g. a latex bead) functionalized with antibody to the target analyte, the bead can either bind target analyte that has already been captured in the test region, or can directly bind target analyte in solution before it reaches the capture region. Thus, analyte within the test region may be (i) bound to the test region directly, (ii) be bound on a detection moiety captured in the capture region, or (iii) be simultaneously bound by the detection moiety and the capture region. This also means that binding of detection particles in the detection region can indirectly accumulate additional antibody into the capture region that is specific to the target of interest, thereby increasing binding capacity and improving binding kinetics of the capture region. Likewise, exposed target that is bound on the detection particle can facilitate capture of additional detection particles through capture of target analyte already bound to detection particles (i.e., facilitating particle aggregation in the capture region relative to aggregation via random interactions in solution), or physical entrapment of subsequent detection particles by reducing the effective pore-size of the capture region. Premixing of the detection particle can also provide more time for binding of the target analyte when binding kinetics are a limiting factor. For some antibodies and targets, methods that allow premixing of the detection particle with the sample prior to reaching the capture region may significantly increase sensitivity.

Premixing of detection moieties with the liquid sample can be done in many ways. In some embodiments, detection moieties can be in solution and mixed with the liquid sample prior to addition to the device. In some embodiments, the detection moiety can be pre-loaded into the device reservoir prior to addition of the sample. In some embodiments, the detection moiety can exist as a lyophilized powder that mixes with the sample upon sample addition. In some embodiments, the detection moiety can be dried into a wick or filter layer of the device where mixing occurs when sample begins to flow through the device. In some embodiments, methods can also be used to control the release kinetics of the detection moieties during rehydration as sample flows (e.g., via addition of sucrose into the media used to dry the particles into a porous material).

In some embodiments, the capture moieties are capture antibodies that bind to the analyte of interest. In some embodiments, the capture antibody can be conjugated (e.g., via adsorption, covalent chemistry, or indirectly via biotin-streptavidin chemistry) to the porous membrane. For example, the capture antibody can be conjugated to a nitrocellulose, glass fiber, cellulose, nylon, or PVDF membrane. In some embodiments, the capture moieties are bound to a solid support, and the support is suspended in the porous membrane. For example, the capture moieties may be bound to beads (e.g. polystyrene beads), and suspended in a porous membrane such as a glass fibrous membrane.

In some embodiments, the porous membrane further comprises one or more detection moieties. In other embodiments, detection moieties added to the sample or to a component of the device following capture of the one or more analytes by the porous membrane.

In some embodiments, the detection moieties are detection antibodies. The detection moieties (e.g. detection antibodies) comprise a detectable label (e.g. gold nanoparticles). In some embodiments, the detection antibodies bind to the analyte and the analyte binds to the capture antibodies, such that the detectable label is seen in the defined capture region of the membrane when the analyte is present in sufficient levels within the sample.

In some embodiments, the porous membrane comprises multiple capture regions. For example, the assay may be multiplexed such that multiple analytes of interest can be detected simultaneously. In such embodiments, each capture region may comprise a distinct capture moiety or mix of capture moieties. Each capture region thereby enables concentration of distinct analytes or combinations of distinct analytes. Accordingly, a multiplex assay for multiple analytes can be effectively performed, wherein each analyte is preconcentrated at a separate location within the device. For example, a first capture region can comprise a first capture antibody for a first analyte of interest, a second capture region can comprise a second capture antibody for a second analyte of interest, etc. Any suitable number of capture regions may be employed.

In some embodiments, the porous membrane further comprises at least one control region. In some embodiments, the porous membrane comprises a single control region. In some embodiments, the single control region can comprise multiple species of capture moieties (e.g. a first type of capture moiety to verify that sufficient volume of urine has passed through the porous membrane, and a second species of capture moiety to demonstrate that a capture antibody is working properly, etc.). In some embodiments, the porous membrane comprises two or more control regions. In some embodiments, a control region comprises a capture moiety, such as a control antibody, that is indicative that sufficient volume of sample (e.g. urine) passed through the porous membrane to enable detection of the analyte of interest, if present in the sample. For example, the control region may detect one or more control proteins that are expressed in urine regardless of whether or not the analyte of interest is present in the urine sample. In some embodiments, a control region may have one or more capture moieties that demonstrate that all biochemical components (e.g. antibodies with detection label) are present and/or functioning properly. In some embodiments, the detection moiety for the control provides a signal that is distinct from the signal for the detection moiety that binds to the analyte of interest. In such embodiments, the control region and the capture region can overlap spatially yet the signal from each moiety can be detected separately. For example, the control region and the capture region may overlap, but may utilize different detection moieties that can be differentiated upon assessment of the regions for the presence and/or absence of the detectable signal. For example, different fluorescent signatures (e.g. different excitation and emission wavelengths) may be generated for the capture region and the control region. In some embodiments, the control region and the capture region are spatially distinct. In such embodiments, the detection moieties can be detected separately even if they utilize the same detection label (i.e., produce the same type of signal). Use of spatially separated capture regions for target analytes and control analytes allows the signals from each detection moiety to be analyzed independently of one another (i.e., binding of target and detected signal at one location does not influence binding of another target or detected signal at any other locations. This contrasts with traditional lateral flow assays where sample would typically flow through one capture region, potentially being perturbed, before reaching the next. Thus, spatially multiplexed detection of target analytes in a vertical flow assay has significant advantages over multiplexing in a traditional lateral flow assay.

In some embodiments, the device further comprises a component to direct flow of liquid to the capture region(s) and the control region, if present in the porous membrane. For example, the component to direct flow of liquid into the desired regions on the porous membrane may comprise a physical barrier with areas of permeability to guide the flow of liquid into/onto the desired regions. For example, the device may comprise an liquid impermeable layer containing one or more openings, wherein the one or more openings are placed in a suitable position relative to the capture region(s) and the control region such that liquid is forced to travel through the one or more openings and into the capture and/or control regions of the porous membrane. An example of this type of embodiment is the scored tape shown in FIG. 1. However, other methods for spatial patterning of flow permeability may be used to appropriately direct the flow of liquid to the desired areas. As an alternative or addition to a physical component to direct flow of liquid, flow-resistant areas may be incorporated into the porous membrane itself. For example, wax may be printed directly on the porous membrane itself may be used to generate flow resistant areas away from the capture and/or control regions, and the capture and/or control regions may be conducive to flow. Accordingly, liquid will generally be guided to the more permeable regions, thereby passing preferentially or selectively through the capture and/or control regions. The use of physical barriers and/or flow resistant areas helps to reduce the volume of liquid necessary to pass through the porous membrane in order to facilitate binding of the analyte of interest to capture moieties within the membrane. Likewise, limiting the capture region size increases the final density of captured target and/or detection moieties for increased signals.

In some embodiments, the device comprises one or more microchannels. In some embodiments, one or more microfluidic channels are used to interface with porous materials as a means to direct fluid to desired regions of the porous membrane. In some embodiments, the device comprises one or more microfluidic channels that transport the liquid sample to the capture region of the porous membrane. In some embodiments, the device comprises one or more microfluidic channels that transport the liquid sample to the capture region of the porous membrane, and one or more microfluidic channels that transport the liquid sample to the control region of the porous membrane. In some embodiments, the microchannel(s) is/are clear, providing the ability to directly view potential test and/or control results/indicators. In some embodiments, the microfluidic channel comprises a mechanism for air escape. In some embodiments, the mechanism for air escape is a hole, a flap, a valve, or an air-permeable region. In some embodiments, the microfluidic channel is in communication with atmospheric pressure (e.g., directly or indirectly via features such as a hole, a porous material, another channel, etc.), providing a means to equalize pressure between the inside and outside of the housing of the device when sealed while also minimizing the release of potential sample odors through the small nature of the channel upon use. In some embodiments, the microfluidic channel is in communication with atmospheric pressure to facilitate capillary filling of the channel with liquid sample by allowing release of potentially trapped air/gas. Use of a hydrophilic material or surface treatment within the channel can be advantageous to promote capillary filling but also to encourage fluid to remain within the channel during the test, thereby supplying adequately uniform coverage of fluid over the potential test and/or control results/indicators. Indeed, other standard microfluidic engineering techniques can be used to alter functional behavior of the microchannel (e.g., variable cross-sectional geometry or variable hydrophobicity/hydrophilicity via microstructured surfaces or chemical treatments to promote control/pinning of fluid interfaces, hydrodynamic focusing, microfluidic mixing, multiplexing, etc.).

Generally speaking, when a filter system is present in the device the sample passes through the filter system prior to contacting the porous membrane. In some embodiments, this occurs because the sample is applied to the top of the device (e.g. through an opening, through a funnel, etc.) and travels through the filter system prior to contacting the porous membrane. In some embodiments, this occurs because the sample is wicked through the filter system prior to contacting the porous membrane. For example, the sample may be wicked substantially laterally through the filter system prior to contacting the porous membrane. As another example, the sample may be wicked substantially vertically through the filter system prior to contacting the porous membrane.

In some embodiments, the sample may be wicked from a reservoir containing the liquid sample and flows substantially laterally along at least a portion of the wick prior to flowing in a substantially vertical fashion through the filter system. In some embodiments, the sample flows through a first wicking component prior to contacting the filter system and flows through a second wicking component after flowing in a substantially vertical fashion through the filter system. Regardless of the method by which the sample travels through the device, passing through the filter system prior to contacting the porous membrane containing the capture and detection moieties removes unwanted contaminants from the liquid sample (e.g. urine sample), thereby facilitating flow of sample through the device, preconcentration, and detection of the analyte of interest.

In some embodiments, the component to guide the flow of liquid to the desired areas of the membrane (e.g. the capture region(s), the control region) may be positioned within the device such that the liquid sample passes through the filter system prior to contacting the component to guide the flow of liquid. For example, a liquid impermeable layer containing one or more openings may be placed within the device such that the liquid sample passes through the filter, then passes through the one or more openings of the liquid impermeable layer prior to contacting the porous membrane.

In some embodiments, the device further comprises at least one absorbent pad. The at least one absorbent pad may comprise any suitable absorbent material. In some embodiments, the absorbent pad is a cotton-based material. In some embodiments, the absorbent pad is a cellulose-based material. The size and shape of the absorbent pad should be selected such that it fits within the intended region of the device in a suitable fashion to apply adequate pressure to the other components of the device to facilitate transfer of liquid into the absorbent pad. The at least one absorbent pad may be placed in any suitable location within the device to absorb sample liquid and/or to help direct the flow of liquid through the device. In some embodiments, the device comprises multiple absorbent pads, placed in various locations throughout the device.

In some embodiments, the device further comprises at least one wicking component. A "wicking component" may also be referred to herein as a "wick", "wicking layer", or "transport layer". The at least one wicking component may comprise any suitable material capable of pulling liquid through the wicking component, such as by capillary action. For example, in some embodiments the wicking component comprises polyester, polypropylene, nylon, or a similar material. For example, the wicking component may comprise a layer of material, such as a layer of polyester, polypropylene, nylon, or a similar material. Accordingly, in some embodiments the wicking component is referred to herein as a "wicking layer" or a "wick layer". In some embodiments, the wicking component comprises more than one layer of material. In some embodiments, the wicking component is used in a wicking device to induce flow of the liquid, typically vertically, from a source location to a destination. For example, a wicking component may be positioned beneath the porous membrane, such that the wicking component induces flow of the liquid sample against the force of gravity from the sample reservoir onto the porous membrane (e.g. by capillary action). As another example, a wicking component may be positioned beneath the filter system, such that the wicking component pulls the liquid sample onto the filter system. The liquid may subsequently travel through the filter system, optionally onto a second wicking component, and into contact with the porous membrane. In some embodiments, multiple wicking components are used. In some embodiments, a single wicking component is used. In some embodiments, liquid that is wicked onto the porous membrane is then absorbed by the absorbent layers. Thus, use of a wick allows the liquid sample to pass from the sample reservoir, through the wicking component(s), filter system, and porous membrane to allow the assay to be performed with or without the assistance of gravity or potentially against gravity.

In some embodiments, one or more wicking components are used to induce the flow of liquid in a substantially lateral flow path from a source location to a destination. In some embodiments, the flow of the liquid sample through at least a portion of a wicking component is substantially lateral. In some embodiments, the device comprises a first wicking component and a second wicking component separated by a filter system. In some embodiments, the flow of the liquid sample through at least a portion of the first wicking component and at least a portion of the second wicking component is substantially lateral. In some embodiments, the device is configured such that a portion of the first wicking component, a portion of the filter system, and a portion of the second layer overlap with one another. An area of overlap between two or more materials within the device is also referred to herein as a "junction" or "interface". In some embodiments, a "junction" or "interface" is described as an area of the device wherein two or more materials are stacked vertically with respect to one another. In some embodiments, the flow of the liquid sample through the junction is substantially vertical. In other words, the liquid sample flows substantially vertically through the portion of the first wicking component, the filter system, and the portion of the second wicking component that overlap with one another. In some embodiments, following traveling in a substantially vertical flow path through the junction, the liquid travels in a substantially lateral fashion through a portion of the second wicking component that does not exist at the junction and onto the porous membrane. In some embodiments, the surface area of the junction (e.g. the amount of material that overlaps) can be modulated to optimize flow of the liquid sample through the junction.

One or more wicking components may also be used to assist sample flow or be the primary driver of sample flow through the membrane via capillary or surface-tension-based forces. Such wicking components may be used in wicking devices, hybrid devices, and in gravity assisted devices. In some embodiments, the wicking material comprises a soft, compliant material with relatively low fluid resistance. In some embodiments, the filter and the absorbent pad are quite large compared to the capture region on the porous membrane. Accordingly, the wicking component may assist in pulling fluid from the relatively large area of the filter (e.g. 20-50 mm in diameter) to the smaller capture regions (e.g. about 2 mm in diameter) on the porous membrane, and/or from the relatively small capture regions of the porous membrane (e.g. about 2 mm in diameter) to the relatively large area (e.g. 20-50 mm in diameter) of the absorbent pad.

Additionally, the filter system and/or the wicks, if present in the device, should not significantly deplete the analyte of interest and should not bind to or substantially inhibit a detection moiety from reaching the porous membrane. For example, the filter system and/or the wicks may comprise one or more materials or added agents that prevent nonspecific adsorption of the target analyte. For example, one or more agents, such as one or more surfactants or blocking agents (e.g. proteins, BSA, casein) may be added to the filter system and/or the wicks to prevent nonspecific adsorption of the target analyte into the filter material and/or wicking material. As another example, materials with different hydrophobicity such as polypropylene or glass fibrous materials may be selected that do not promote adsorption of the analyte of interest.

The selection of the location of the absorbent pad(s) and/or wicking component(s) may depend on the intended flow path of the liquid sample through the device. Exemplary flow paths are shown in FIG. 22A-22F. Any of the flow paths and/or arrangements of components described therein may be used. In some embodiments, multiple wicking components may be employed to assist in diverting the flow of liquid in the intended manner. Generally speaking, it may be desirable to place one or more absorbent pad(s) and one or more wicking components in suitable locations within the device to facilitate flow of liquid from a sample reservoir, through the porous membrane, and into absorbent pads. This may be accomplished by using one or more absorbent pads to control the flow path of liquid sample, such as in a lateral fashion across the device, away from the membrane. Alternatively, this may be accomplished by using a wicking material to allow fluid to pass from the porous membrane to an absorbent pad.

In some embodiments for a wicking device, the absorbent pad may be placed above the porous membrane, such that the liquid sample is driven upwards in a mostly vertical fashion through the wicking material, through the porous membrane, and into the absorbent material. Liquid sample traveling through the porous membrane may be pulled into the absorbent material along a path that has a non-zero directional component perpendicular to the plane of the membrane (i.e., a "vertical" flow path). In some embodiments, the porous membrane may be smaller than the housing body of the device, leaving space such that an absorbent pad or multiple absorbent pads may be placed around the porous membrane. For example, the porous membrane may be a circular shape with a smaller diameter than the diameter of the housing body, and an absorbent pad or multiple absorbent pads may be placed in the gap between the outer edge of the porous membrane and the inner surface of the housing body (e.g. similar to a donut, where the hole of the donut is the porous membrane). Such an embodiment would generate a fountain-like flow path, where liquid is pulled up by a wicking component onto the absorbent membrane, and then radiating in an outward and downward fashion onto the absorbent pad(s). Such an embodiment might be useful for reducing pressure that may otherwise impede upward flow of the liquid onto the porous membrane.

In some embodiments, at least one absorbent pad is placed next to the porous membrane and a wicking material is placed such that a flow path is created between the porous membrane and the absorbent pad by the wicking material. Such an embodiment, when used for example in a wicking device, would provide a path for fluid to flow through the membrane, then horizontally away from the porous membrane and into the absorbent pad. Such configurations may be necessary to achieve user-friendly configurations of the device (e.g., easier to handle or interface with digital readers). In some embodiments, the device may also employ various components to cause local transverse flows that can be used to increase flow resistance compared to purely vertical flow. In contrast, such a component may limit transverse flow to a relatively short distance compared to purely lateral flow assays, thereby reducing flow resistance relative to traditional lateral flow assays. Although these transverse flow patterns may occur, overall the flow of the liquid through the device is referred to as "vertical" flow. In some embodiments, flow barriers may be used to induce local transverse, or partially transverse flows. For example, alternating layers of permeable and impermeable layers can be utilized to create complex paths for tuning flow path and resistance to suit various needs. In some embodiments, the total length of the flow path through the porous detection membrane (e.g. the total length that the sample travels through the porous membrane prior to contacting the absorbent pad, including lateral flow and transverse flow) is less than 5 mm. For example, in some embodiments the total length of the flow path through the porous detection membrane is less than 5 mm, less than 4.5 mm, less than 4 mm, less than 3.5 mm, less than 3 mm, less than 2.9 mm, less than 2.8 mm, less than 2.7 mm, less than 2.6 mm, less than 2.5 mm, less than 2.4 mm, less than 2.3 mm, less than 2.2 mm, less than 2.1 mm, less than 2 mm, less than 1.9 mm, less than 1.8 mm, less than 1.7 mm, less than 1.6 mm, less than 1.5 mm, less than 1.4 mm, less than 1.3 mm, less than 1.2 mm, less than 1.1 mm, or less than 1 mm.

In some embodiments, the housing body comprises a top component and a bottom component. In some embodiments, the top component and the bottom component of the housing body removably connect to each other to form a waterproof seal. Accordingly, attaching the top component and the bottom component prevents excess liquid from leaking out of the device. In some embodiments, the top component is a "cap" (e.g. a lid) and the bottom component is a sample collection cup. In some embodiments, excess absorbent material is used to eliminate the need for a waterproof seal to prevent the presence of excess fluid that could leak from an unsealed housing body.

Figure 7A:
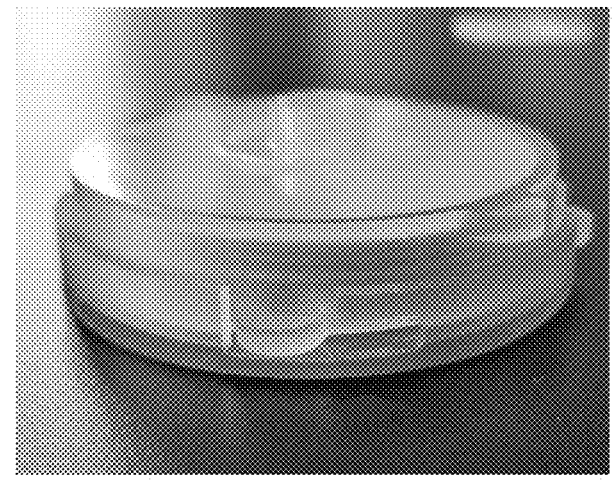
FIGS. 7A-7B show images of an exemplary device described herein. The device comprises a top component and a bottom component. The top component (e.g. the lid) comprises an opening which permits entry of the liquid sample into the device. In this instance, the opening is of suitable size and shape to allow placement of a funnel, which can further assist with applying the liquid sample to the device. The top component and the bottom component removably connect to each other to form a watertight seal. In some embodiments, the components connect to each other by at least one latch on the top component and at least one receiving hook on the bottom component. The latch slides into the receiving hook, thereby sealing the components together.
Figure 7B:
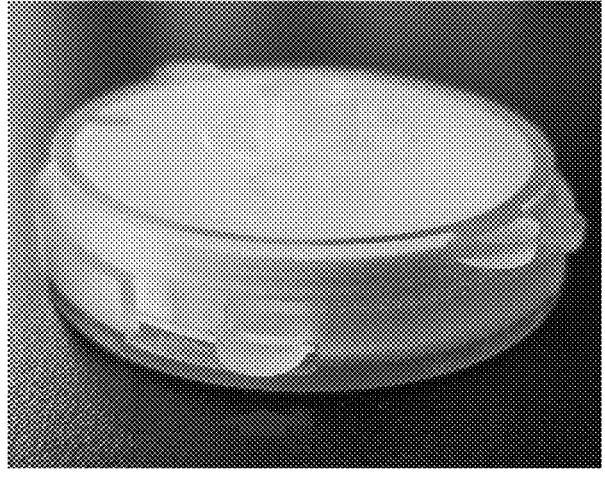
Figure 8:
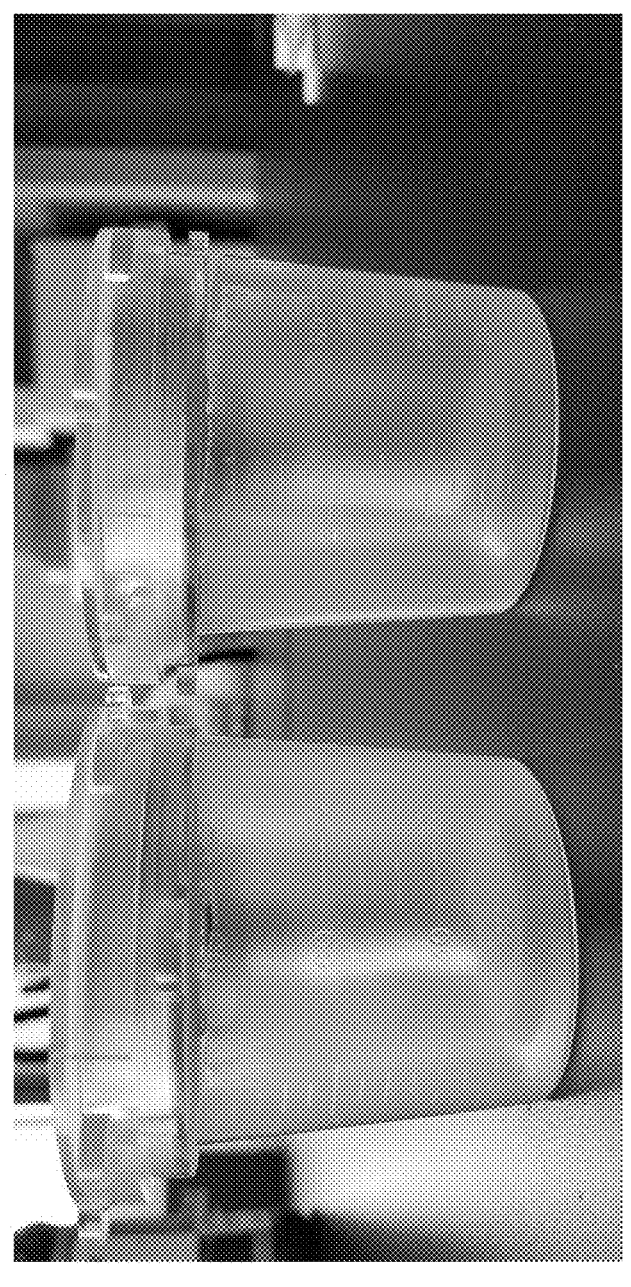
FIG. 8 shows another exemplary embodiment of a device described herein. This device, in contrast to the device shown in FIG. 1, relies on wicking of fluid sample against the force of gravity to bring the sample into contact with the porous membrane containing the capture and detection moieties. In this embodiment, the bottom component comprises a sample collection cup and the top component (e.g. the lid) comprises the wick/filter system, the porous membrane, and the absorbent pad. In this embodiment, the filter extends to the bottom of the sample collection cup, thus facilitating sufficient wicking of the sample.
Figure 9:
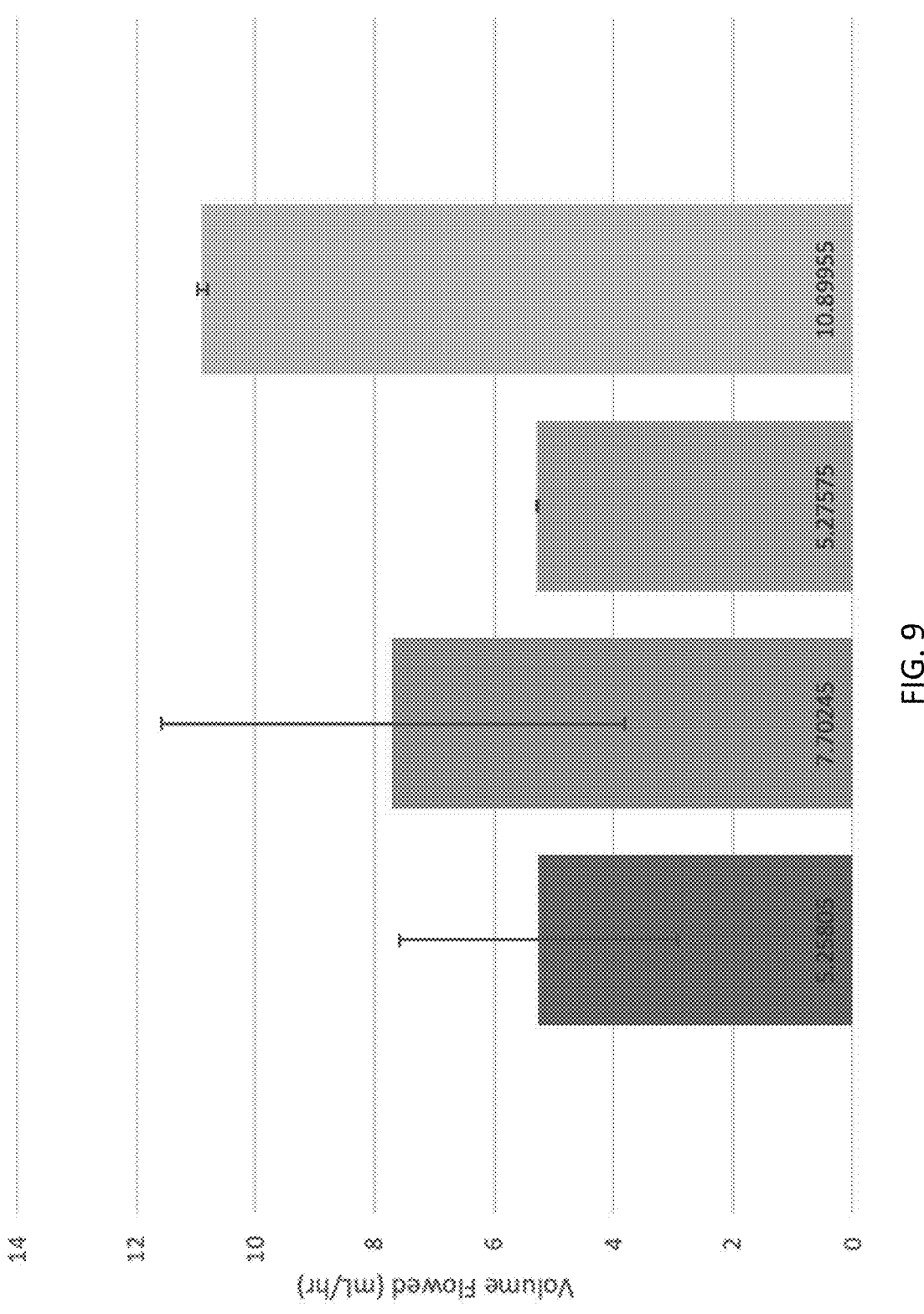
FIG. 9 shows a comparison of the flow rates of various devices. The data shows flow rate for the device that pulls fluid against the force of gravity and into contact with the porous membrane (referred to herein as the "wicking device" or the "wick design"), and flow rate of the device designed such that liquid flows in a gravity-assisted manner through the device (referred to herein as the "gravity-assisted device". The wicking device is shown in blue (trial 1 average) and orange (trial 2 average), and the gravity-assisted device is shown in gray (trial 1 average) and yellow (trial 2 average).
Figure 10:
FIG. 10 shows an image of an exemplary device described herein. In this embodiment, the device may be used in the gravity-assisted format (e.g. in conjunction with a funnel) or in a wicking format. In this image, the filter system is a cartridge containing multiple filter layers that is housed within the housing body, rather than held within the funnel.
Figure 11:
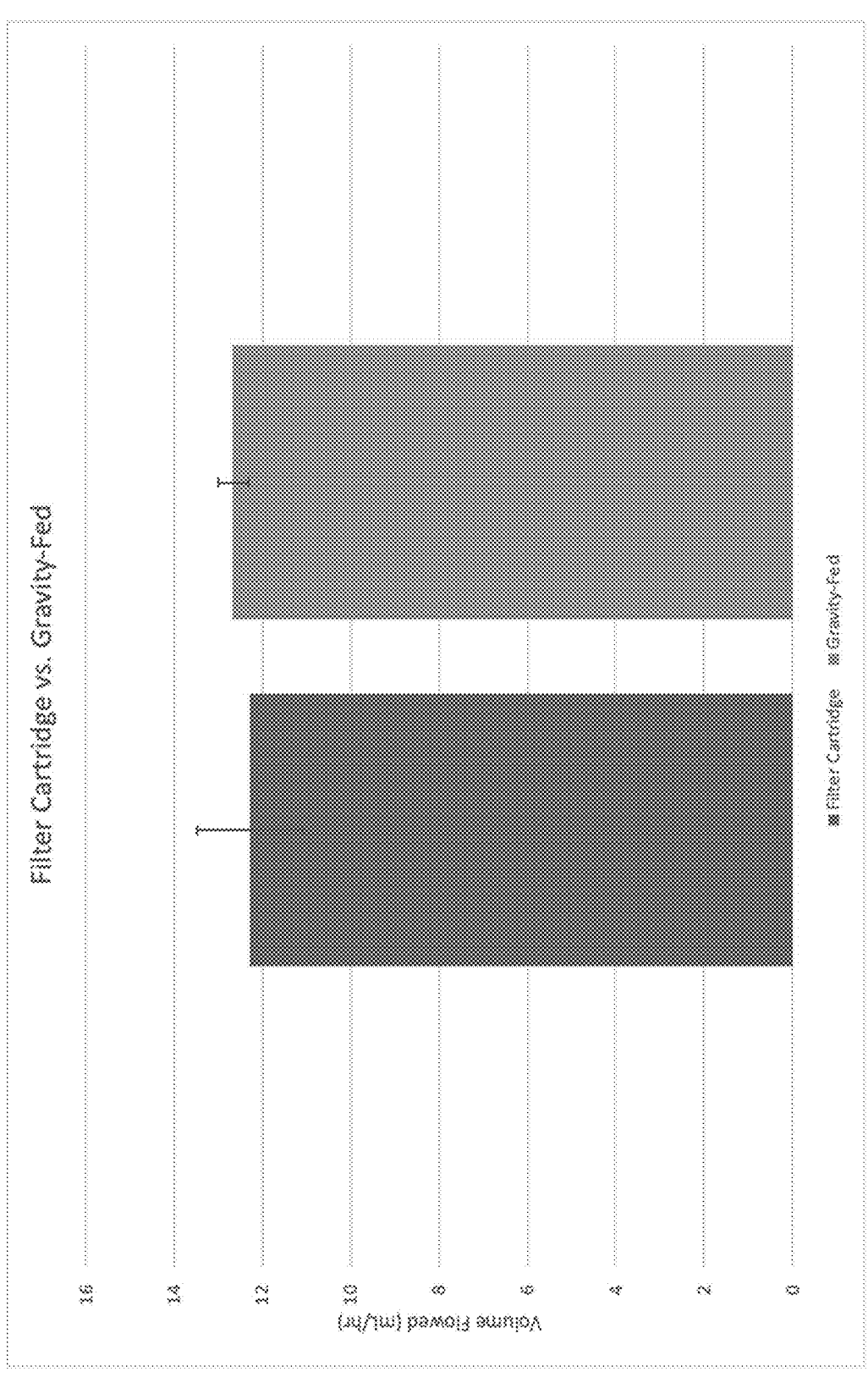
FIG. 11 shows a comparison of the flow rate for the device shown in FIG. 10 (e.g. containing the filter cartridge held within the housing body) and a gravity-assisted device used in conjunction with a funnel containing the filter (e.g., as shown in FIG. 1). The device containing the filter cartridge was run in the wick-design format, and is shown in blue. The gravity-assisted device is shown in orange.
Figures 12A, 12B:
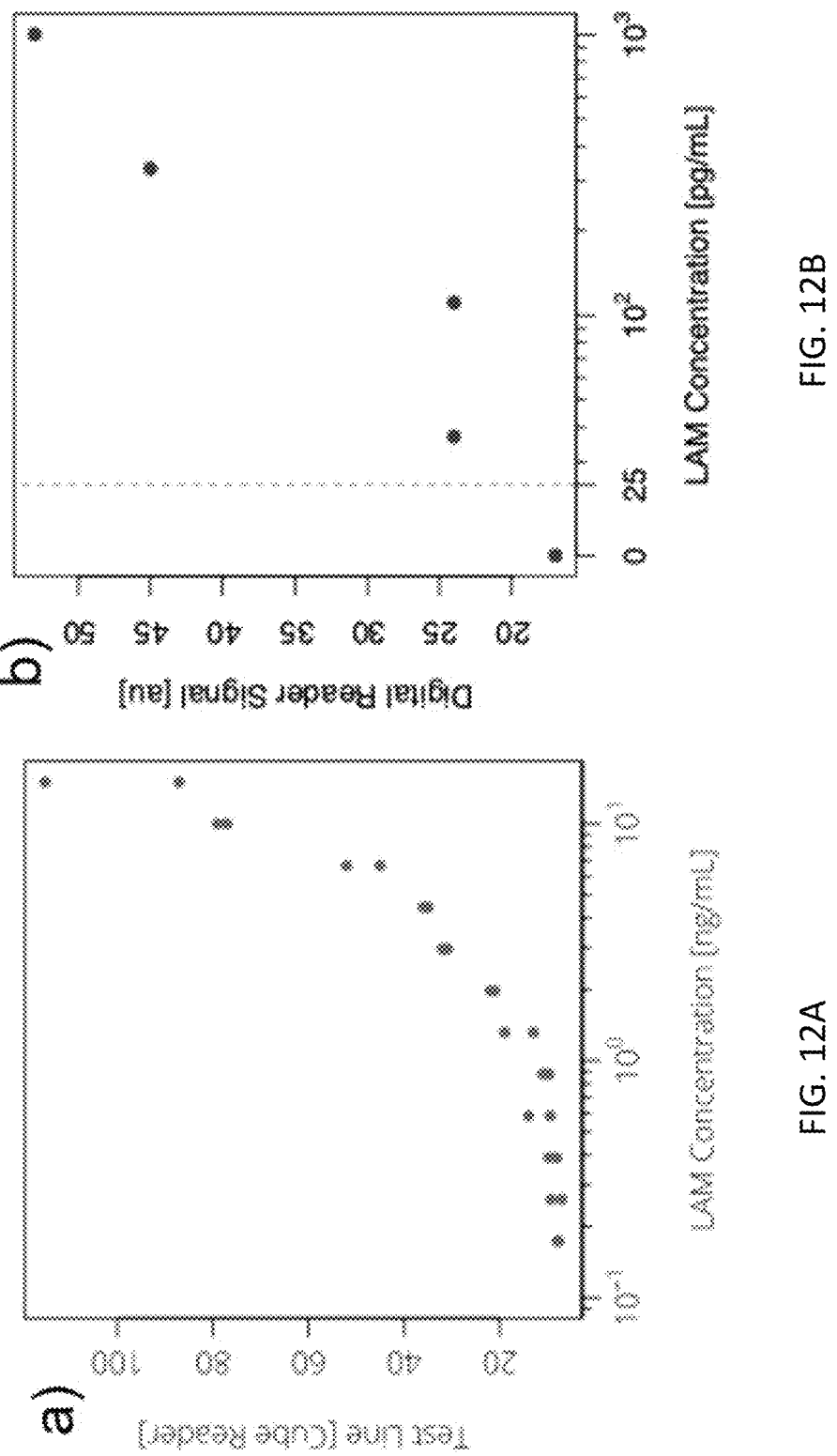
FIGS. 12A-12B shows a comparison of performance between a standard lateral flow assay without concentration (FIG. 12A) and a gravity-assisted device described herein (FIG. 12B). The limit of detection for the standard LFA alone is about 2 ng/mL while the gravity-assisted device is about 37 pg/mL, which is a roughly 54-fold increase in sensitivity.

The top component and the bottom component may be removably connected to each other by any suitable mechanism. For example, the top component (e.g. the cap) and the bottom component (e.g. the sample collection cup) may be snapped together. For example, the top component and the bottom component may connect to each other in one point by a hinge, and may snap together at an opposing point by a suitable locking mechanism, thereby generating a water-tight seal. As another example, the top component and the bottom component may be latched together in a twisting fashion. For example, the components may connect to each other by at least one latch on the top component and at least one receiving hook on the bottom component. The latch slides into the receiving hook, thereby sealing the components together. FIG. 7A shows this embodiment, where the device is unsealed. FIG. 7B shows this embodiment, where the device is sealed by sliding the latch into the receiving hook (e.g. by twisting the latch into the receiving hook). In these images, the top component (e.g. the lid) further comprises additional grips that allow the user to apply adequate torque to slide the latch into the receiving hooks.

Various components may be housed within the cap. For example, the filter system and the porous membrane may be housed within the cap. In some embodiments, the wicking component is housed within the cap. In some embodiments, the absorbent pad is housed within the cap. In some embodiments, the filter system, the porous membrane, the wicking component, and the absorbent pad is housed within the cap. In some embodiments, the component to guide the flow of liquid to the desired areas of the membrane (e.g. the capture region(s), the control region) is present in the cap. For example, the liquid impermeable layer containing one or more openings that correspond to desired locations within the porous membrane may be housed within the cap.

In some embodiments, one or more components are housed within the sample collection cup. For example, the one or more wicking components may be housed within the cup. For example, the filter system may be housed within the cup. In some embodiments, the wicking components and filter system may be housed within the cup as a single unit or as separate units or as a single separable unit. In some embodiments, the wicking components and/or filter system is removable. For example, the filter system may be designed such that it can be detached from the device after use. For example, the filter system may be detached from the cap after use. In some embodiments, the filter system is initially housed on the cap, and after use is transferred to the cup.

In some embodiments, provided herein is a device for detecting one or more analytes in a liquid sample. The device comprises a sample collection cup, a cap, and a filter system comprising one or more filter components. The cap comprises a porous membrane as described herein. For example, the cap may comprise a porous membrane containing one or more capture moieties held within a defined capture region of the porous membrane, and one or more detection moieties. In some embodiments, the cap further comprises at least one absorbent pad.

The cap and the cup removably connect to each other to form a waterproof seal. In some embodiments, liquid sample (e.g. the urine sample) is present within the sample collection cup. Once the sample is present, the cap is attached to the cup by a suitable mechanism. In some embodiments, following attachment of the cap to the cup, the device is turned over such that the liquid sample flows in a gravity-assisted manner from the cup into the cap. As with the other embodiments described herein, the liquid sample passes through the filter system prior to contacting the porous membrane.

In some embodiments, the cap and cup connect to one another but allow sample to be added after connection. For example, an open region of the cap can allow addition of sample through or around the cap. In some embodiments, the cup has an exposed edge, much like a pour spout, that facilitates addition of sample into the cup while the cap is connected.

Various potential locations for the filter system may be employed. In some embodiments, the filter system is housed within the cap. For example, the filter system may be housed within the cap, such that the liquid sample passes through the filter system, then passes through a component to guide flow of the liquid into the desired regions on the porous membrane, then enters the desired regions of the porous membrane. In some embodiments, the filter system may be removed from the cap following use. Removal of the filter system may facilitate facile visualization of results (e.g. detection of the signal generated by the detection moieties). Moreover, removal of the filter system may be advantageous in that it removes a biological hazard (e.g. urine) away from the device in an easy manner. In some embodiments, the filter system is removed from the cap and disposed of. For example, the filter system may be peeled off, twisted off, etc. In some embodiments, the filter system is removed from the cap, but remains attached to a different component of the device. For example, the filter system may be initially present on the cap, but following transfer of liquid through the device and separation of the cap and the cup, the filter may remain with the cup.

In some embodiments, the filter system is an intermediate component housed between the sample collection cup and the cap. In some embodiments, the intermediate component is initially attached to the cap. Following transfer of liquid through the device, the components may be separated such that the intermediate component containing the used filter remains associated with the sample collection cup rather than the cap. Such embodiments may be useful to facilitate easy visualization of the porous membrane contained within the cap, without being impeded by the presence of the intermediate component.

In some embodiments, the filter system is housed within the sample collection cup. For example, the filter component may be fixed to the cup such that application of the cap to the cup seals the filter cartridge against the cap. Upon inverting the cup, fluid is then forced to travel through the filter to pass through the membrane. Being fixed to the cup initially, the filter remains with the cup after cap removal to avoid interfering with application of wash fluid or imaging/reading of the membrane.

In some embodiments, the device comprises additional reagents to facilitate sample processing and/or analyte detection. These additional reagents may be lyophilized reagents. These additional reagents may be in liquid form. In some embodiments, the device comprises one or more reservoirs, containing additional reagents to facilitate sample processing and/or analyte detection. For example, the reservoirs may contain wash buffer. In some embodiments, the reservoirs may be disrupted to release the reagent (e.g. wash buffer) contained therein at a suitable point in time during sample processing. For example, the cap may comprise a reservoir containing wash buffer. Removal of the filter system from the cap and/or detachment of the cap from the cup and/or detachment of the cap from the intermediate component may disrupt the reservoir, thus releasing the wash buffer. Release of the wash buffer should be designed such that the wash buffer contacts the porous membrane, thereby removing excess unbound analyte and/or potential contaminants from the membrane prior to detection.

In some embodiments, the sample collection cup comprises additional reagents (e.g. liquid, dried, or lyophilized reagents) to facilitate handling and/or processing of the sample. The sample (e.g. urine sample) may be initially collected from the subject in a suitable receptacle. The liquid (e.g. urine) may then need to be transferred into the device, such as into the sample collection cup. In some embodiments, the sample collection cup contains liquid reagents, such as a neutralizing buffer, that are held within the cup by a suitable mechanism. In some embodiments, for example, the liquid reagents (e.g. neutralizing buffer) are retained within the cup by a physical barrier. This barrier (e.g. seal) may be removed prior to addition of the sample to the sample collection cup. In some embodiments, a porous material laden with dried reagents can be housed within the cup to store reagents and facilitate reconstitution upon addition of sample. In some embodiments, some reagents may be separated from the location of sample addition by a barrier with a hole that allows for time-delayed mixing of the added sample with the reagents. For example, if a sample is pre-treated (e.g., with trichloroacetic acid to precipitate protein) prior to addition to the device and requires a brief incubation period (e.g., <1 min) prior to neutralization, such a time-delayed mixing would allow the user to immediately add the pre-treated sample into the device instead of waiting prior to addition. Likewise, different dried reagents could be used within each compartment to create a sequencing of sample pre-treatment steps prior to preconcentration. The hole in such a barrier may also house a dissolving membrane for longer delays or a filter to prevent passage of certain sample components from one compartment to the next.

Any of the moieties contained within the devices described herein (e.g. assay reagents, capture moieties, detection moieties, blocking proteins, moieties within the filter system that prevent passage of unwanted contaminants through the filter components, etc.) may be dried onto the desired location within the device. In some embodiments, moieties that are dried onto the desired location within the device are rehydrated upon flow of the liquid sample through the device. In some embodiments, methods may be employed to prolong release of such reagents upon rehydration, thereby preventing rapid rehydration and flow of the desired reagent through the device too quickly. In some embodiments, reagent release is prolonged by optimizing the formulation of liquids that rehydrate the described moieties (e.g. buffers, such as wash buffers or neutralization buffers, or the liquid sample itself) to include substances that rehydrate more slowly such as sugars or dissolvable barriers. In addition, flow paths through the device can be structured to encourage prolonged release of desired reagents. Exemplary flow paths are described herein. FIG. 24 shows general mechanisms for structuring the flow paths through the materials to enable prolonged release of reagents in the device components. As materials rehydrate, volumes of fluid wet the different materials, redistributing the reagents prior to reaching a quasi-steady-state of flow through each junction and material. In some embodiments, an initial wetting process can be applied to carry volumes with rapidly rehydrated reagent(s) into different regions, which would then, subsequent to initial wetting, experience the flow paths illustrated in FIG. 24.

In some embodiments, alternate configurations to enhance filtration and manufacturing/assembly are used. Immunoassays can clog when processing large volumes of complex sample(s) (e.g., >~500 μL of urine). For some of the devices and methods described herein, the filters within the devices at least partially enable the use of larger volumes of biological sample, without clogging the porous membrane. In some embodiments of the systems and methods described herein, pre-filtration of large volumes of complex samples is accomplished by integrating concepts from both lateral flow methods to create a hybrid design that can (i) transition between lateral flow and vertical flow within the same device for unique capabilities while (ii) leveraging roll-based manufacturing to achieve extremely cheap device costs.

Lateral flow assays are typically constructed by overlapping the ends of a sequence of porous materials to allow fluid to pass from one material to the next for detection of a sample analyte. Each material can be laden with reagents (e.g., dried buffers, conjugate, etc.) such that the sample interacts with each reagent in a generally sequential fashion. However, excessive overlap at the junctions between materials can cause inefficient flow or inefficient sample transfer from one material to the next, especially when the resistance of the different materials is significantly different. An example of inefficiency can be seen in FIGS. 24C and 24D where, after initial wetting of the materials, flow lines concentrate near one end of the junction creating a region with poor perfusion and transfer of sample/reagent.

In some embodiments, provided herein is a hybrid device that comprises one or more porous materials. The porous materials include materials described herein, including a filter system (e.g. a system comprising one or more filter layers), a porous membrane (e.g. a porous membrane containing one or more capture moieties), absorbent pads, wicking components, etc. In some embodiments, flow of a liquid sample through one or more porous materials is substantially lateral. For example, the device comprises a first porous material ('A') wherein the flow of a liquid sample through the first porous material is substantially lateral, and a second porous material ('C'). In some embodiments, the flow of the liquid sample at the junction (e.g. interface) between two or more of the porous materials is substantially vertical. In some embodiments, the junction between the first and second porous materials comprises a filter system ('B') comprising one or more filter layers. In some embodiments, flow of the liquid sample through the one or more filter layers is substantially vertical. In some embodiments, the filter system inserted between the first and second porous materials forces flow of the liquid sample through both the filter system and the second porous material to be substantially vertical.

In some embodiments, flow of a liquid sample through each of the one or more porous materials is substantially lateral. For example, the device comprises a first porous material ('A') wherein the flow of a liquid sample through the first porous material is substantially lateral, and a second porous material ('C') wherein flow of the liquid sample through the second porous material is substantially lateral. In some embodiments, the flow of the liquid sample at the junction (e.g. interface) between two or more of the porous materials is substantially vertical. In some embodiments, a filter system ('B') comprising one or more filter layers is introduced at the junction between the first porous material and the second porous material, and flow of the liquid sample through the one or more filter layers is substantially vertical.

In some embodiments, the device comprises a filter system comprising one or more filter components, a porous membrane containing one or more capture moieties held within a defined capture region of the porous membrane, and at least one absorbent pad. In some embodiments, the device is configured such that a liquid sample flows substantially vertically through the filter system prior to contacting the porous membrane, and subsequently flows through the porous membrane and into the at least one absorbent pad. In some embodiments, the device additionally comprises one or more wicking components. In some embodiments, the device additionally comprises a first wicking component and a second wicking component that are separated by the filter system. Such an embodiment is demonstrated in FIG. 25. In some embodiments, the device comprises a first wicking component that absorbs the liquid sample and pulls (e.g. wicks) the liquid sample onto the filter system. In some embodiments, a portion of the wicking component pulls the liquid sample substantially against the force of gravity out of a reservoir containing the liquid sample (as shown in FIGS. 25A, 25B, and 25C). In some embodiments, the flow of the liquid sample through at least a portion of the first wicking component is substantially lateral. For example, in some embodiments a portion of the first wicking component pulls the liquid sample out of a reservoir containing the liquid sample, and a second portion of the first wicking component wicks the sample in a substantially lateral flow path along the first wicking component. In some embodiments, the device additionally comprises a second wicking component, wherein flow of the liquid sample through the second wicking component is also substantially lateral. In some embodiments, a portion of the first wicking component and a portion of the second wicking component are stacked. At such a junction, a filter system may be placed between the first and second wicking components. In some embodiments, the flow of the liquid sample through the filter system at the junction of the first and second wicking components is substantially vertical.

In some embodiments, vertical flow assay and lateral flow assay steps or components are integrated to generate a hybrid device that can wholly or largely be constructed using roll-based manufacturing techniques, such as those used for making traditional lateral flow assays. In some embodiments, a hybrid lateral/vertical flow device is created by introducing a filter system 'B' at the junction between two other lateral flow materials ('A' and 'C'). In some embodiments, the two other lateral flow materials are a first wicking component ('A') and a second wicking component ('C'). In some embodiments, inserting the filter system into the interface between materials A and C forces fluid to flow substantially vertically through material 'C', enabling integration of vertical flow filtration components within a lateral flow assay. This approach is substantially different than incorporating a filter using a standard lateral flow design where materials A, B, and C would be joined in sequence by overlapping their ends sufficiently to allow transfer of fluid from one to the next. In the vertical flow embodiment, the filter acts as a membrane filter whereas in the lateral flow embodiment (e.g. A, B, and C in a lateral flow sequence), the filter acts as a depth filter. Membrane-based and depth-based filtering approaches have different material requirements, required geometry, and performance characteristics (e.g., propensity to clog and particle size cut-off characteristics).

In some embodiments, the amount of overlap between materials at junctions can be modulated. For example, by increasing the amount of overlap at a junction, the cross-sectional area perpendicular to flow can be dramatically increased as it passes substantially vertically through material B compared to the flow cross-sectional area as it passes laterally through only material A or C. Changing the cross-sectional area of flow allows different methodologies and operations to be performed compared to just lateral flow or vertical flow methodologies. For example, a filter membrane with a well-defined pore-size can be used as material B to leverage the large surface area perpendicular to flow that is required to enable processing of large volumes of complex samples. The hybrid design allows the filter to be integrated directly upstream of a standard lateral flow assay component (e.g., conjugate pad, nitrocellulose membrane functionalized with test and control antibodies, and absorbent pad), creating a modular design with more flexibility. If the filter were integrated as a lateral flow component, the limited cross-section would result in clogging. The hybrid design can be used to address clogging and maintain a tightly controlled filter pore-size while allowing the detection membrane to be unobstructed.

The above-described concept of integrating material 'B' at a lateral flow junction can be applied to many assay designs. More generally, junctions between standard lateral flow assay components (e.g., laterally configured sample pads, conjugate pads, wicks, and membranes) can be augmented with additional layers, overlap, localized permeability, thicknesses, branching, etc. to enable junctions with substantially vertical flow for new functionality (e.g., integration of membrane filters, stacks of filters with varying pore sizes, flow resistors, and junctions to merge or distribute flow from different layers of a device).

FIG. 24, FIG. 25, and FIG. 26 describe a plethora of configurations that illustrate how the general concepts for creating hybrid lateral/vertical flow assays can be used to create immunoassay designs with novel functionality for the purpose of detecting an analyte from a range of sample volumes (e.g., 0.05, 0.1, 1, 2, 5, 10, 20, 50, 100, 200, 500 mL of sample). The intent of the figure is to illustrate examples relevant to the stated application while also showing multiple different functionalities and possible design strategies that could be used in any combination to create a wide range of possible assays designs that are not specifically illustrated.

Any suitable filter material can be used in a hybrid device, including in accordance with the configurations illustrated in FIG. 25, FIG. 25, and FIG. 26. Examples of suitable filter materials (e.g. filter system layer materials) include, but are not limited to, PTFE, MCE, and PES. The pore size of the filter material may need to be large enough to allow passage of conjugate particles added to the sample yet filter out components in urine that can clog the membrane material. The pore size of the filter material can be adjusted for each application. In some embodiments, the pore size is between 0.2 μm and 8 μm. Smaller pore size materials generally require large flow cross-sectional areas. Also, as the flow cross-sectional area increases, the maximum amount of sample that can pass through the material before clogging increases.

The vertical-flow-based filter component also allows for the slow release of dried conjugate from a pad positioned above the secondary wick. Drying the conjugate in a pad down-stream of the filter offers several advantages including improved shelf life, simpler manufacturing, prolonged release of reagents (e.g., conjugate) and avoiding the potential loss of conjugate to the filter membrane or nonspecific adsorption of unwanted sample components on the conjugate. The timed release can be controlled by pad configuration, patterning/position of flow barriers, pad pore size and porosity (i.e., the fluid flow resistance of the pads), as well as incorporation of dissolvable flow impediments (e.g., dried sugars and/or polymers with the conjugate). Typically, as flow resistance of the reagent pad increases, the flow through this reagent pad will decrease and the release of reagent into the flow will be slower, potentially to the point where transport is largely through vertical (as depicted) diffusion between the layers.

Figures 27A, 27B, 27C:
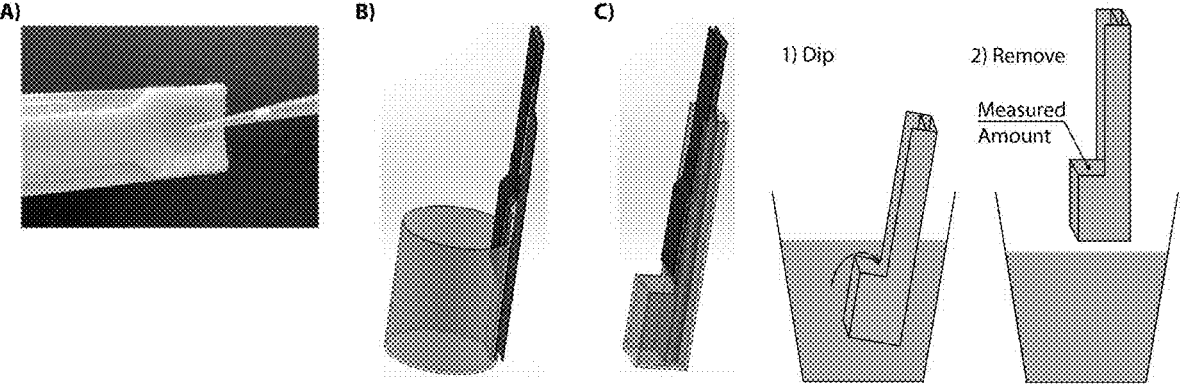
Figures 29A, 29B:
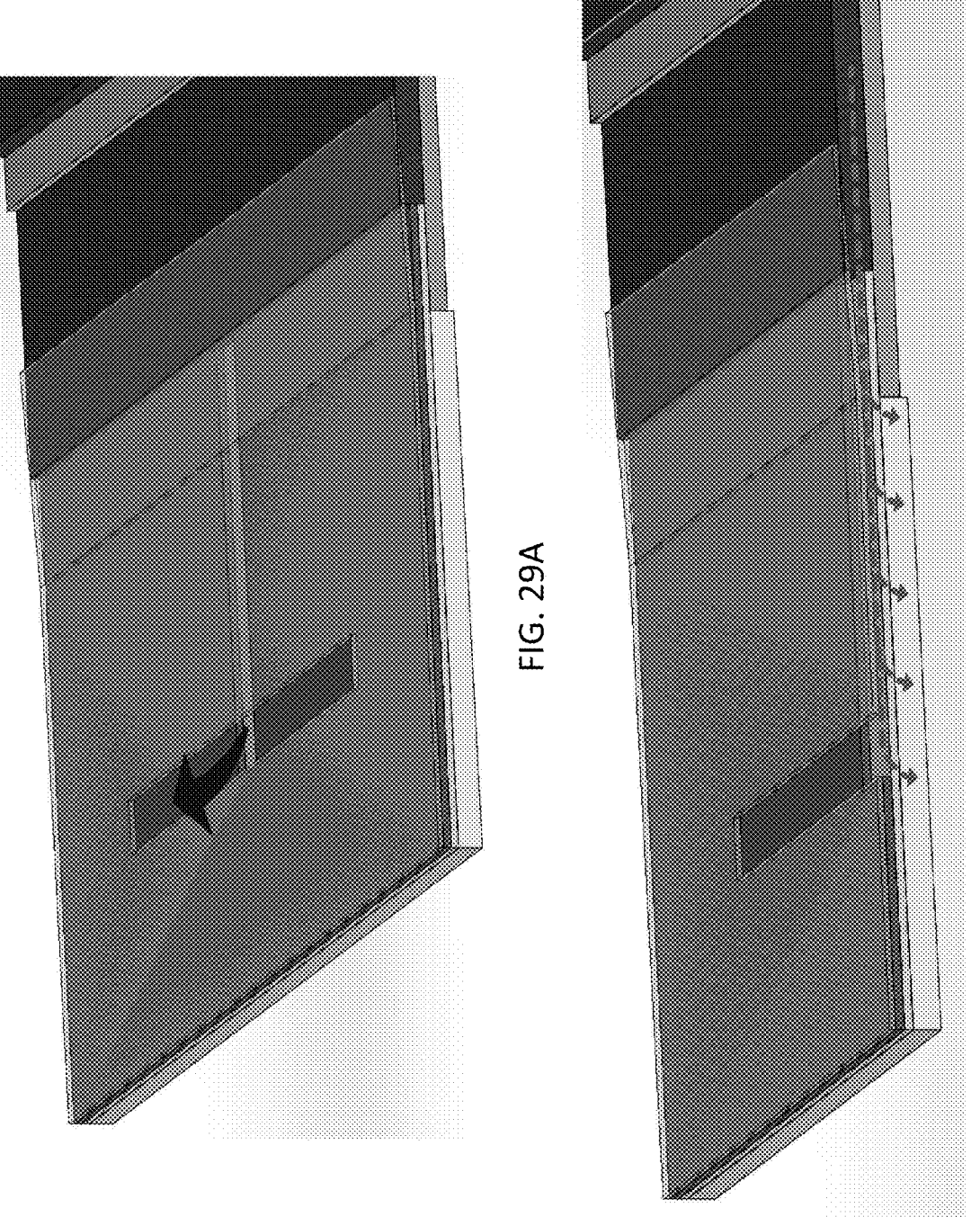
FIG. 29A shows an exemplary channel used to transport or direct fluid flow to porous material. In this embodiment, the four layers on the left, from top to bottom, are a (i) transparent hydrophilic plastic film, (ii) double sided adhesive, (iii) porous membrane potentially with capture or control regions/indicators, and (iv) wicking or absorbent material. In this configuration, the double sided adhesive is cut to form a channel over the top of the porous membrane, using the transparent film as the top of the channel. Optionally (as depicted here), an opening in the transparent film could be used to allow air to escape the channel as fluid enters from the right.
FIG. 29B shows a cross-section view of the device configuration depicted in (FIG. 29A). The dashed arrows illustrate how fluid is able to enter the channel and pass down through the porous membrane into the wicking or absorbent material substantially vertically. Upstream, the material on the bottom of the device to the right of the absorbent or wicking material does not absorb fluid. Therefore, fluid is only able to pass down through the porous membrane in a portion of the channel.

In some aspects, the devices described herein are manufactured, at least in part, using roll-based manufacturing methods. The term "roll-based" refers to manufacturing methods involving continuous manufacture of an article largely from rolls of source material, typically as it is conveyed along a roller-based processing line. Roll-based manufacturing methods result in cost-effective and efficient production of the devices described herein compared to methods wherein each of the various components of the device are built separately and then later assembled. Accordingly, the ability to manufacture more of the device components via roll-based manufacturing provides a significant manufacturing cost and reliability advantage over the use of separate components that are later assembled. Potential methods of manufacturing a largely or completely roll-based device are illustrated in FIG. 25 and FIG. 26. Further, potential methods for introducing sample into/onto these devices are illustrated in FIG. 27.

In some aspects, provided herein are methods of detecting one or more analytes in a liquid sample. The methods may be performed using any suitable device described herein. In some embodiments, provided herein is a method for detecting one or more analytes in a liquid sample, comprising applying the liquid sample to a device described herein. In some embodiments, the liquid sample contacts the porous membrane such that the analyte (if present) binds to the one or more capture moieties within the porous membrane. In some embodiments, the liquid sample passes through the filter system and onto the porous membrane, such that the analyte (if present) binds to the one or more capture moieties within the porous membrane. The method further comprises detecting the one or more analytes. For example, the analytes may bind to the capture moieties held within the defined capture region of the porous membrane, and the detectable moieties will also bind to the analyte. Binding of the analyte to the detectable moiety results in an accumulation of a detectable signal, which can be assessed to determine the presence and/or amount of analyte in the sample. In some embodiments, the detectable signal is assessed visually. Alternatively, this signal can be assessed using a digital reader. For example, the signal can be assessed using a digital microscope. As another example, the signal could be assessed using a digital reader device, including a mobile phone. If the signal is assessed using a detection device (e.g. a digital reader, a digital microscope, a mobile phone, etc.), the result may be transmitted. For example, the result may be transmitted (e.g. delivered) by a suitable communication means, including audio, visual, wired, or wireless communication means.

For some sample types, without the use of filters, the volume of biological sample that can be passed through the porous membrane for detection is limited by components that clog the porous membrane. For example, urine clogs when <1 mL passes through a nitrocellulose membrane. In contrast, the use of filters in the devices described herein enable use of larger volumes of biological sample, without clogging the porous membrane. Thus, in some embodiments, the methods comprise applying at least 1 mL of urine to the device described herein. For example, the methods comprise applying at least 1 mL, at least 2 mL, at least 3 mL, at least 4 mL, at least 5 mL, at least 6 mL, at least 7 mL, at least 8 mL, at least 9 mL, at least 10 mL, at least 11 mL, at least 12 mL, at least 13 mL, at least 14 mL, at least 15 mL, at least 16 mL, at least 17 mL, at least 18 mL, at least 19 mL, or at least 20 mL of urine to the device In some embodiments, the methods comprise providing more than 20 mL of urine to the device. For example, at least 20, at least 30 mL, at least 40 mL, at least 50 mL, at least 60 mL, at least 70 mL, at least 80 mL, at least 90 mL, or at least 100 mL of urine may be added to the device. The device is designed as described above such that this volume of sample (e.g. urine) can pass through the filter system and contact the porous membrane without clogging the filter to a sufficient degree to prevent passage of further sample through the filter. Other biological samples may contain more material that clogs the porous membrane more quickly (e.g. after a smaller volume of sample has been added), such as blood compared to urine. Thus, in some embodiments, the methods comprise applying at least as much volume as would typically be required to clog the membrane without any filters. Still other fluid samples may not pose a risk of clogging, yet require preconcentration to achieve sufficient sensitivity. Thus, in some embodiments, the methods comprise applying at least as much volume as would be required to accumulate sufficient analyte for detection given the particular application. Moreover, the device is designed as described above such that the liquid sample is absorbed by the absorbent pad(s), thereby preventing leakage from the housing body. However, if not all the sample is absorbed, a waterproof connection between the cap and cup can also prevent leakage from the housing.

In some embodiments, the methods facilitate detection of the analyte of interest with high sensitivity. For example, the assay for one particular analyte of interest may have a limit of detection of less than 1 ng/mL. For example, the limit of detection may be less than 1 ng/mL, less than 900 pg/mL, less than 800 pg/mL, less than 700 pg/mL, less than 600 pg/mL, less than 500 pg/mL, less than 400 pg/mL, less than 300 pg/mL, less than 200 pg/mL, less than 100 pg/mL, less than 90 pg/mL, less than 80 pg/mL, less than 70 pg/mL, less than 60 pg/mL, less than 50 pg/mL, less than 40 pg/mL, less than 30 pg/mL, less than 20 pg/mL, or about 10 pg/mL. For example, for another combination of antibody and antigen where sensitivity is improved, the limit of detection may be less than 50 pg/mL, 40 pg/mL, 30 pg/mL, 20 pg/mL, 10 pg/mL, 9 pg/mL, 8 pg/mL, 7 pg/mL, 6 pg/mL, 5 pg/mL, 4 pg/mL, 3 pg/mL, 2 pg/mL, or about 1 pg/mL.

The analyte of interest may be any suitable analyte. In some embodiments, the analyte of interest is indicative of infection in the subject. For example, the analyte may be indicative of bacterial infection, viral infection, fungal infection, or other parasitic infections in the subject.

In some embodiments, the analyte of interest is lipoarabinomannan (LAM), which is indicative of tuberculosis infection in the subject. In some embodiments, the analyte of interest is circulating anodic antigen (CAA), which is indicative of schistosomiasis infection in the subject.

In some aspects, provided herein are kits comprising a device described herein. In some embodiments, the kit comprises a device in a partially unassembled state. For example, the kit may comprise the various components of the device in a partially unassembled state such that various components must be connected prior to use. For example, the top component (e.g. the cap) and the bottom component (e.g. the cup) may be disassembled in the kit, such that the user can apply the sample (e.g. the urine) to the cup prior to assembling the cup and the cap together. In other embodiments, the device is in an assembled state within the kit. The kit may further comprise instructions for use of the device. Instructions may be available in written or printed form, as reference to an online platform containing the instructions (e.g. a website link), or as part of a software application (e.g., smart-phone application).

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

EXAMPLES

Example 1

Standard lateral flow technology is considered to be extremely cheap and simple. Therefore, it is seen as an ideal format for point-of-care and applications for low- and middle-income countries (LMIC). However, lateral flow technology also has modest to low sensitivity, which significantly limits its breadth of potential applications. For example, it is estimated that a lateral flow-based urine test for lipoarabinomannan (LAM), an analyte which appears to be present predominantly in people with active tuberculosis, would need to detect on the order of 10 pg/mL to meet necessary clinical sensitivity and specificity guidelines estimated by experts in the field and the world health organization for tuberculosis triage testing. Currently, commercially available lateral flow tests for detecting LAM are limited to sensitivities on the order of 1 ng/mL, ~100 fold higher than necessary.

Preconcentration of analytes prior to running on an LFA can directly increase sensitivities more than 100-fold, allowing LFAs to be applied to, and therefore more useful for diagnosis of, tuberculosis and many other new applications. However, for world health applications, preconcentration should be achieved as cheaply and simply as possible to meet the needs of LMICs where cost and simplicity are primary drivers of adoption, uptake, and impact.

Vertical flow assays were developed as a way to reduce assay times for analytes at relatively high concentrations. In other words, the time required for mixing, binding, and capture of analyte and conjugate onto the test line in lateral flow assays was excessive. Instead, in a vertical flow assay the sample and conjugate could be passed through the membrane vertically to achieve much faster assay times. However, these faster assay times are typically to the detriment of sensitivity. Thus, vertical flow assays are typically used only in high analyte concentration applications.

Accordingly, a design challenge is to make vertical flow assays more sensitive. Increasing sensitivity can be achieved by processing more sample; however, for "dirty" sample types, the membrane becomes blocked if too much sample is passed through the membrane. For example, a CN95 membrane with a ~0.5 μm pore size becomes clogged with ~1 mL of urine. Becoming clogged prevents subsequent applications of reagent, which is typically necessary to obtain test results.

Figure 13A:
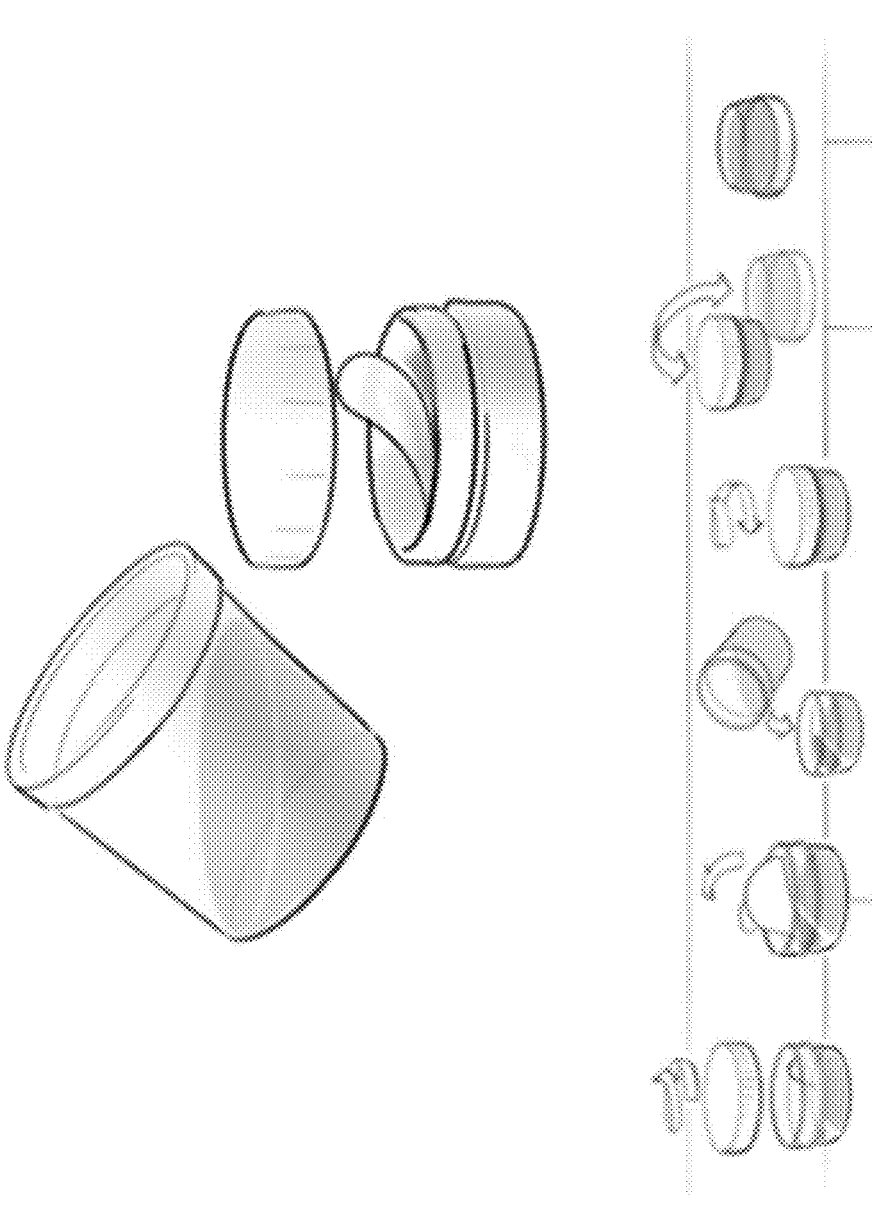
FIGS. 13A-13B shows an illustration of an exemplary device described herein. The device comprises a sample collection cup and a cap. In this embodiment, the cap comprises the filter system, the porous membrane containing the capture and detection moieties (NC membrane), and at least one absorbent pad (FIG. 13B). The cap additionally comprises a wicking element to assist in moving liquid away from the porous membrane and into the absorbent pad. The process for use of the device is shown in FIG. 13A. The sample (e.g. urine sample) may be initially collected from the subject in a suitable receptacle. The cap of the device is removed from the sample collection cup, and the sample is poured into the sample collection cup. In this embodiment, the sample collection cup houses a neutralizing buffer, which is retained within the cup by a removable seal. The seal is removed from the cup prior to addition of the liquid sample. Once the sample is added to the sample collection cup, the cap is screwed back on and the device is flipped over. The sample travels through the urine filter prior to contacting the porous (nitrocellulose) membrane containing the capture and detection moieties.
Figure 13B:
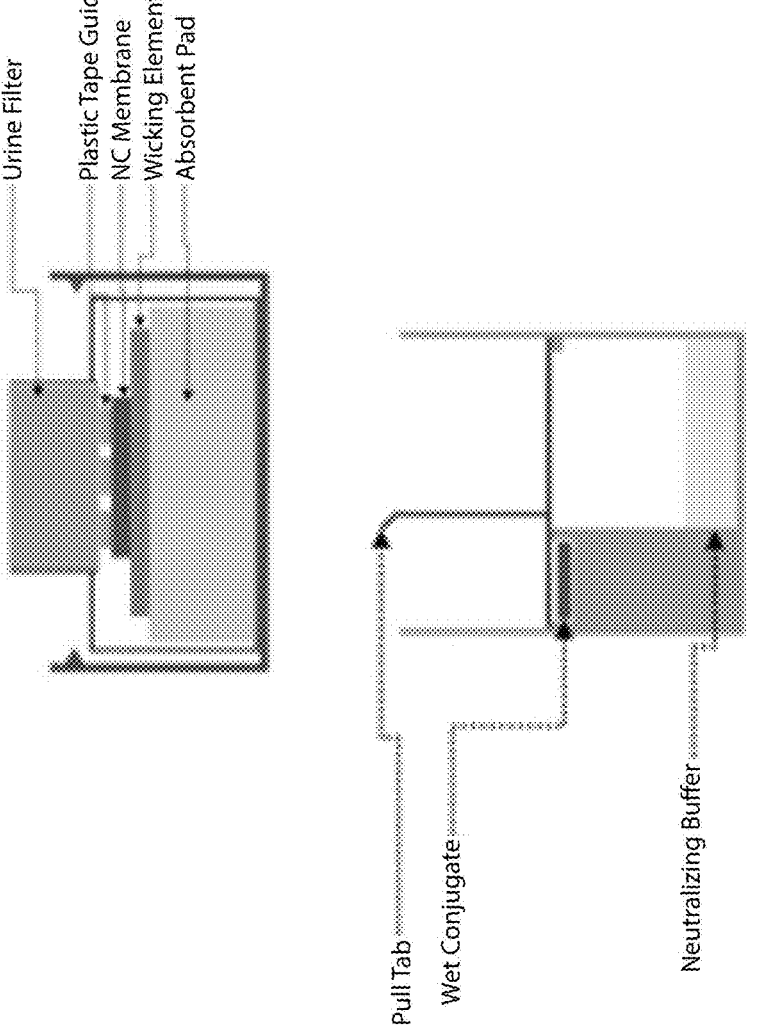
Figures 14A, 14B, 14C, 14D:
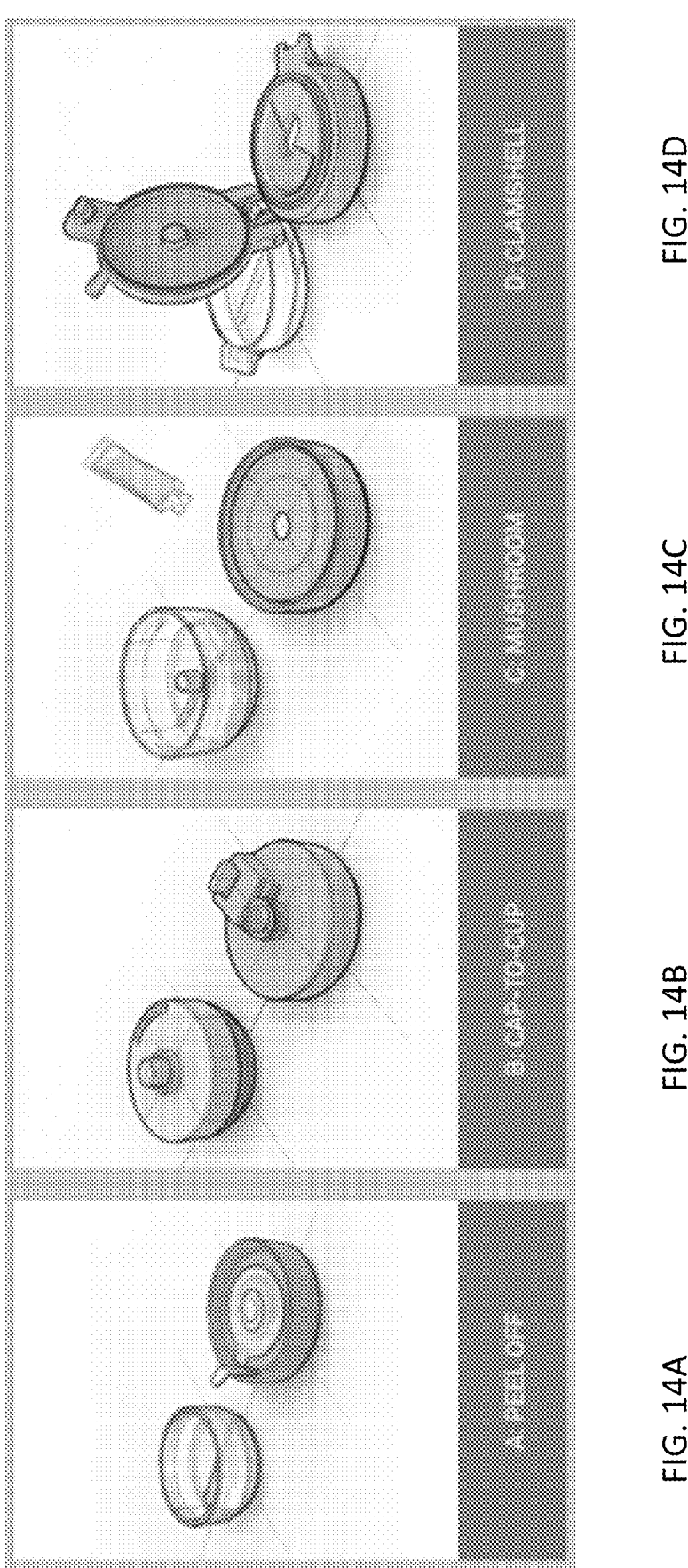
FIGS. 14A-14D show additional exemplary devices comprising a sample collection cup, a cap, and a filter system. For all images, the cap is shown as blue.
Figure 16B:
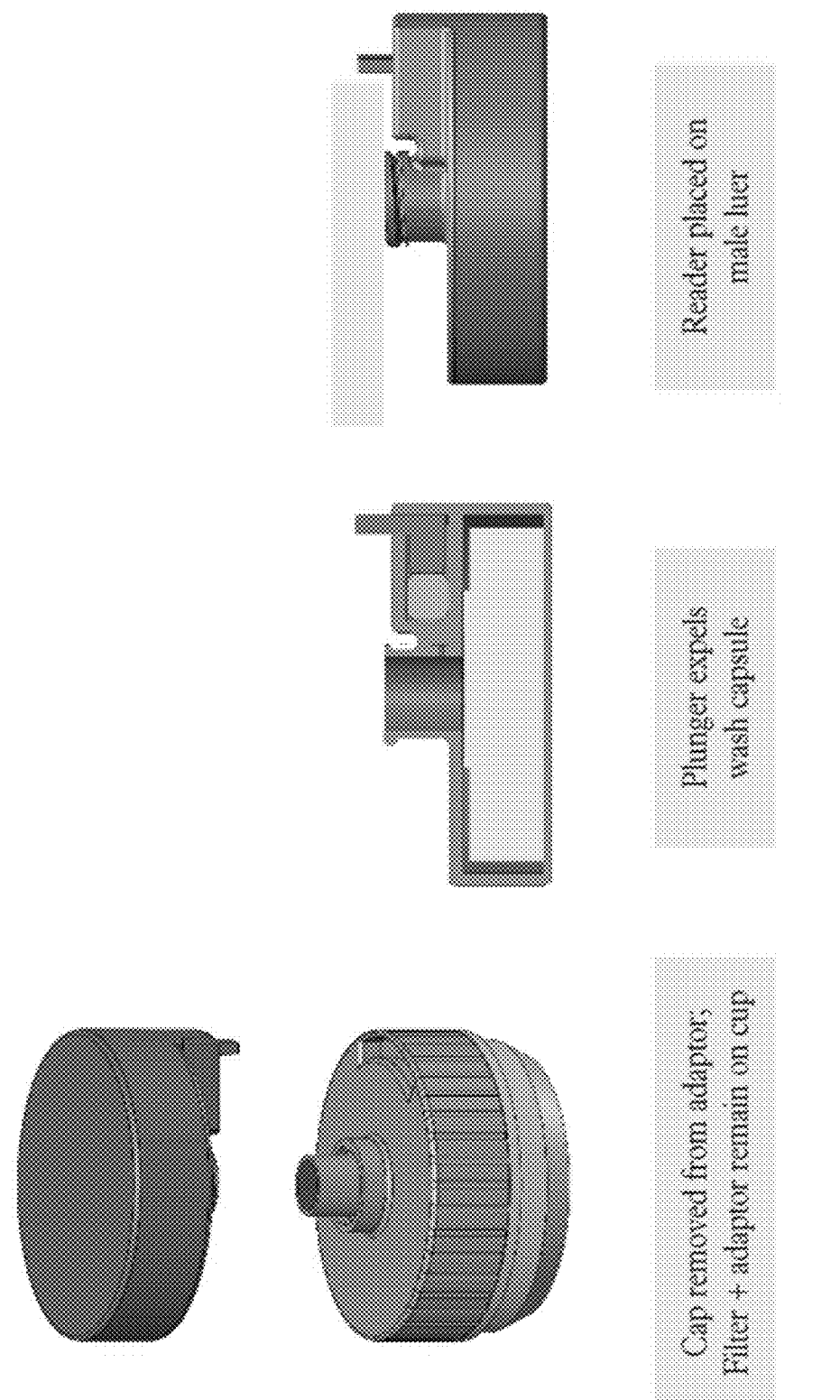
Figure 17B:
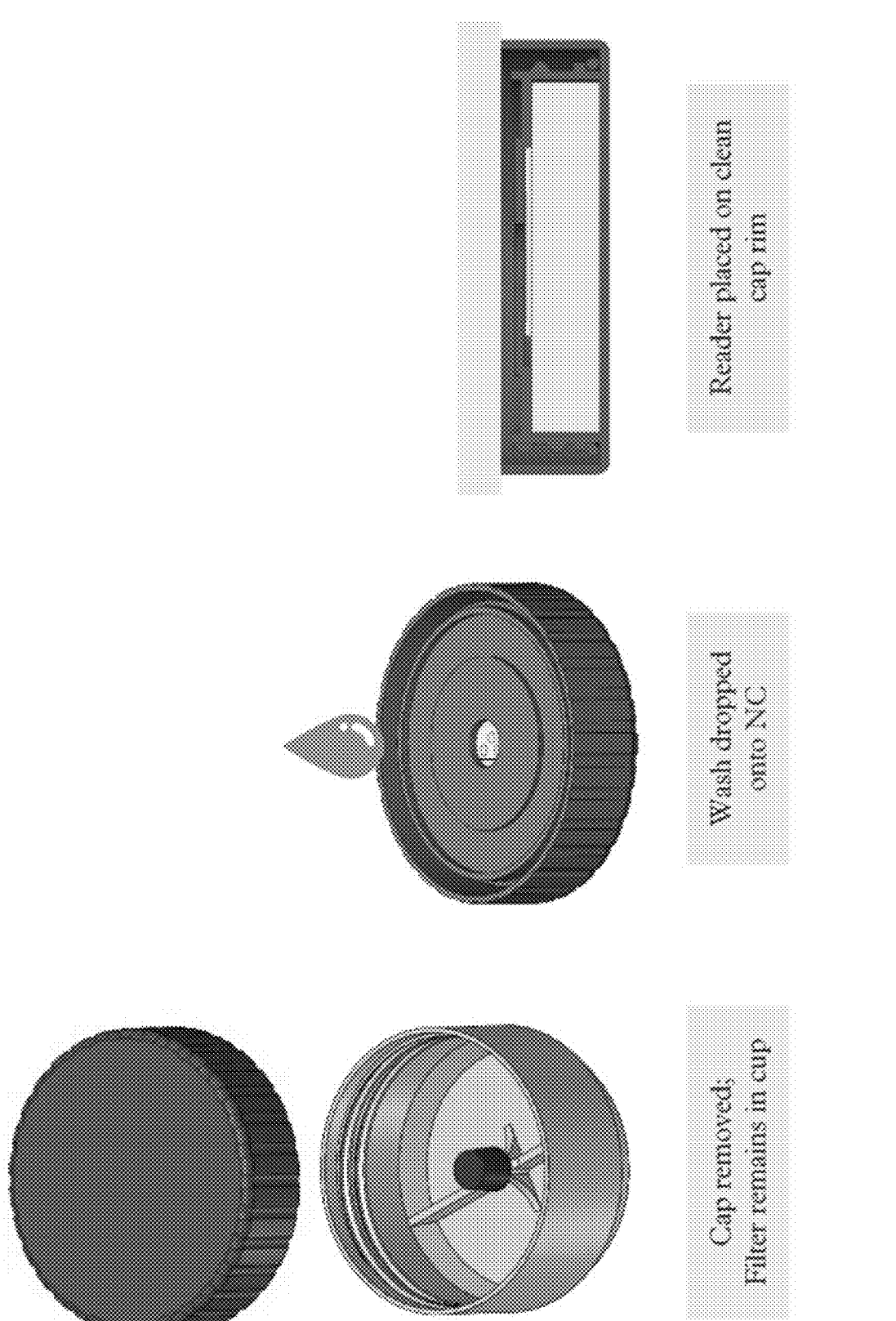
Figure 17E:
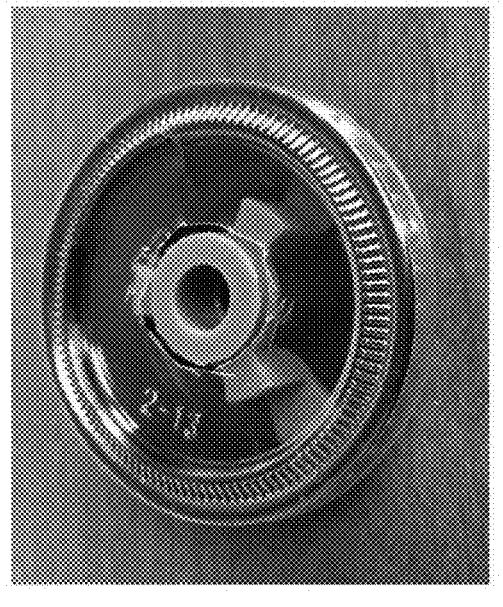
FIG. 17D, FIG. 17E, FIG. 17F, and FIG. 17G show exemplary embodiments of a cup as described herein. These images illustrate the ability to utilize a standard condiment cup as the sample cup and that the standard cup lid can be modified for an NC membrane to be adhered to the cup lid. With such an approach, filter pads would be placed on top of the lid and housed inside another component that would fasten on top of the cup lid. This general approach would allow the device to be inverted for gravity assisted flow or for use with a wick. Overall, the use of very thin thermoformed plastics such as these could reduce plastic use to be less than a standard LFA cassette and could meet design goals necessary for LIMC applications.
Figure 17G:
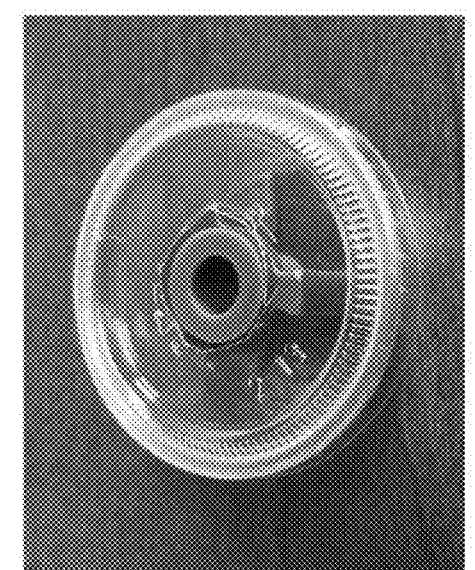
Figure 17D:
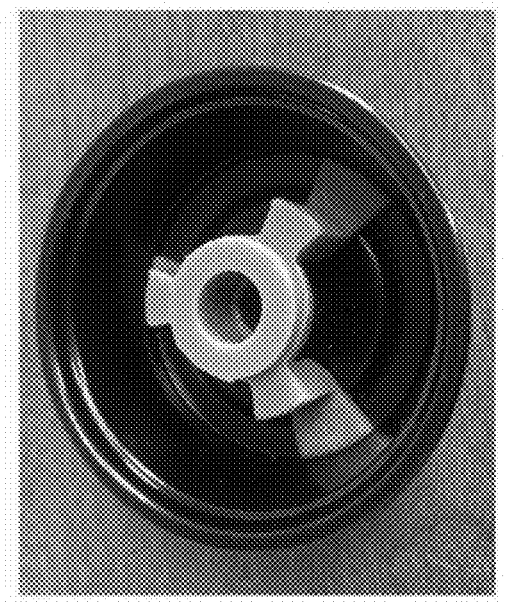
Figure 17F:
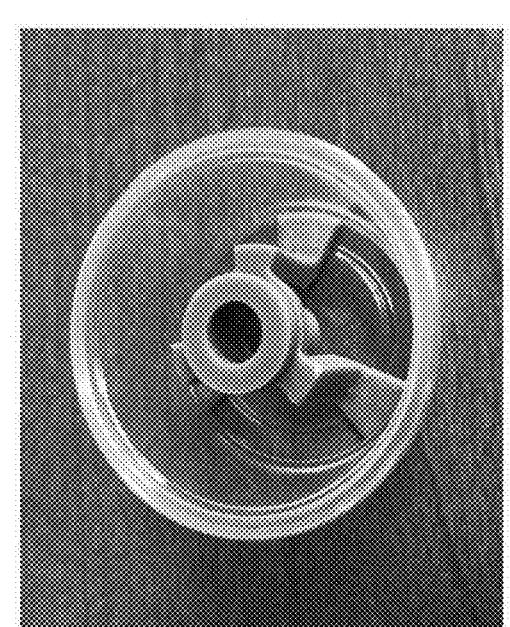
Figure 17I:
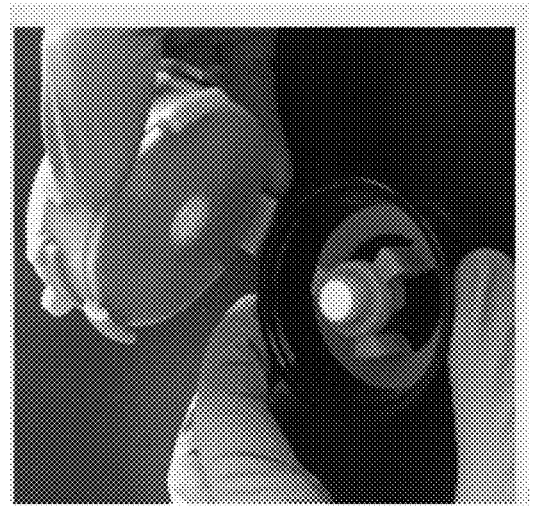
FIG. 17H-17J. show a 3D-printed lid that houses absorbent pads and the nitrocellulose strip has been created that clips onto the top of the condiment cup. Here, the filter/wick cartridge (as shown in FIG. 17B) simply presses into the bottom of the lid against the nitrocellulose strip.
Figure 17H:
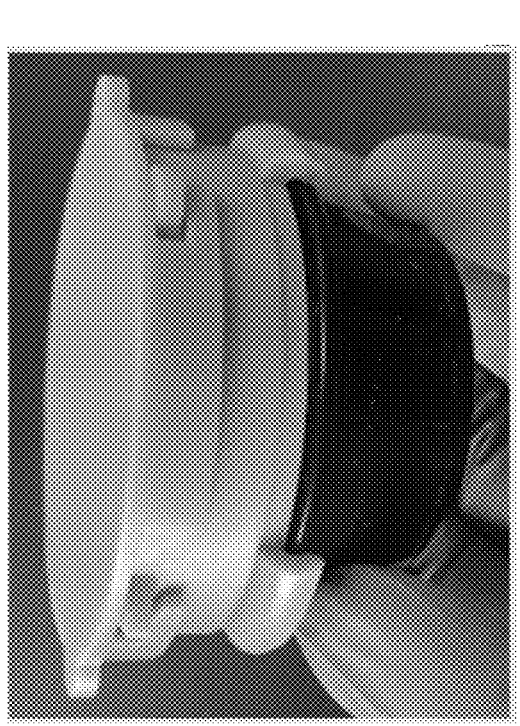
Figure 17J:
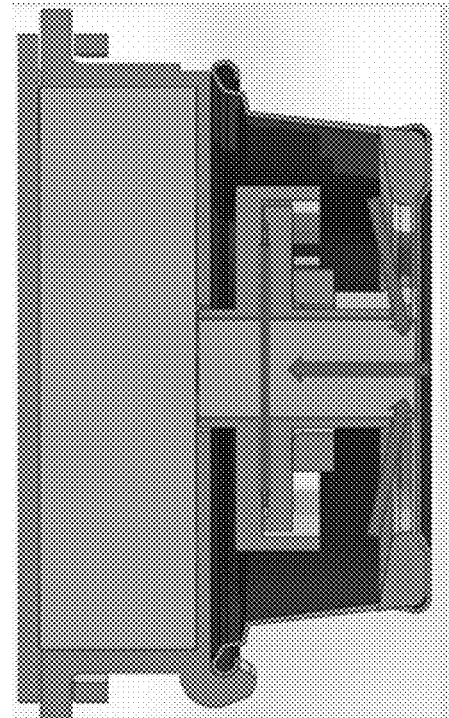
Figure 19A:
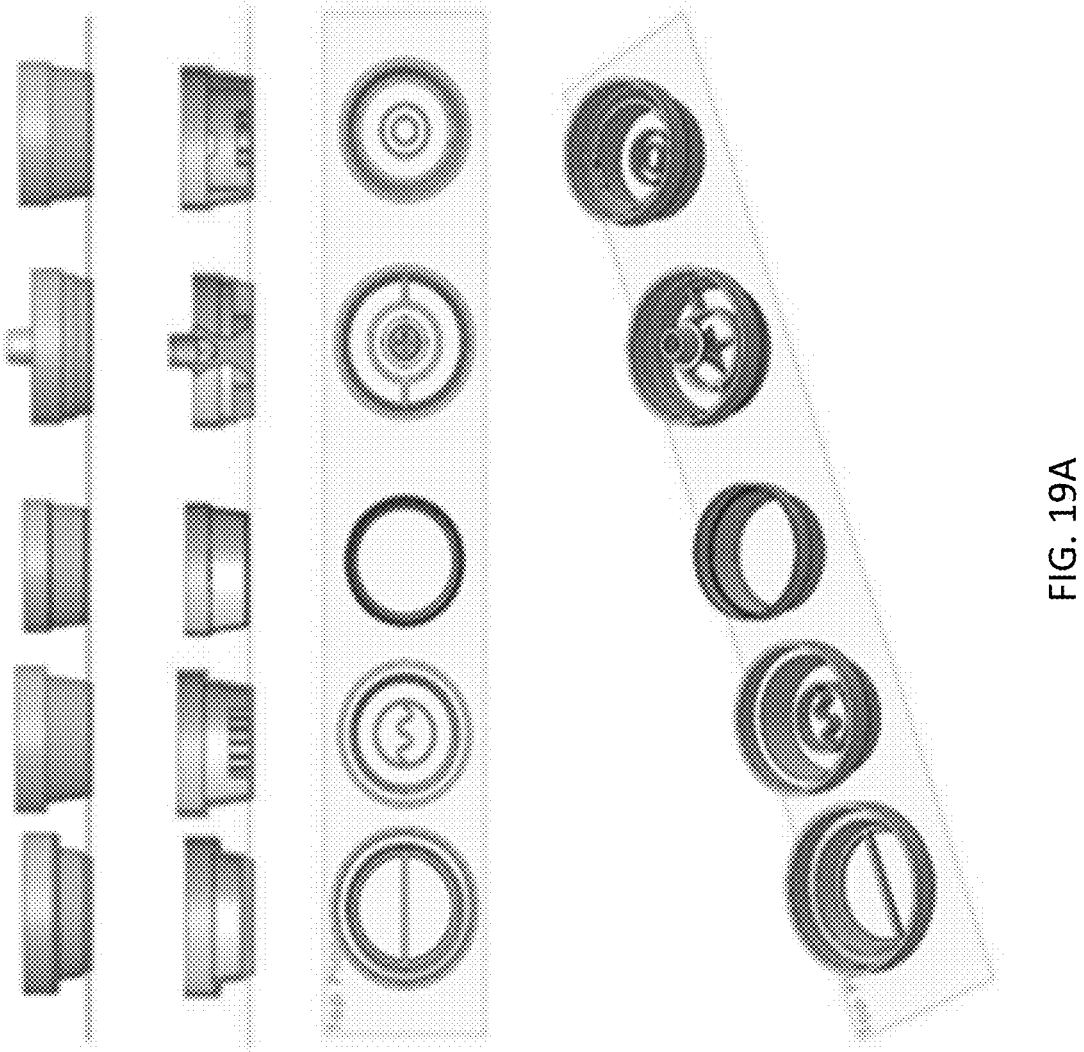
FIG. 19A-19B show exemplary structures by which liquid reagents can be retained within the devices described herein. The different designs are intended to promote mixing of the reagents stored within the structures with the sample that is added to the cup. Generally shallow structures aid mixing as well as structures that allow the sample to be poured directly into the structure cavity. Close proximity of multiple reagent containing structures also aids mixing of the reagents within the sample.
Figure 19B:
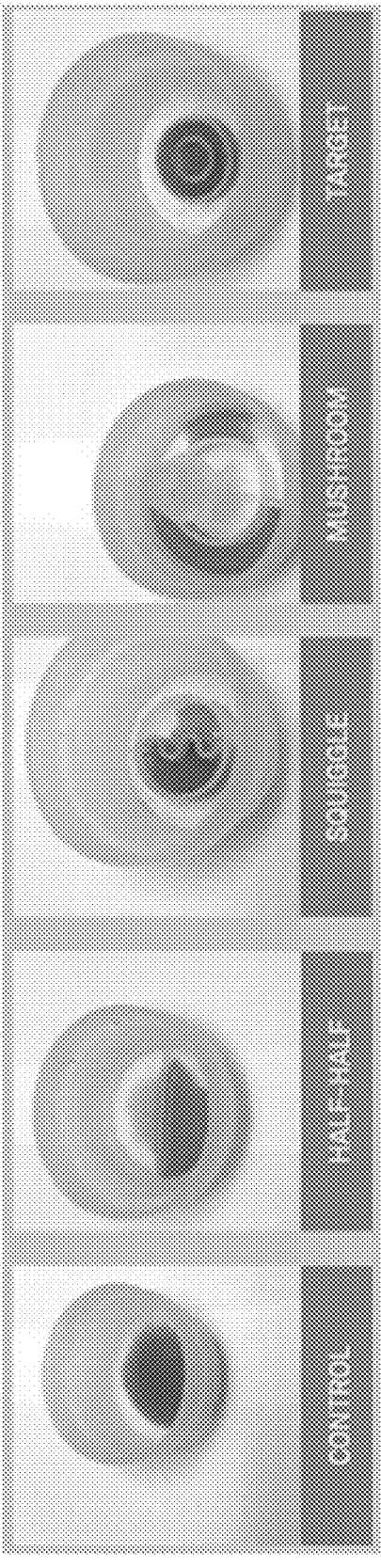

Clogging can be prevented by use of filters to remove sediment prior to allowing the sample to contact the test region. However, the use of filters complicates the usage and/or ability to easily visualize results, requiring alternative strategies or more complicated operation of the device. Herein, unique approaches for addressing these limitations are described. While vertical flow assays typically show low sensitivity, the devices and methods described herein are highly sensitive compared to lateral flow counterparts, clearly demonstrating the utility and novelty of the designs and approaches herein (see FIG. 13).

The devices described herein integrate highly efficient preconcentration, simplicity, and only a fractional increase in cost relative to a standard lateral flow assay. The devices described herein leverage a capture region to help concentrate the capture moiety to high concentrations, which improves capture kinetics by 100-1000 fold compared to other assay formats. The improved capture kinetics allow for efficient capture of analyte at lower concentrations than if the capture moiety were simply applied in solution (e.g., just beads in solution). Thus, the device helps to overcome inherent antibody binding limitations observed in traditional approaches, allowing preconcentration to be applied where antibody kinetics have become a limitation in LFA-based detection.

Moreover, the methods and devices described herein eliminate the need for an elution step. Accordingly, rather than a capture-elute-capture/detect methodology (e.g., a physically separate analyte pre-concentration with an LFA readout), the methods described herein use a simple capture/detect methodology (e.g., a single physically integrated pre-concentration and LFA readout) Eliminating the first capture and elution steps avoids inefficiencies associated with those steps. Moreover, eliminating the need to elute the analyte from the antibody reduces the number/types of antibodies needed in the assay as well as eliminates performance restrictions for those antibodies. In particular, antibodies with extremely good capture performance typically are not able to elute analyte using simple traditional approaches (e.g., pH-based elution). Thus, antibodies with less than optimal capture performance were required to implement a capture-elute-capture/detect strategy with the previous design. Importantly, by enabling the use of more optimal (but potentially poorly eluting antibodies) can have super-linear improvements in capture performance. Indeed the efficiency of capture (amount in versus amount captured) is expected to increase by the square of the on rate. Therefore, if an antibody with an 2-fold improved on-rate can increase capture efficiency 4-fold. Eliminating the need to elute the analyte allows for the use of fewer and better antibodies. Moreover, the use of the porous membrane itself as the capture substrate has the potential to increase capture moiety concentrations by ~4× compared to the capture beads used in other flow-based embodiments. Increased capture moiety concentration directly and proportionally increases the rate of target capture from the sample as it passes through the capture region. Combining these factors, the integrated capture/detect strategy has the potential to improve assay sensitivity more than an order of magnitude over the previous capture-elute-capture/detect strategy.

The assays described herein may also create "multiplexed" assays. A multiplexed assay is where capture moieties are used to detect analytes from the same sample in parallel. Traditional lateral flow introduces sample analytes to one test-line (set of capture moieties) at a time in a linear fashion (i.e., serially). Therefore, the first test line binds to a portion of analyte from the sample before interacting with the next test line. This may be problematic if this binding of analytes along the first line interferes with detecting analytes in the subsequent test lines. For instance, in the case of detecting LAM for tuberculosis, different "species" of LAM can exist within different patients. As a result, it has been difficult to identify a single antibody pair (capture and detection) with sufficient sensitivity and specificity. The methods herein, however, can be used to simultaneously utilize multiple antibodies in parallel to essentially implement multiple antibody pairs in a single test, independently. In this regard, unfiltered sample is allowed to interact with the capture at multiple locations, avoiding any "pre-filtering" bias that might be seen in a lateral flow based approach. This allows one to generate paired, but independent measurements that can be fed into software algorithms for more sensitive and specific diagnostic predictions. For example, one antibody pair might have a receiver operator characteristic (ROC) curve that indicates low specificity and high sensitivity while another pair shows high specificity and low sensitivity. It is known that the results of both tests can be combined to leverage the benefits of both ROC curves to create a test with both high sensitivity and specificity. However, a key assumption is that the measurement of one antibody pair should not bias the measurement of the other antibody pair (i.e., the measurements can be considered independent). The devices provided herein can provide such data and may be key to achieving sensitivity and specificity goals for different applications, such as tuberculosis diagnostic testing.

The sensitivity of the devices described herein to detect LAM in urine was tested. The device used was a gravity-assisted device. A comparison in performance between a traditional lateral flow assay and the gravity-assisted device is shown in FIG. 15. The analytical LoD for the vertical flow embodiment is ~37 pg/mL.

Example 2

Tuberculosis (TB) is a leading infectious killer worldwide. Urine tests for the tuberculosis diagnostic marker LAM have consistently failed to have adequate sensitivity for diagnosis of TB. Specifically, urine LAM tests consistently fall short on sensitivity goals in immunocompetent individuals, where levels of LAM in urine often fall below the limit of detection for ultrasensitive LAM detection platforms such as the electrochemiluminescence-based (ECL) testing platform which has a detection limit of ~10 pg/mL in unfiltered urine. For example, in a recent cohort of subjects tested in Viet Nam, the ECL platform was only able to detect ~60% of TB positive patients. When samples are tested, the levels of LAM appear to be consistently below 10 pg/mL for the vast majority (≥80%) of TB patients around the world, which is currently too low for standard point-of-care detection methods like traditional lateral flow devices.

This example demonstrates the novel finding that filtration of urine matrix components (i.e., interfering substances) achieves adequate performance of LAM-based urine immunoassay/diagnostic for TB that meets the goals set forth for such tests by the World Health Organization (WHO). Without wishing to be bound by theory, it is possible that one or more urine matrix components interferes with effective detection of LAM and results in increased false negatives in patient cohorts with generally lower levels of LAM (e.g., immunocompetent patients with functioning immune systems and lower disease burden).

Figures 30A, 30B:
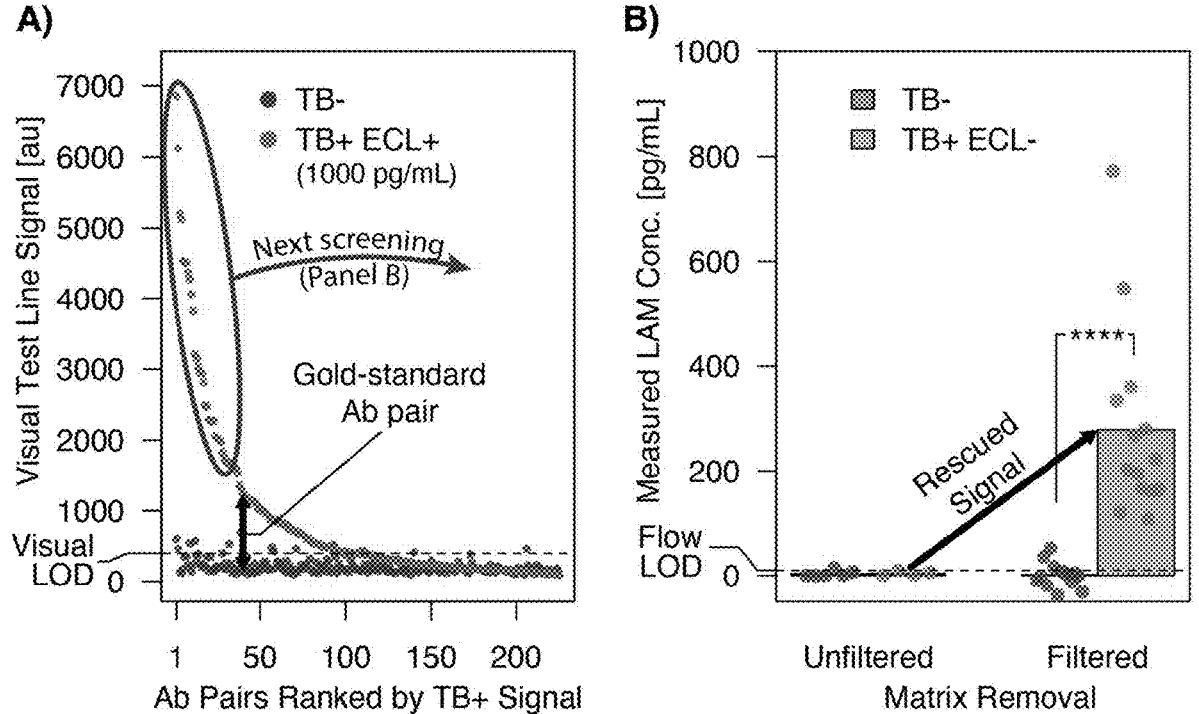
FIG. 30A shows antibody screening and LAM detection with and without urine matrix removal. Antibody screening was performed with clinically pre-characterized patient samples from Africa and South America. Urine LAM concentrations were provided by PATH and FIND using the Meso Scale Diagnostics ECL ELISA platform (ECL) and gold-standard Ab pair for LAM quantification (detection limit of 10 pg/mL). Filtered urine refers to urine that has undergone protein precipitation by treatment with trichloroacetic acid, followed by neutralization with Tris buffer and 10 kDa molecular weight spin filtration/concentration, abbreviated TCA-MW filtration. Ab pairs are tested with lateral flow dipsticks (membranes striped with poly-streptavidin, one antibody biotinylated and one conjugated to 40 nm gold particles). Concentration performed during the TCA-MW filtration method allows the dipstick test to detect ~10 pg/mL of initial unconcentrated LAM in the sample. The graph shows results from one broad screening with urine from a TB− and a TB+ patient with a pre-characterized level of LAM in unfiltered urine (i.e., TB+ECL+). The urines are equivalently TCA-MW filtered/concentrated prior to detection in lateral flow dipstick format in a microtiter plate. Results from 234 Ab pairs were ranked by TB+ signal and plotted. Results show that ~40 Ab pairs provided superior detection compared to the gold-standard Ab pair (black arrow).
FIG. 30B After broad screening efforts, 30 high-interest Ab pairs (red circle in A) were screened on multiple TB− patients (n=6, including HIV+ and HIV− and one potential ECL LAM false positive) as well as patients that were TB+ but had levels of LAM that could not be detected by ECL (i.e., TB+ECL−, n=4, including both HIV+and HIV−). LAM values from ECL pre-characterization in unfiltered urine are shown on the left vs. results for each Ab pair with filtered urine in lateral flow dipstick on the right for both TB− (blue) and TB+ECL− (red) samples. Individual calibration curves for each Ab pair were generated with ECL characterized TCA-MW filtered patient urines to convert dipstick visual test line signals to LAM concentrations. The additional calculation introduces additional noise into the dipstick results (see filtered TB− results), yet all TB+ results were clearly higher than TB− (p<1e-7, Wilcoxon, pairwise, two-tailed).

One method to remove unknown interferent(s) from urine is to use a molecular weight cutoff filter (e.g., a 5 kDa spin column filter). However, such a filter also removes LAM given that the molecular weight of LAM is ~17.4 kDa. Accordingly, herein a combination of trichloroacetic acid (TCA) precipitation (which precipitates protein but not glycolipids/carbohydrates like LAM) and centrifugation to remove the precipitate, followed by retaining the >10 kDA fraction, was performed. This method is referred to herein as TCAMW filtration. TCAMW filtration was used to remove potentially interfering substances from both TB+ and TB− clinical urine samples that were quantified to have levels <10 pg/mL of LAM (as measured by electrochemiluminescence). After TCAMW filtration was performed to remove interfering substances, the TB+ urine samples showed a dramatic increase in measured LAM concentrations across more than 30 antibody pairs. Results suggest that before TCAMW filtration, detectable LAM concentration in both TB+ and TB− patients was <10 pg/mL. After TCAMW filtration, levels increased to between 20-200 pg/mL for TB+ samples but remained undetectable in TB− samples (FIG. 30B). Thus, this example provides the first known demonstration that pre-filtering of urine to remove matrix allows robust immunoassay detection of endogenous LAM that existed in samples but was previously undetectable without pre-filtering. This is a fundamental discovery that has global implications for diagnosis and management of tuberculosis and other diseases where contaminants in a sample reduce/ interfere with detection of target analytes.

The WHO has established that there is a global need for a tuberculosis detection assay that does not require any trained expertise or specialized equipment and has a total cost of $1-$2 per assay. To reduce complexity (e.g., eliminate the need for laboratory space and expertise), instrument cost (e.g., centrifuge), and filter cost (~$10/filter), alternative methods of matrix removal that (i) are sufficient to mitigate the immunoassay interference and (ii) are sufficiently affordable and simple for global health diagnostic testing (e.g., at the point-of-care) were developed herein.

Figures 31A, 31B:
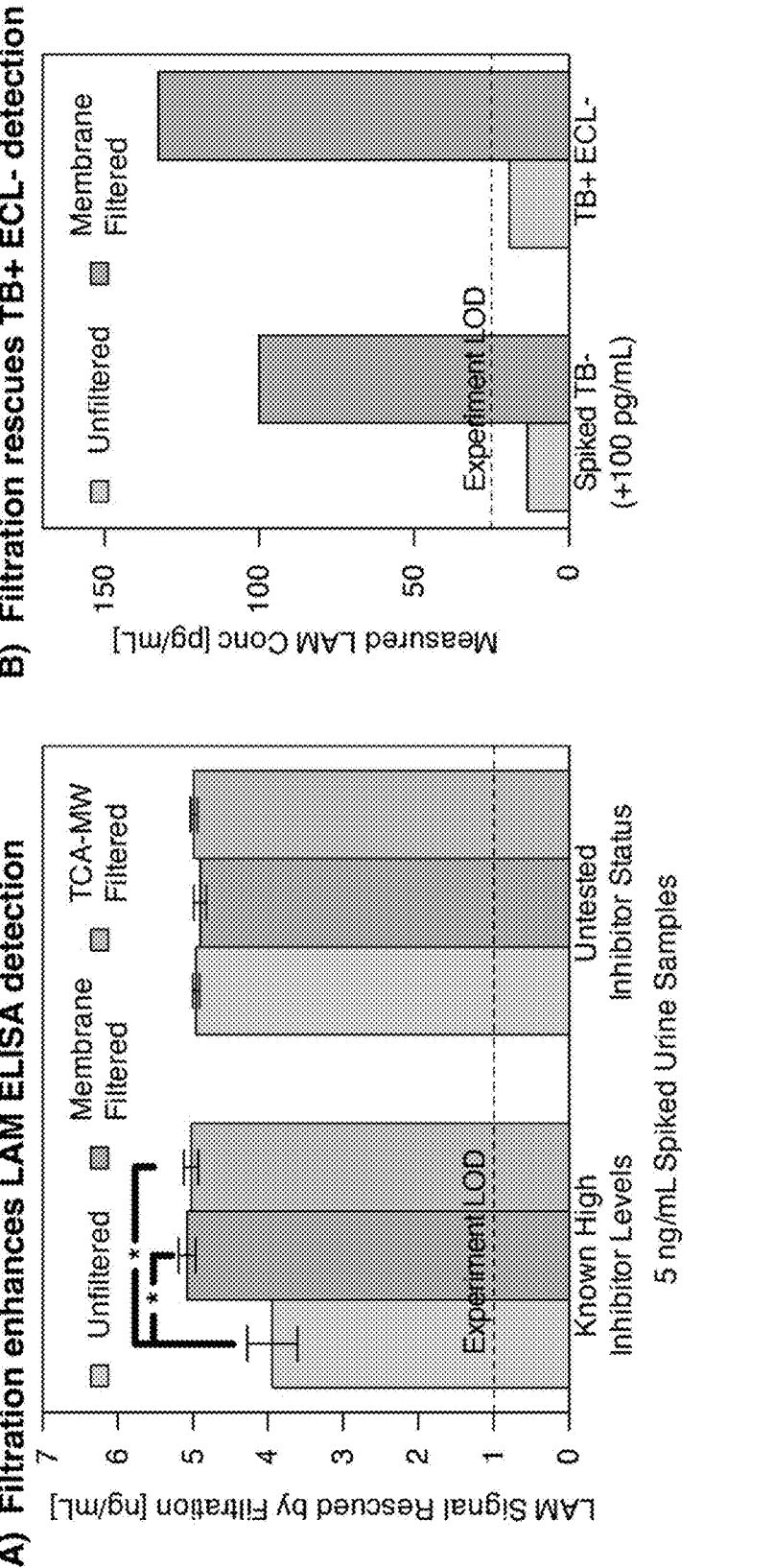
FIGS. 31A-31B shows that membrane filtration of urine enhances LAM detection similarly to TCA-MW filtration.
Figures 37A, 37B:
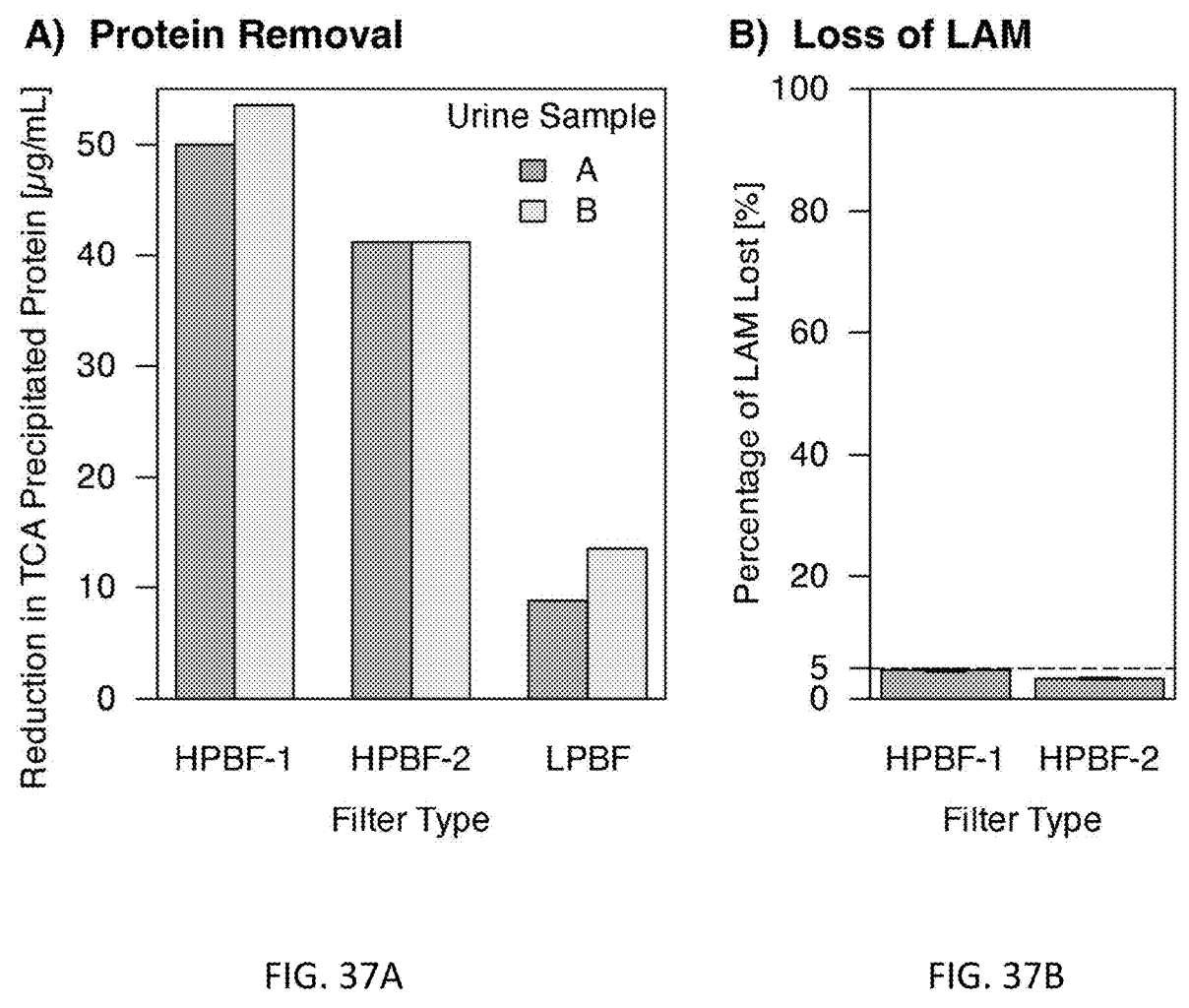

Experiments were performed wherein LAM was added to healthy urine, allowing for observation of the impact of interfering substance(s) on LAM detection compared to detection in buffer. The presence of urine matrix was found to lower detectable signal compared to detection in buffer. The effect of molecular weight filtration was evaluated and compared to other filtration methods to determine if any of other methods could also remove the interferent(s). It was found that filtration with a microscale filter membrane (e.g., membrane with an effective pore size on the order of 0.1-5 µm) that is composed of a material (e.g., nylon, nitrocellulose, or the like) that readily adsorbs urine matrix components, such as proteins and nucleic acids, is able to remove the interferent(s) and improve assay performance. The most effective membrane material tested was nylon. Specifically, positively charged nylon membranes were more effective at removing urine components than negatively charged membranes, with amphoteric and neutral membranes providing performance somewhere in between. Lastly, experimental data show that a nylon filter is able to mitigate urine matrix interference as effectively as the molecular weight filtration method (i.e., the positive control) (FIG. 31) and does not cause significant loss of LAM (FIG. 37). In summary, a microscale filter membrane is demonstrated herein to be a novel and effective filtration method for removing interfering urine matrix.

What is claimed is:

1. A device for detecting one or more analytes in a liquid sample, the device comprising a plurality of porous materials, wherein the device is configured such that a liquid sample flows substantially vertically through at least one of the plurality of porous materials and substantially laterally through at least one of the plurality of porous materials, wherein the plurality of porous materials comprise:

a) a filter system comprising one or more filter components;
    b) at least one wicking component;
    b) c) a porous membrane containing one or more capture moieties held within a defined capture region of the porous membrane; and
    d) at least one absorbent pad,
wherein the device is configured such that the liquid sample flows through the filter system prior to contacting the at least one wicking component, travels substantially laterally in a first direction through the at least one wicking component and onto the porous membrane containing one or more capture moieties, flows through the porous membrane containing one or more capture moieties and into the at least one absorbent pad, and subsequently travels substantially laterally in a second direction through the absorbent pad, wherein the second direction is substantially opposite of the first direction.

2. The device of claim 1, further comprising a barrier between:

the at least one wicking component and the at least one absorbent pad, such that the sample does not enter into the absorbent pad prior to flowing through the porous membrane containing one or more capture moieties.

3. The device of claim 1, wherein the plurality of porous materials further comprise at least one sample pad, wherein the liquid sample is introduced into the device by adding the liquid sample to the at least one sample pad.

4. The device of claim 3, wherein the sample travels through the at least one sample pad and subsequently travels substantially vertically through the filter system.

5. The device of claim 3, wherein the sample travels through the at least one sample pad in both lateral and vertical flows paths.

6. The device of claim 3, wherein at least one sample pad comprises a reservoir which temporarily holds a volume of sample when added to the sample pad.

7. The device of claim 3, comprising at least two sample pads, wherein the at least two sample pads are stacked such that at least a portion of a first sample pad overlaps with at least a portion of a second sample pad.

8. The device of claim 3, wherein the filter system is housed on a lid of the device, and wherein a body of the device comprises at least one sample pad, the porous membrane containing one or more capture moieties held within a defined capture region of the porous membrane, the at least one wicking component, and the at least one absorbent pad.

9. The device of claim 1, further comprising one or more detection reagents added to or dried onto a component of the device.

10. The device of claim 9, wherein the one or more detection reagents are added to or dried onto a component of the device downstream of the filter system.

11. The device of claim 9, wherein the one or more detection reagents are added to or dried onto a reagent pad or a portion of the wicking component.

12. The device of claim 1, wherein at least one filter component comprises a high protein-binding membrane.

13. The device of claim 12, wherein the at least one filter component comprises a nylon membrane.

14. The device of claim 1, wherein the filter system comprises at least two filter components, wherein each filter component comprises pores and/or capture moieties for removal of contaminants.

15. The device of claim 1, further comprising one or more microfluidic channels, wherein at least one microfluidic channel transports the liquid sample to the capture region of the porous membrane.

16. The device of claim 15, further wherein at least one microfluidic channel transports the liquid sample to a control region of the porous membrane.

17. The device of claim 15, wherein the one or more microfluidic channels comprise a mechanism for air escape.

18. The device of claim 1, wherein the porous membrane comprising one or more capture moieties further contains one or more detection moieties.

19. The device of claim 1, further comprising at least one component to prevent the liquid sample from circumventing the filter system.

20. A method of detecting one or more analytes in a liquid sample, the method comprising:

a. applying the liquid sample to the device of claim 1, such that the analyte, if present in the sample, binds to the one or more capture moieties; and b. detecting the one or more analytes, if present in the sample.

21. The method of claim 20, wherein one or more detection moieties are present within the device and/or are added to the device such that the one or more detection moieties binds to the analyte, thereby producing a detectable signal within the defined capture region of the porous membrane.

22. The method of claim 21, wherein the one or more detection moieties are contained within the porous membrane containing one or more capture moieties or the one or more detection moieties are added to the liquid sample prior to applying the liquid sample to the device.

23. The method of claim 20, wherein detecting the one or more analytes comprises assessing the detectable signal within the defined capture region.

\* \* \* \* \*